(12) United States Patent  
Romo et al.

(10) Patent No.: US 8,088,923 B2  
(45) Date of Patent: Jan. 3, 2012

(54) CYCLIC-FUSED BETA-LACTONES AND THEIR SYNTHESIS

(75) Inventors: Daniel Romo, College Station, TX (US); Huda Henry-Riyad, Toronto (CA); Changsuk Lee, College Station, TX (US); Henry Nguyen, College Station, TX (US); Vikram C. Purohit, Bryan, TX (US); Seongho Oh, Singapore (SG)

(73) Assignee: The Texas A&M University System, College Station, TX (US)

( * ) Notice: Subject to any disclaimer, the term of this patent is extended or adjusted under 35 U.S.C. 154(b) by 1070 days.

(21) Appl. No.: 11/775,216

(22) Filed: Jul. 9, 2007

(65) Prior Publication Data

US 2009/0062547 A1 Mar. 5, 2009

Related U.S. Application Data

(60) Provisional application No. 60/819,444, filed on Jul. 7, 2006.

(51) Int. Cl.  
*C07D 471/02* (2006.01)

(52) U.S. Cl. ..................................... 546/116

(58) Field of Classification Search .................. 546/116  
See application file for complete search history.

(56) References Cited

U.S. PATENT DOCUMENTS 5,663,298 A 9/1997 Mizukami et al. ............. 530/332  
7,223,745 B2 5/2007 Chatterjee et al. ............... 514/64

FOREIGN PATENT DOCUMENTS

EP 1 166 781 2/2002  
WO WO 00/43000 7/2000  
WO WO 2004/007506 1/2004

OTHER PUBLICATIONS

Cortez et al. (Abstracts of papers, Abstracts of Papers, 223rd ACS National Meeting, Orlando FL;Publication Date: Apr. 7-11, 2002).*
Oh et al. (Abstracts of Papers, 227th ACS National Meeting, Anaheim, CA;Publication Date: Mar. 28-Apr. 1, 2004).*
Cortez et al. (J. Am. Chem. Soc. 2001, 123; 7945-7946.*
Corey et al. (Angew. Chem. Int. Ed. 1998, 37 (12); 1676-1679).*
Adams et al., "Proteasome inhibition: a new strategy in cancer treatment," *Invest. New Drugs*, 18:109-121, 2000.
Adams et al., "Proteasome inhibitors: a novel class of potent and effective antitumor agents," *Cancer Res.*, 59:2615-2622, 1999.
Adams, "Preclinical and clinical evaluation of proteasome inhibitor PS-341 for the treatment of cancer," *Curr.Opin. Chem. Biol.*, 6:493-500, 2002.
Adams, "Proteasome inhibition: a novel approach to cancer therapy," *Trends Mol. Med.*, 8:S49-54, 2002.
Akaishi et al., "Purification and properties of the 26S proteasome from the rat brain: evidence for its degradation of myelin basic protein in a ubiquitin-dependent manner," *Brain Res.*, 722:139-144, 1996.

Asai et al., "A new structural class of proteasome inhibitors identified by microbial screening using yeast-based assay," *Biochem. Pharm.*, 67:227-234, 2004.
Asai et al., "Belactosin A, a novel antitumor antibiotic acting on cyclin/CDK mediated cell cycle regulation, produced by *Streptomyces* sp," *J. Antibiot.*, 53:81-83, 2000.
Browne et al., "Inhibition of endothelial cell proliferation and angiogenesis by orlistat, a fatty acid synthase inhibitor," *FASEB J.*, 20:2027-2035, 2006.
Caller et al., "Formation of disubstituted beta-lactones using bifunctional catalysis," *Org. Lett.*, 7:1809-1812, 2005.
Cho and Romo, "Total synthesis of (−)-belactosin C and derivatives via double diastereoselective tandem mukaiyama aldol lactonizations," *Org. Lett.*, 9:1537-1540, 2007.
Cortez et al., "Intramolecular, nucleophile-catalyzed aldol-lactonization (NCAL) reactions: catalytic, asymmetric synthesis of bicyclic beta-lactones," *J. Am. Chem. Soc.*, 123:7945-7946, 2001.
Enders and Kallfass, "An efficient nucleophilic carbene catalyst for the asymmetric benzoin condensation," *ACIE*, 41:1743-1745, 2002.
France, S. et al., "Nucleophilic Chiral Amines as Catalysts in Asymmetric Synthesis," *Chem. Rev.*, 103:2985-3012, 2003.
Garcia-Echeverria, "Peptide and peptide-like modulators of 20S proteasome enzymatic activity in cancer cell," *Int. J. Pep. Res. Therap.*, 12:49-64, 2006.
Garcia-Echeverria, "Recent advances in the identification and development of 20S proteasome inhibitors," *Mini Reviews in Medicinal Chemistry*, 2:247-259, 2002.
Getzler et al., "Synthesis of beta-lactones: a highly active and selective catalyst for epoxide carbonylation," *J. Am. Chem. Soc.*, 124:1174-1175, 2002.
Groll et al., "Inhibitor-binding mode of homobelactosin C to proteasomes: new insights into classI MHC ligand generation," *PNAS*, 103:4576-4679, 2006.
Henry-Riyad et al., "Bicyclic- and tricyclic-β-lactones via organonucleophile-promoted bis-cyclizations of keto acids: enantioselective synthesis of (+)-dihydroplakevulin," *Organic Letters*, 8:4363-4366, 2006.
Hirano et al., "Large- and small-scale purification of mammalian 26S proteasomes," *Methods Enzymol.*, 399:227-240, 2005.
Jenni et al., "Architecture of a fungal fatty acid synthase at 5 A Resolution," *Science*, 311:1263-1267, 2006.
Kerr and Rovis, "Effect of the michael acceptor in the asymmetric intramolecular stetter reaction," *Synlett.*, 12:1934-1936, 2003.
Kerr et al., "A highly enantioselective catalytic intramolecular Stetter reaction," *J. Am. Chem. Soc.*, 124:10298-10299, 2002.

(Continued)

*Primary Examiner* — Andrew D Kosar  
*Assistant Examiner* — Valerie Rodriguez-Garcia  
(74) *Attorney, Agent, or Firm* — Christensen O'Connor Johnson Kindness PLLC

(57) ABSTRACT

The present invention provides a concise synthetic method for generating lactam-fused beta-lactones that feature, in some embodiments, a tertiary fused carbinol, quaternary carbons, and a reactive beta-lactone moiety available for further reactions. The present invention further provides compounds synthesized by this method as well as methods of using these compounds as inhibitors of the proteasome and fatty acid synthase.

25 Claims, 1 Drawing Sheet

OTHER PUBLICATIONS

Knowles et al., "A fatty acid synthase blockade induces tumor cell-cycle arrest by down-regulating Skp2," *J. Biol. Chem.*, 279:30540-30545, 2004.

Kridel et al., "Orlistat is a novel inhibitor of fatty acid synthase with antitumor activity," *Cancer*, 64:2070-2075, 2004.

Kumaraswamy and Markondaiah, "Stereoselective synthesis of belactosin C and its derivatives using a catalytic proline catalyzed crossed-aldol reaction," *Tet. Lett.*, 48:1707-1709, 2007.

Kumaraswamy et al., "Oppolzer sultam directed aldol as a key step for the stereoselective syntheses of antitumor antibiotic belactosin C and its synthetic congeners," *J. Org. Chem.*, 71:337-340, 2006.

Lall et al., "Serine and threonine beta-lactones: a new class of hepatitis A virus 3C cysteine proteinase inhibitors," *J. Org. Chem.*, 67:1536-1547, 2002.

Larionov and de Meijere, "Enantioselective total synthesis of Belactosin A, Belactosin C, and its homoanalogue," *Org. Lett.*, 6:2153-2156, 2004.

Lowe and Vederas, "Naturally ocurring β-lactones: occurrence, syntheses and properties. A review," *Org. Prep. Proceed. Int.*, 27:305-346, 1995.

Ma et al., "Concise total synthesis of (±)-salinosporamide A, (±)-cinnabaramide A, and derivatives via a bis-cyclization process: implications for a biosynthetic pathway?," *Organic Letters*, 9:2143-2146, 2007.

Maier et al., "Architecture of mammalian fatty acid synthase at 4.5 Å resolution," *Science*, 311:1258-1262, 2006.

Mellgren, "Specificities of cell permeant peptidyl inhibitors for the proteinase activities of mu-calpain and the 20 S proteasome," *J. Biol. Chem.*, 272:29899-29903, 1997.

Murray et al., "Proteasome inhibitors as anti-cancer agents," *Anti-cancer Drugs*, 11:407-417, 2000.

Oh et al., "Asymmetric synthesis of bicyclic β-lactones via the intramolecular, nucleophile-catalyzed aldol lactonization: improved efficiency and expanded scope," *J. Org. Chem.* 70:2835-2838, 2005.

Pizer et al., "Fatty acid synthase (FAS): a target for cytotoxic antimetabolites in HL60 promyelocytic leukemia cells," *Cancer Res.*, 56:745-751, 1996.

Pommier and Pons, "Recent advances in β-lactone chemistry," *Synthesis*, pp. 441-459, 1993.

Prasad and Chandrakumar, "Asymmetric synthesis of α-methoxyarylacetic acid derivatives," *Tetrahedron: Asymmetry*, 16:1897-1900, 2005.

Purohit et al., "Practical, catalytic, asymmetric synthesis of beta-lactones via a sequential ketene dimerization/hydrogenation process: inhibitors of the thioesterase domain of fatty acid synthase," *J. Org. Chem.*, 71:4549-4958, 2006.

Ramiandrasoa et al., "Poly(β-malic acid alkyl esters) derived from 4-alkyloxycarbonyl-2-oxetanones obtained via the ketene route," *Vert, M Polym. Bull.*, 30:501-508, 1993.

Rieth et al., "Single-site beta-diiminate zinc catalysts for the ring-opening polymerization of beta-butyrolactone and beta-valerolactone to poly(3-hydroxyalkanoates)," *J. Am. Chem. Soc.*, 124:15239-15248, 2002.

Romo et al., U.S. Appl. No. 11/775,154, "Novel Belactosin Derivatives as Therapeutic Agents/Biological Probes and Their Synthesis," filed Jul. 9, 2007.

Romo et al., U.S. Appl. No. 60/819,444, "Cyclic-fused beta-lactones and their synthesis," filed Jul. 7, 2006.

Scutt, "EMD273316 & EMD95833, type 4 phosphodiesterase inhibitors, stimulate fibroblastic-colony formation by bone marrow cells via direct inhibition of PDE4 and the induction of endogenous prostaglandin synthesis," *BMC Pharmacol.*, 4:10, 2004.

Seitzberg et al., "Design and synthesis of a new type of ferrocene-based planar chiral DMAP analogues. A new catalyst system for asymmetric nucleophilic catalysis," *J. Org. Chem.*, 70:8332-8337, 2005.

Ugai et al., "Purification and characterization of the 26S proteasome complex catalyzing ATP-dependent breakdown of ubiquitin-ligated proteins from rat liver," *J. Biochem.* (Tokyo), 113:754-768, 1993.

Wang et al., "β-Lactones as Intermediates for Natural Product Total Synthesis and New Transformations," *Heterocycles*, 64:605-658, 2004.

Wilson and Fu, "Asymmetric Synthesis of Highly Substituted-Lactones by Nucleophile-Catalyzed [2+2] Cycloadditions of Disubstituted Ketenes with Aldehydes," *Angew. Chem. Int.* 116:6518-6520, 2004.

Wynberg and Staring, "Asymmetric synthesis of (S)- and (R)-malic acid from ketene and chloral," *J. Am. Chem. Soc.*, 104:166-168, 1982.

Wynberg and Staring, "Catalytic asymmetric synthesis of chiral 4-substituted 2-oxetanones," *J. Org. Chem.*, 50:1977-1979, 1985.

Wynberg, "Asymmetric Catalysis by Alkaloids," *Stereochem.*, 16:87-130, 1986.

Yang and Romo, "Methods for the Synthesis of Optically Active b-Lactones (2-Oxetanones)," *Tetrahedron*, 55:6403-6434, 1999.

Yang and Romo, "Practical, one-step synthesis of optically active β-lactones via the tandem mukaiyama aldol-lactonization (TMAL) reaction," *J. Org. Chem.*, 63:1344-1347, 1998.

Yang et al., "Studies of the tandem mukaiyma aldol-lactonization (TMAL) reaction: a concise and highly diastereoselective route to β-lactones applied to the total synthesis of the potent pancreatice lipase inhibitor, (−)-panclicin-D," *Tetrahedron*, 53:16471-16488, 1997.

Zhu et al., "Cinchona alkaloid-lewis acid catalyst systems for enantioselective ketene-aldehyde cycloadditions," *J. Am. Chem. Soc.*, 126:5352-5353, 2004.

Cortez, G.S., et al., "Asymmetric Organocatalysis: Synthesis of Bicyclic β-Lactones," slides presented at the 223rd American Chemical Society National Meeting, Orlando, FL, Apr. 7-11, 2002 (cf. Item U of the Notice of References attached to Nov. 10, 2010, Office Action), 19 pages.

Oh, S., et al., "Further Studies of the Chiral Nucleophile-Catalyzed, Intramolecular Aldol-Lactonization (NCAL) Reaction: Application to the Synthesis of Omuralide and Salinosporamide A Derivatives," slides presented at the 227th American Chemical Society National Meeting, Anaheim, CA, Mar. 28-Apr. 1, 2004 (cf. Item V of the Notice of References attached to Nov. 10, 2010, Office Action), 15 pages.

\* cited by examiner

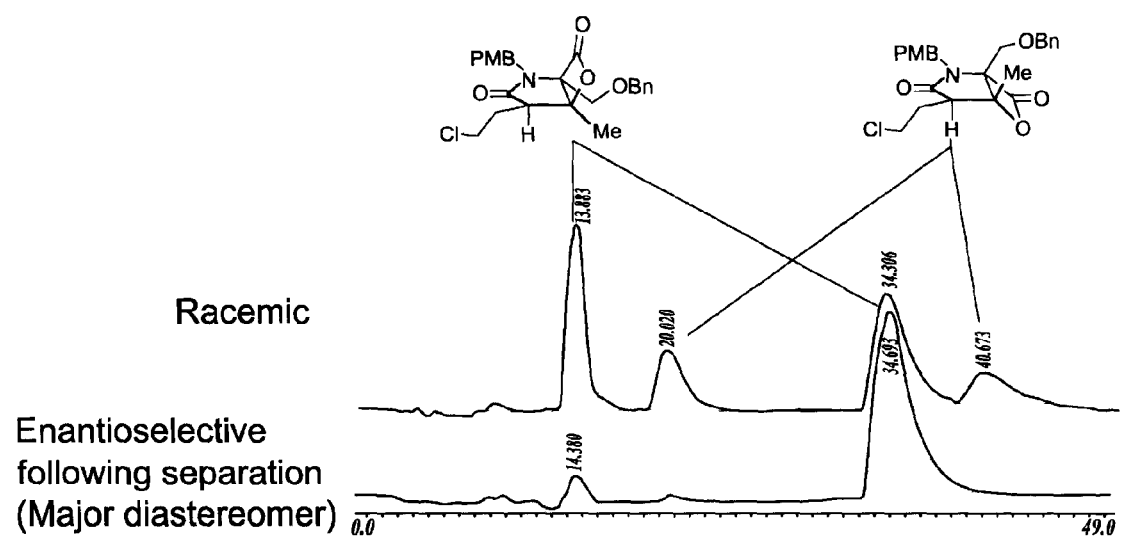
Racemic
Enantioselective following separation (Major diastereomer)

CYCLIC-FUSED BETA-LACTONES AND THEIR SYNTHESIS

This application claims the benefit of U.S. Provisional Application Ser. No. 60/819,444 filed Jul. 7, 2006, the contents of which are incorporated herein in their entirety.

This invention was made with government support under CHE-0077917 awarded by the National Science Foundation (NSF) and GM069784-01 by the National Institutes of Health (NIH). The government has certain rights in the invention.

BACKGROUND OF THE INVENTION

A. Field of the Invention

The present invention relates generally to cyclic fused beta-lactones and their synthesis. Cyclic-fused beta-lactones are found in many natural products, some of which are known to have therapeutic value. Thus, in certain aspects, the compounds and syntheses of the present invention provide useful synthetic intermediates for natural product preparations. In other aspects, compounds of the present invention can be administered for therapeutic purposes.

B. Background of the Invention

In recent years, the asymmetric synthesis of beta-lactones has become an area of active research. For a review of this subject area, see: Yang and Romo, 1999; for more recent advances, see: Getzler et al., 2002; Zhu et al., 2004; Wilson and Fu, 2004; and Calter et al., 2005. This is due namely to the fact that these cyclic compounds are useful synthetic intermediates for natural product synthesis, are found in a growing number of bioactive natural products, and have continued potential as enzyme inhibitors and as monomers for polymer synthesis. For relevant articles regarding these topics, see: Wang et al., 2004; Lowe and Vederas, 1995; Lall et al., 2002; and Rieth et al., 2002. In particular, bicyclic-beta-lactones are structural motifs found in several natural products including Omuralide, salinosporamide, spongiolactone and the triterpenes lueolactone and papyriogenin G. For reviews of naturally occurring beta-lactones and their synthesis, see: Lowe and Vederas, 1995; and Pommier and Pons, 1995. More importantly, the presence of the beta-lactone in these bicyclics allows for facile conversion into a variety of functional arrays and thus these bicyclics may serve as useful diversity scaffolds.

The Wynberg beta-lactone synthesis was one of the first practical, catalytic asymmetric reactions developed and its utility was demonstrated by the fact that Lonza Ltd. employed this process for the large-scale synthesis of optically active malic and citramalic acids (Wynberg and Staring, 1982; Wynberg, 1986). Limitations to the Wynberg procedure are the need for a ketene generator and the requirement of activated (i.e. typically beta-dihalogenated) aldehyde substrates. In early studies by Wynberg, it was determined that at least two beta-halogen atoms were required (see: Wynberg and Staring, 1985. For other activated carbonyl compounds that participate in this reaction, see: Ramiandrasoa et al., 1993).

The inventors previously developed an intramolecular, catalytic, asymmetric, nucleophile catalyzed aldol-lactonization (NCAL) process of aldehyde acids that leads to a variety of novel, carbocycle-fused beta-lactone systems. Cortez et al., 2001. This represented the first example of a catalytic, asymmetric NCAL reaction with unactivated (i.e. non-chlorinated) aldehydes and this methodology merges catalytic, asymmetric beta-lactone synthesis with carbocycle construction employing an organic catalyst. Only carbocyclic compounds were produced via this procedures. A need exists, however, to extend this methodology to other substrates besides aldehyde acids, particularly more tractable substrates such as keto acids. Moreover, synthetic routes for producing heteroatom-containing products are needed as well.

SUMMARY OF THE INVENTION

The present invention overcomes deficiencies in the art by providing a concise synthetic method for generating heterocyclic-fused beta-lactones that feature, in some embodiments, a tertiary fused carbinol, quaternary carbons, and a reactive beta-lactone moiety available for further reactions. In some embodiments of the invention, keto acids are used as substrates. Typically, compounds can be produced using methods disclosed herein in fewer steps than disclosed previously, and often in higher yield and with improved stereoselectivity. The present invention further provides compounds synthesized by this method. In some embodiments, compounds generated by the method of the present invention can be further synthetically modified to generate compounds such as natural products. These natural products may have therapeutic use, such as salinosporamide, which, in one aspect, inhibits proteasome activity and therefore may be of use as an anticancer agent. Other natural products include oxylipin (DNA polymerase inhibitor) and verrillin (a cembranoid). Compounds of the present invention (with or without further synthetic modification) may also be administered for therapeutic purposes.

Accordingly, one general aspect of the present invention concerns a method of synthesizing a heterocyclic-fused beta-lactone, comprising reacting a carbonyl/carboxylic acid difunctionalized amide with an activating agent, a base, and a nucleophilic promoter. The carbonyl-carboxylic acid-containing compound, activating agent, base and nucleophilic promoter are each considered "substrates" of the reaction. In yet further general aspects of the present invention, the compounds synthesized by the method of the present invention possess attractive synthetic features, including one or more stereocenters, one or more tertiary carbinol centers, which may be masked by a protecting group, one or more quaternary carbons, and a reactive beta-lactone. As such, in general aspects of this method, this combination of substrates results in heterocyclic-fused beta-lactones that are useful synthetic intermediates in the preparation of natural products, natural products of therapeutic value, non-natural products, and non-natural products of therapeutic value.

In certain embodiments, the carbonyl/carboxylic acid difunctionalized amide is further defined as a compound of formula (I):

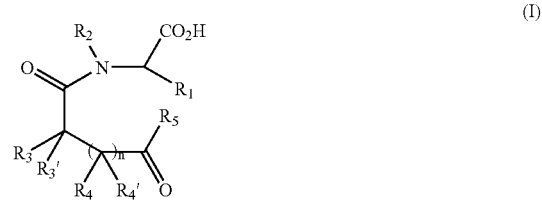

wherein: $R_1$ is selected from the group consisting of H, alkyl, alkenylalkyl, aryl, -alkyl-protected hydroxy, halo, amino, protected amine, aminocarbonyl, alkylamino and sulfonyl; $R_2$ is selected from the group consisting of H, alkyl, aryl, —OH and amine protecting group; $R_3, R_3', R_4, R_4', R_5$ and $R_6$ are each independently selected from the group consisting of H, alkyl, aryl and aralkyl, or $R_3$ and $R_3'$ together form a cycloalkyl; and n=0 or 1. Optical isomers of compounds of formula (I) are also specifically contemplated. In certain embodiments, $R_1$ is alkyl. In certain embodiments, $R_3$ is H or alkyl. In certain embodiments, n is 0. In certain embodiments, $R_5$ is $CH_2OH$. In certain embodiments, a carbonyl/carboxylic acid difunctionalized amide is of the following formula:

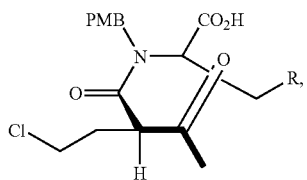

wherein R is H, alkyl, aryl, alkoxy, acyl, or aralkyl. In certain embodiments, a carbonyl/carboxylic acid difunctionalized amide is of the following formula:

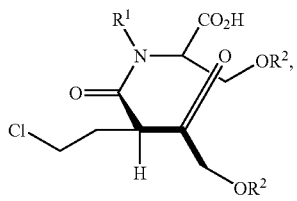

wherein $R^1$ is a nitrogen protecting group and $R^2$ is a hydroxy protecting group. In particular embodiments, the carbonyl/carboxylic acid difunctionalized amide is selected from the group consisting of:

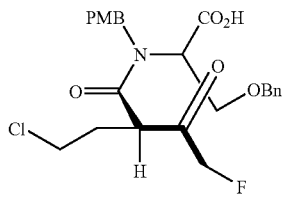

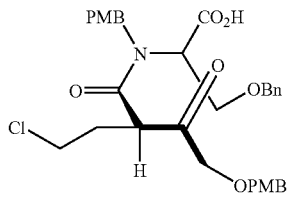

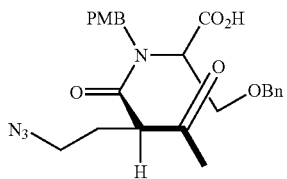

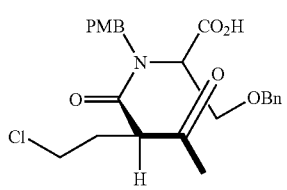

-continued

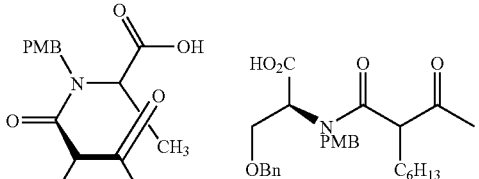

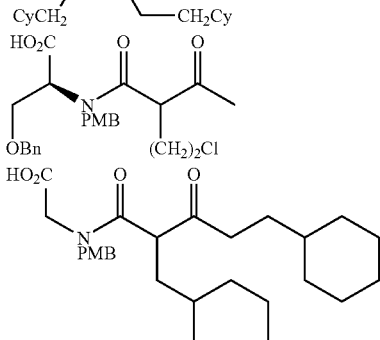

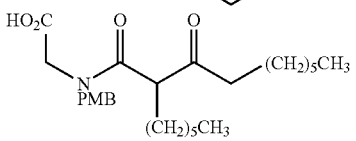

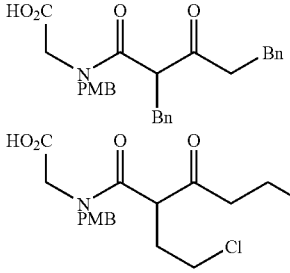

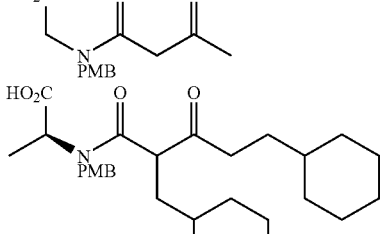

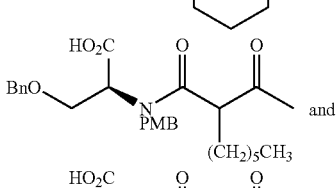

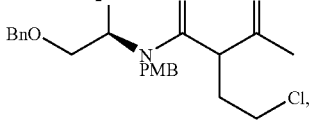

and optical isomers thereof.

Activating agents in the context of the present invention are well-known to those of skill in the art. In certain embodiments, the activating agent is selected from the group consisting of Mukaiyama's reagent and derivatives thereof, oxalyl chloride, thionyl chloride, aryl sulfonyl halides, an acid chloride, a chloroformate, dicyclohexylcarbodiimide and derivatives (e.g., diisopropylcarbodiimide and 1-ethyl-3-(3-dimethylaminopropyl) carbodiimide hydrochloride), SOCl$_2$ and P(O)Cl$_3$. In certain embodiments, the activating agent is selected from the group consisting of

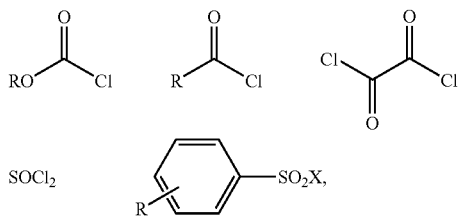

wherein R is typically selected from the group consisting of H, alkyl, cycloalkyl, aryl, acyl, acyloxy (carbamate), hydroxy, protected hydroxy, trialkylsilyloxy, alkoxy, bis-acylamino, acylamino (urea), amido, alkylamine, dialkylamine, diarylamine, dialkylarylamine, protected amine, an amine protecting group and any combination of one or more of these groups; X is typically a halogen; and Y is typically an anion. Persons of ordinary skill in the art will realize that R may be chosen from a wide variety of organic moieties. In particular embodiments, the activating agent is Mukaiyama's reagent or derivatives thereof, such as compounds of formula (II):

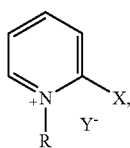

(II)

wherein R is alkyl, X is halogen and Y is a counterion. In particular embodiments, R is methyl or n-propyl, X is chloro or bromo, and the Y is triflate or iodo. Optical isomers of activating agents are also contemplated. While the exact mechanism of the method of the present invention is not precisely known, it is thought that the activating agent plays the role of activating the carboxylic acid functional group to generate a reactive enolate intermediate.

Bases that may be used in methods of the present invention are well-known to those of ordinary skill in the art. Hindered bases (an art-recognized term referring to sterically hindered bases) are typically preferred. Hindered bases may, in certain embodiments, be a trialkylamine, a triarylamine, a triaralkylamine, or a substituted pyridine. In certain embodiments, the base is selected from the group consisting of a trialkylamine, a triarylamine, a triaralkylamine, a substituted pyridine, an inorganic base and a proton sponge. In certain embodiments, the trialkylamine is selected from the group consisting of i-Pr$_2$NEt, Et$_3$N, i-Bu$_3$N and i-Pr$_3$N. A substituted pyridine may, in certain embodiments, be selected from the group consisting of a 2,6-dialkyl pyridine, a 2,6-diaryl pyridine and a 2,6-dialkylaryl pyridine. In particular embodiments, the 2,6-dialkyl pyridine is selected from the group consisting of 2,6-dimethylpyridine and 2,6-di-t-butylpyridine. Inorganic bases include, but are not limited to, K$_2$CO$_3$, K$_3$PO$_4$, NaHCO$_3$ and Na$_2$CO$_3$. Non-limiting examples of proton sponges include 1,8-bis(dimethylamino)naphthalene and 1,8-bis(hexamethyltriaminophosphazenyl)naphthalene. As mentioned above, while the exact mechanism of the method of the present invention is not precisely known, it is thought that the base facilitates activation of the carboxylic acid—that is, it facilitates the generation of a reactive enolate intermediate.

Nucleophilic promoters useful in methods of the present invention are well-known to those of skill in the art. Useful references for these nucleophiles include Johannsen et al. (2005); Lecka et al. (2003); Enders (2002); Rovis (2002); and Rovis (2003), each of which are incorporated by reference in their entireties. The method of claim 1, wherein the nucleophilic promoter is selected from the group consisting of a nitrogen-containing nucleophile, a phosphine-containing nucleophile, a carbene-containing nucleophile and optical isomers of any one of these nucleophiles. In certain embodiments, a nitrogen-containing nucleophile is a pyridine-based nucleophile. In certain embodiments, the nucleophilic promoter is selected from the group consisting of dimethylaminopyridine, 4-pyrrolidinopyridine, and 3a-3jj:

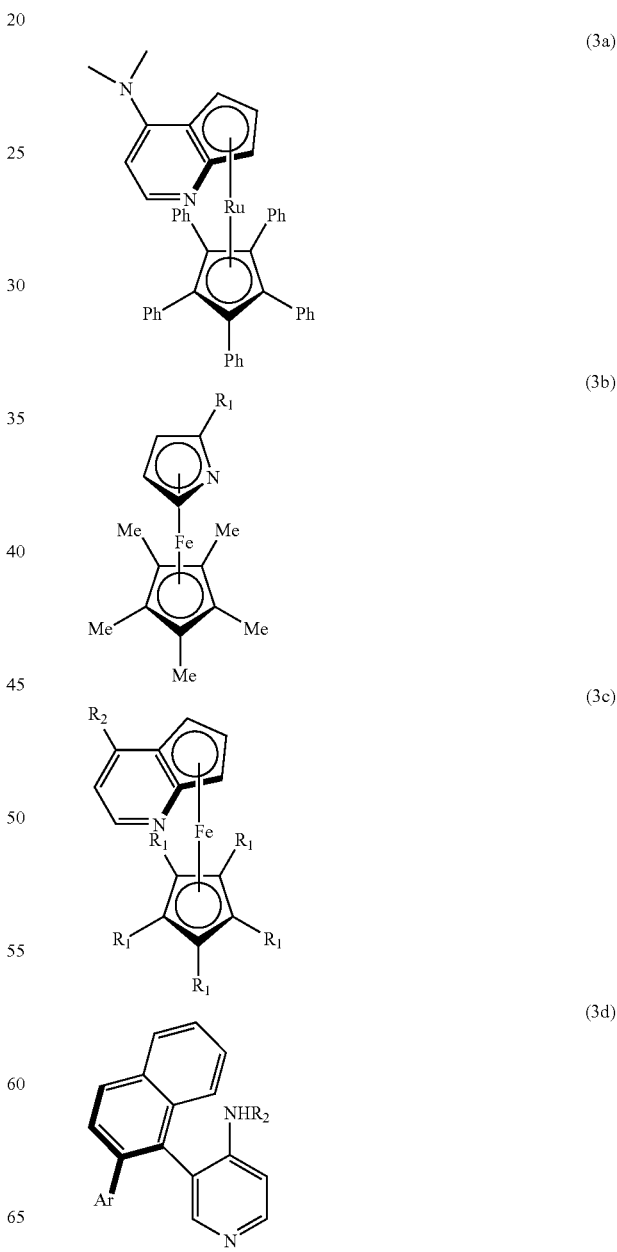

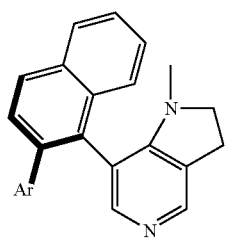
(3e)
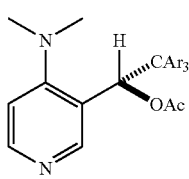
(3f)
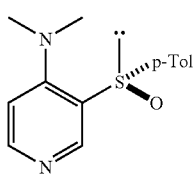
(3g)
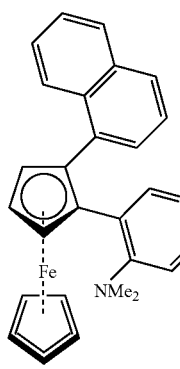
(3h)
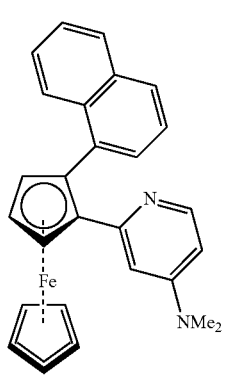
(3i)
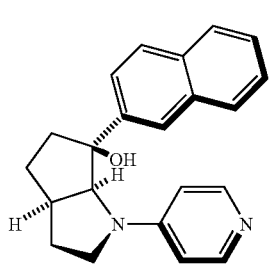
(3j)
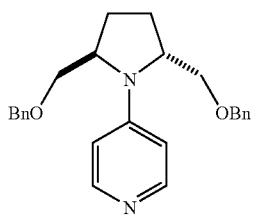
(3k)
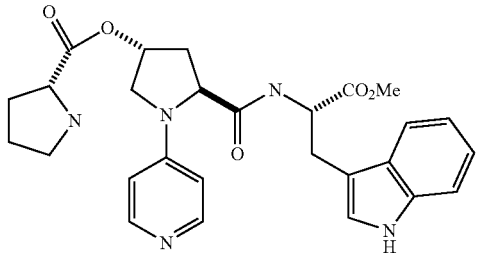
(3l)
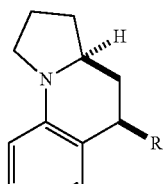
(3m)
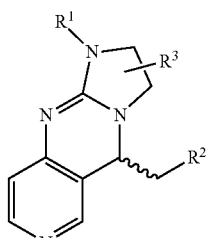
(3n)
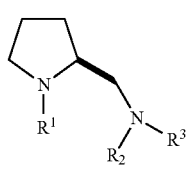
(3o)
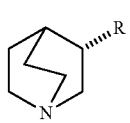
(3p)
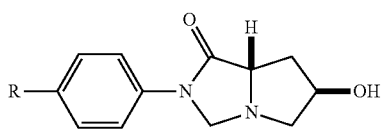
(3q)
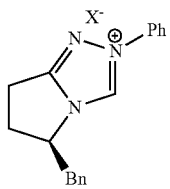
(3r)

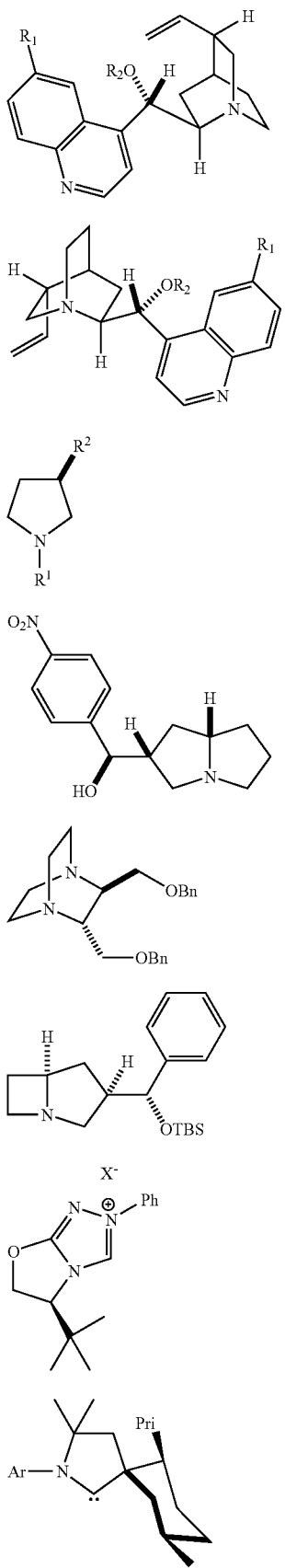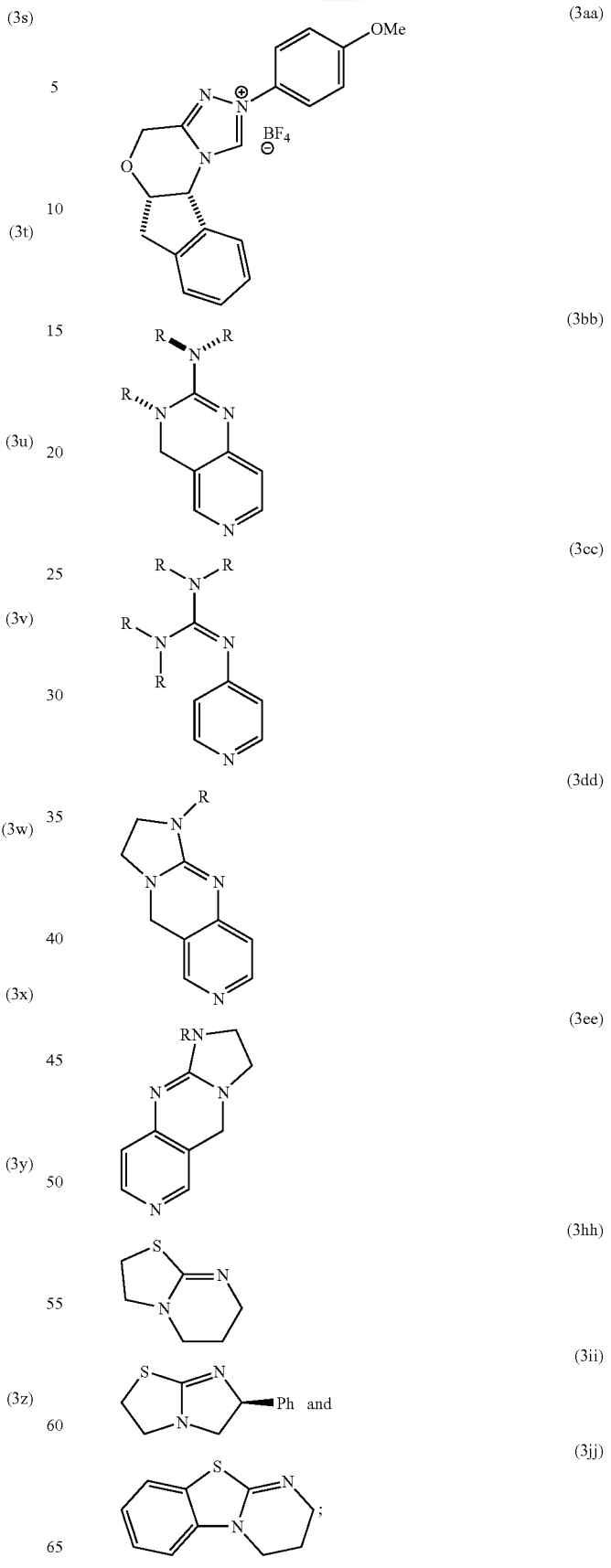

wherein: R, $R_1$, $R_2$ and $R_3$ and $R_4$ are each independently selected from the group consisting of hydrogen, alkyl, alkylamino, aryl, alkoxy, —OSi(alkyl)$_3$, —Si(alkyl)$_3$, arylcarbonyl, protected hydroxy and any combination of one or more of these groups; and $X^-$ is a counterion. In particular embodiments regarding compounds 3a-3jj, R, $R_1$, $R_2$ and $R_3$ are each independently selected from the group consisting of hydrogen, methyl, phenyl, benzyl, dimethylamino, pyrrolidino, —CH$_2$O-triethylsilyl, —OCH$_3$, —OSi(alkyl)$_3$, —Si(alkyl)$_3$ and arylcarbonyl. In certain embodiments, an aryl substituent of compounds 3a-3jj is 1- or 2-naphthyl. In certain embodiments, the compound (3n) is further defined as:

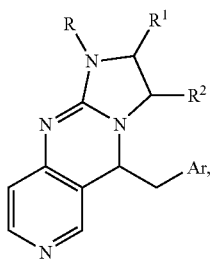

(3n)

wherein R, $R^1$, $R^2$ and $R^3$ may each independently be H, alkyl or aryl, and Ar may be aryl, such as 1- or 2-naphthyl. Regarding compounds 3m-3o, R, $R^1$, $R^2$ and $R^3$ may each independently be H, alkyl, or aryl, in certain embodiments. Regarding compounds 3bb-3jj, R may be H, alkyl, or aryl, in certain embodiments. Suitable counterions are well-known to those of skill in the art. The counterion $(X^-)$ may, in certain embodiments, be selected from the group consisting of $BF_4$, $ClO_4$, triflate and chloro. As mentioned above, while the exact mechanism of the method of the present invention is not precisely known, it is thought that in some methods, the nucleophilic promoter increases the nucleophilicity of certain intermediate ammonium enolates of the present invention, thereby promoting the generation of cyclic-fused beta-lactones.

In particular embodiments, when employing methods as described herein, a compound of formula (IV) is generated as an intermediate:

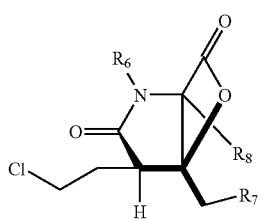

(IV)

wherein: $R_6$ is selected from the group consisting of H, alkyl, aryl, —OH and an amine protecting group; $R_7$ is H or a protected hydroxy; and $R_8$ is —CH$_2$OH, —CH$_2$-protected hydroxy, or —C(O)H. Derivatives and optical isomers of the compound of formula (IV) are also specifically contemplated. In particular embodiments, the compound of formula (IV) is further defined as a compound of formula:

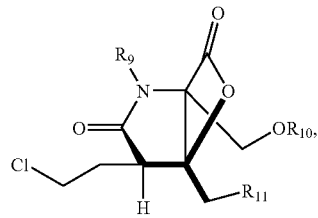

(V)

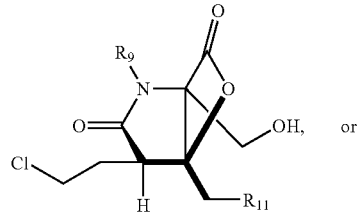

(VI)

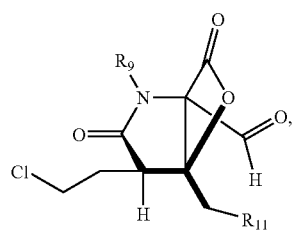

(VII)

wherein $R_9$ and $R_{10}$ are each independently H, p-methoxybenzyl, 3,4-dimethoxybenzyl, or other nitrogen protecting group chosen from p-toluenesulfonamide or $R_{12}OC(O)$, wherein $R_{12}$ is benzyl, trimethylsilylethyl, or allyl; and $R_{11}$ is H, OBn, OPMB or ODMB.

Any lactam-fused beta-lactone that may be made via methods of the present invention is specifically contemplated. In particular embodiments, employment of a method as described herein produces a lactam-fused beta-lactone of formula (VIII):

(VIII)

wherein: $R_1$ is selected from the group consisting of H, alkyl, alkenylalkyl, aryl, -alkyl-protected hydroxy, halo, amino, protected amine, aminocarbonyl, alkylamino, sulfonyl; $R_2$ is selected from the group consisting of H, alkyl, aryl, —OH and an amine protecting group; $R_3$, $R_3'$, $R_4$, $R_4'$, $R_5$ and $R_6$ are each independently selected from the group consisting of H, alkyl, aryl and aralkyl; or $R_3$ and $R_3'$ together form a cycloalkyl; and n=0 or 1. Optical isomers are also contemplated. In certain embodiments, n=1.

Persons of ordinary skill in the art will be familiar with synthetic methods that can be used to manipulate compounds of the present invention to arrive at natural products, including natural products of therapeutic value, as well as other derivatives of the claimed compounds. As such, any compound as described herein may be reacted further, in certain embodiments, to produce one or more derivatives. Such derivatives may be substantially free of certain stereoisomers. In certain embodiments, a compound of formula (VIII) may be further reacted to produce derivatives thereof. For example, in certain methods, a step of removing a protecting group from a compound, such as a compound of formula (VIII), is contemplated. In certain embodiments, the lactam-fused beta-lactone may be subjected to acid- or base-hydrolysis. Such reaction conditions may produce a hydroxy acid (in other words, the reaction conditions open the beta-lactone ring). This ring-opened compound may then be reacted further to produce additional derivatives. Persons of skill in the art are familiar with acid- and base-hydrolysis conditions suitable for such ring-opening reactions (see, e.g., Smith and March, 2001). In certain embodiments, the hydroxy acid may be reacted with cysteine, glutathione, or derivatives thereof such that a product is produced that comprises a thioester. Compounds comprising a thioester may be biologically relevant as internal processing of beta-lactone containing structures may alternate between beta-lactone, ring-opened hydroxy acid, and thioester containing compounds, (including reverse-reactions) depending on where these compounds are in the biosynthetic pathway. Reactions to produce thioesters are also well-known in the art (Smith and March, 2001).

Other aspects of the present invention contemplate a compound of formula (IX):

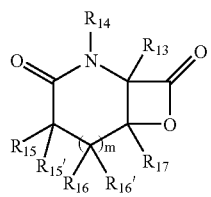

(IX)

wherein: $R_{13}$ is selected from the group consisting of H, alkyl, alkenylalkyl, aryl, -alkyl-protected hydroxy, —C(O)H, halo, amino, protected amine, aminocarbonyl, alkylamino and sulfonyl; $R_{14}$ is selected from the group consisting of H, alkyl, aryl, —OH and amine protecting group; $R_{15}$ is selected from the group consisting of H, alkyl, aryl, aralkyl and

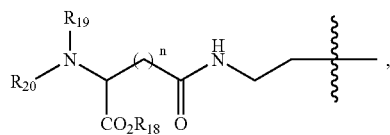

wherein $R_{18}$ is H or a carboxylic acid protecting group; and $R_{19}$ and $R_{20}$ are each independently selected from the group consisting of H, alkyl, aryl, an amine protecting group and

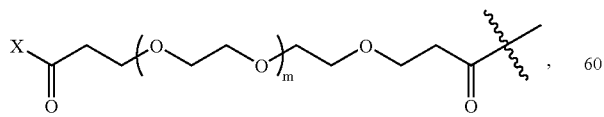

wherein m equals 1-5 and X is a fluorophore; $R_{15}'$ is selected from the group consisting of H, alkyl, aryl and aralkyl, or $R_3$ and $R_3'$ together form a cycloalkyl; $R_{16}$, $R_{16}'$ and $R_{17}$ are each independently selected from the group consisting of H, alkyl, aryl and aralkyl; and m=0 or 1. Optical isomers of the compound of formula (IX) are also contemplated. In certain embodiments regarding the compound of formula (IX), the following provisos apply: when m=0, then $R_{15}$ is —(CH$_2$)$_2$Cl or

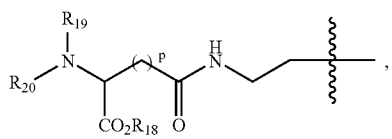

wherein $R_{18}$ is H or a carboxylic acid protecting group; and $R_{19}$ and $R_{20}$ are each independently selected from the group consisting of H, alkyl, aryl and an amine protecting group; and optical isomers thereof. The compound of formula (IX) may, in certain embodiments, be further defined as

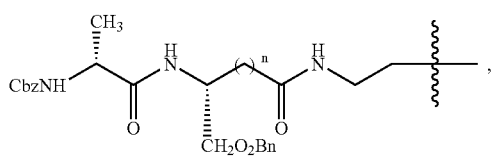

wherein p=2. Regarding the compound of formula (IX), $R_{13}$ may be alkenylalkyl, in certain embodiments. In certain embodiments, $R_{13}$ is —C(H)(OH)-(cyclopropyl-fused-cycloalkenyl). Non-limiting examples of $R_{13}$ groups may be seen in compounds 81-93, shown below. In particular embodiments regarding the compound of formula (IX), m=1. In particular embodiments, the compound of formula (IX) may be further defined as a compound of formula

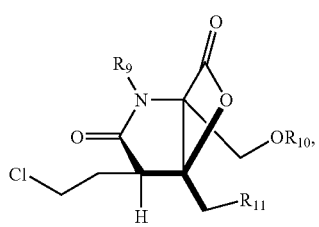

(V)

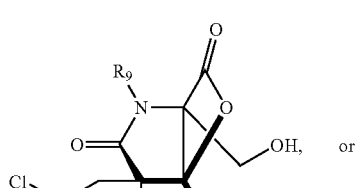

(VI)

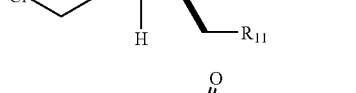

or

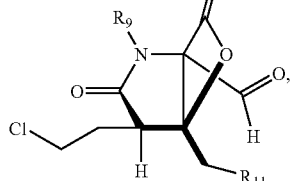

(VII)

wherein $R_9$ is H or an amine protecting group; $R_{10}$ is H or a hydroxy protecting group; and $R_{11}$ is H, OBn, OPMB or ODMB. In particular embodiments regarding compounds of formula (V), (VI) and/or (VII), $R_9$ is selected from the group consisting of p-methoxybenzyl, 3,4-dimethoxybenzyl, p-toluenesulfonamide and $R_{12}OC(O)$—, wherein $R_{12}$ is benzyl, trimethylsilylethyl, or allyl. Certain compounds of formula (IX) that are also contemplated may be selected from the group consisting of compounds 81-93;

81

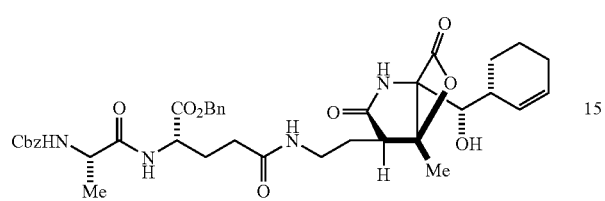

N-Cbz-Ala, OBn-Glu Salino A

82

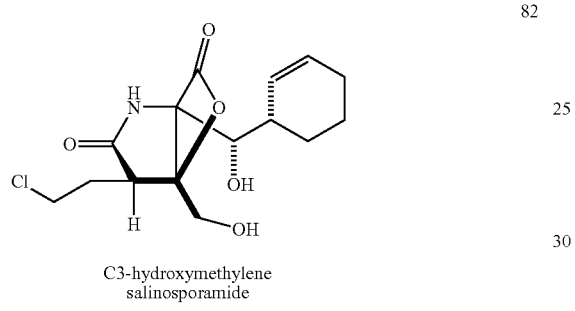

C3-hydroxymethylene salinosporamide

83

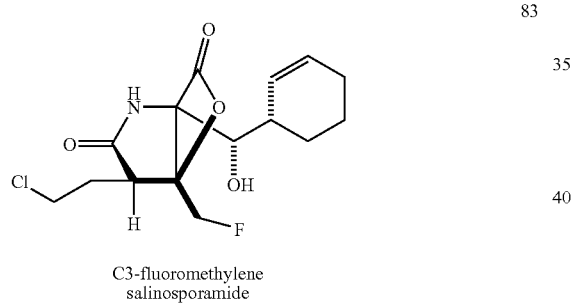

C3-fluoromethylene salinosporamide

84

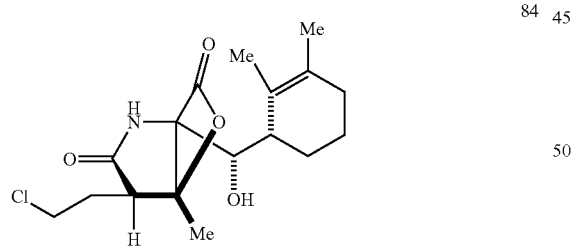

85

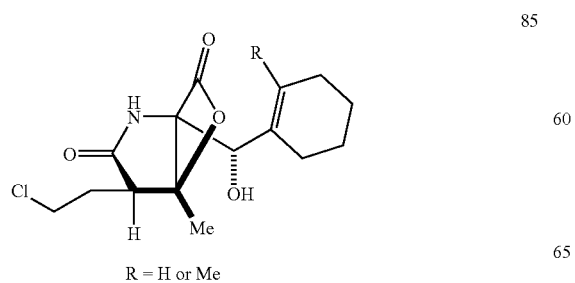

R = H or Me 85.5

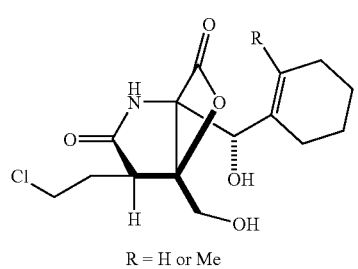

R = H or Me

86

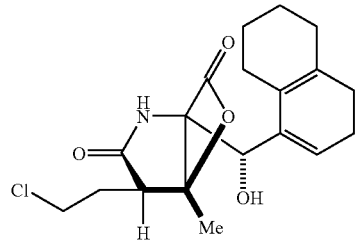

87

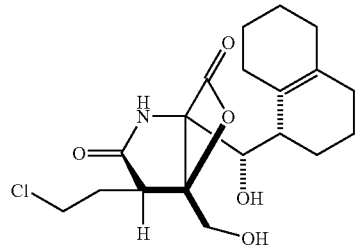

88

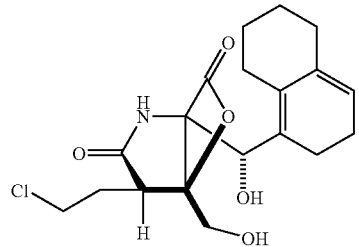

89

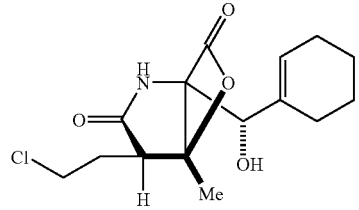

90

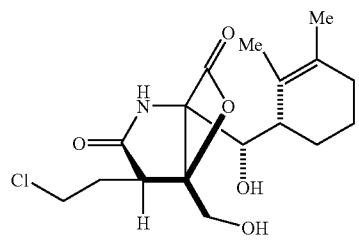

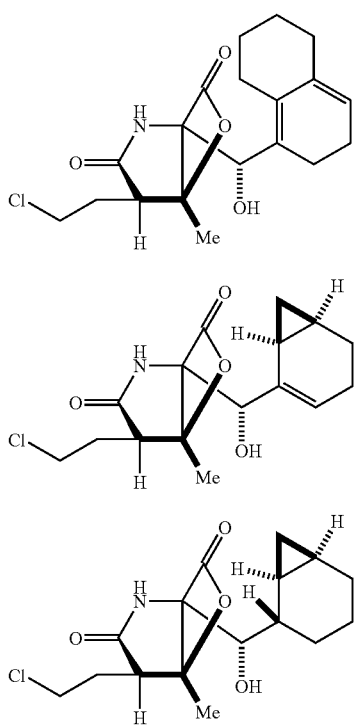

Any compound as described herein, such as the compound of formula (IX), may be comprised in a pharmaceutically acceptable excipient, diluent, or vehicle, as described herein. Any compound as described herein, such as a compound of formula (IX), may further be defined as a prodrug.

Certain aspects of the present invention contemplate a method of inhibiting the 20S proteasome, comprising contacting a cell with an effective amount of a compound as described herein. One skilled in the art can purify and measure the activity of the proteasome using approaches such as those described in the following citations: Hirano et al., 2005; Akaishi et al., 1996; Ugai et al., 1993; Adams et al., 1999; and Mellgren, 1997, each of which is incorporated herein by reference in its entirety. The method may take place in vitro or in vivo. Compounds of the present invention may also be used to treat proteasome-related conditions, such as cancer, Alzheimer's disease, malaria, tuberculosis, eye disorders and asthma. Accordingly, methods of treatment of these conditions are also contemplated. Compounds used in these methods may be comprised in a pharmaceutically acceptable excipient, diluent, or vehicle. In certain embodiments, one or more of compounds 81-93, shown above, may inhibit the 20S proteasome.

Certain aspects of the present invention contemplate a method of inhibiting fatty acid synthase, comprising contacting a cell with an effective amount of a compound as described herein. For example, compounds may be screened for their ability to inhibit the thioesterase domain of fatty acid synthase, which liberates palmitate, the natural substrate, from the enzyme. One of ordinary skill in the art could express and purify the recombinant thioesterase using procedures described in, e.g., Chakravarty et al., 2004 and Kridel et al., 2004 (each of these references are specifically incorporated herein). In this study the thioesterase domain of fatty acid synthase was PCR amplified using the following primers: 5_ATG ACG CCC AAG GAG GAT GGT CTG GCC CAG CAG (SEQ ID NO:1) (corresponds to nucleotides 6727-6756) and 3_GCC CTC CCG CAC GCT CAC GCG TGG CT (SEQ ID NO:2) (corresponds to nucleotides 7625-7650). The recombinant thioesterase domain was cloned into pTrcHis (Invitrogen) and expressed in *Escheria coli*. The recombinant protein corresponds to residues 2202 through 2509 of FAS. The thioesterase was purified by Ni-affinity chromatography. The method may take place in vitro or in vivo. Compounds of the present invention may also be used to treat fatty acid-synthase-related conditions, which generally includes diseases characterized by hyperproliferation of cells such as inflammation, angiogenesis and cancer. Such compounds may also be of use in treating obesity as fatty acid synthase is the only enzyme that converts dietary carbohydrate to fat. Accordingly, methods of treatment of these conditions are also contemplated. Compounds used in these methods may be comprised in a pharmaceutically acceptable excipient, diluent, or vehicle. The inhibition of fatty acid synthase in cells can be measured by, for example, directly determining the amount of palmitate synthesized by the cell using methods described in Browne et al., 2006, Kridel et al., 2004 and Pizer et al., 1996 (each of these references are specifically incorporated herein).

Another general aspect of the present invention contemplates a method of treating cancer comprising administering to a subject an effective amount of a compound as described herein. The subject may be a mammal, such as a human. The cancer may be any cancer treatable by administration of a compound described herein. For example, the cancer may be breast, prostate, ovarian, brain hepatocarcinoma, melanoma, colorectal, liver, lymphoma, lung, oral, head, neck, spleen, lymph node, small intestine, large intestine, blood cells, stomach, endometrium, testicle, skin, esophagus, bone marrow, blood, cervical, bladder, Ewing's sarcoma, thyroid, and/or gastrointestinal.

The terms "inhibiting," "reducing," or "prevention," or any variation of these terms, when used in the claims and/or the specification includes any measurable decrease or complete inhibition to achieve a desired result.

The term "contact," when applied to a cell, is used herein to describe the process by which a compound of the invention is delivered to a target cell or is placed in direct juxtaposition with the target cell.

As used herein, the term "effective" (e.g., "an effective amount") means adequate to accomplish a desired, expected, or intended result. For example, an "effective amount" may be an amount of a compound sufficient to produce a therapeutic benefit (e.g., effective to reproducibly inhibit decrease, reduce, inhibit or otherwise abrogate the growth of a cancer cell). "Effective amounts" or a "therapeutically relevant amount" are those amounts of a compound sufficient to produce a therapeutic benefit (e.g., effective to reproducibly inhibit decrease, reduce, inhibit or otherwise abrogate the growth of a cancer cell). An effective amount, in the context of treating a subject, is sufficient to produce a therapeutic benefit. The term "therapeutic benefit" as used herein refers to anything that promotes or enhances the well-being of the subject with respect to the medical treatment of the subject's condition.

Persons of ordinary skill in the art will be familiar with synthetic methods that can be used to manipulate compounds of the present invention to arrive at natural products, including natural products of therapeutic value, as well as other derivatives of the claimed compounds. These methods include preserving the cyclic beta-lactone moiety generated using the method of the present invention as well as the "opening" of the cyclic beta-lactone once it has been generated by the method of the present invention. At least three non-limiting examples of these manipulations are shown herein, including syntheses of salinosporamide, the Bayer compound, and dihydroplakevulin A.

A person of ordinary skill in the art will recognize that chemical modifications can be made to the compounds of the present invention, as well as compounds employed in the method of the present invention, without departing from the spirit and scope of the present invention. Substitutes, derivatives, or equivalents can also be used, all of which are contemplated as being part of the present invention.

Ratios of reagents/substrates may be varied as needed, depending on the nature of the carbonyl/carboxylic acid difunctionalized amide, activating agent, base and/or nucleophilic promoter used. The minimization of waste of substrates/reagents is also desirable. As envisioned in the present invention, equivalents of the carbonyl-carboxylic acid-containing compound, activating agent, base, and nucleophilic promoter may, in certain embodiments, range from about 0 to about 10 or more, with about 0.1 to about 6 equivalents being preferred, and about 0.5 to about 4 equivalents being even more preferred. In some preferred embodiments, equivalents of the activating agent will range from about 1 to about 4 equivalents, equivalents of the base will range from about 0 to about 5 equivalents, and equivalents of the nucleophilic promoter will range from about 0.5 to about 5 equivalents. In certain embodiments, the ratio of carbonyl/carboxylic acid difunctionalized amide to activating agent to nucleophilic promoter may be about 1:1:1 (that is, about 1 to about 1 to about 1), about 1:1.5:1, about 1:1:1.5, about 1:1.5:1.5, about 1:1:2, about 1:2:1, or about 1:2:2. In certain embodiments, the equivalents are as follows: carbonyl/carboxylic acid difunctionalized amide (about 1 equiv); activating agent (about 1.5 equiv); and nucleophilic promoter (about 1.5 equiv).

Reaction conditions for the formation of the lactam-fused beta lactone component of the compounds described herein will typically comprise a suitable solvent and reactions typically take place between about 0-50° C., such as about 0-25° C., or about 0-10° C., and last from about 0.5-48 hrs or more, such as 1-24 hrs, 12-24 hrs, or 24-28 hrs, or any other range derivable in 0.5-48 hrs. Solvent choices for the methods of the present invention will be known to one of ordinary skill in the art. Solvent choices may depend, for example, on which one(s) will facilitate the solubilizing of all the reagents, or, for example, which one(s) will best facilitate the desired reaction (particularly if the mechanism of the reaction is known). As used herein, a "suitable solvent" is a solvent that will facilitate, or at least not significantly impede, the reaction that takes place within that solvent. Solvents may include, for example, polar solvents and non-polar solvents. Solvents choices include, but are not limited to, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. In preferred embodiments, solvents include methylene chloride and acetonitrile.

Persons of ordinary skill in the art will be familiar with methods of purifying compounds of the present invention. Purification of every compound of the present invention is generally possible, including the purification of intermediates as well as purification of the final products. The purification step is not always included in the general methodologies explained below, but one of ordinary skill in the art will understand that compounds can generally be purified at any step. Examples of purification methods include gel filtration, size exclusion chromatography (also called gel filtration chromatography, gel permeation chromatography or molecular exclusion), dialysis, distillation, recrystallization, sublimation, electrophoresis, silica gel column chromatography (also known as flash chromatography) and high-performance liquid chromatography (HPLC), including normal-phase HPLC and reverse-phase HPLC. Purification of compounds via silica gel column chromatography or HPLC, for example, offer the benefit of yielding desired compounds in very high purity, often higher than when compounds are purified via other methods. In some embodiments, the preferred means of purification is flash chromatography.

Methods of determining the purity of compounds are well known to those of skill in the art and include, in non-limiting examples, autoradiography, mass spectroscopy, melting point determination, ultra violet analysis, colorimetric analysis, (HPLC), thin-layer chromatography and nuclear magnetic resonance (NMR) analysis (including, but not limited to, $^1$H and $^{13}$C NMR). Software available on varying instruments (e.g., spectrophotometers, HPLCs, NMRs) can aid one of skill in the art in making these determinations, as well as other means known to those of skill in the art.

In certain embodiments of the present invention, purification of a compound does not remove all impurities. In some embodiments, such impurities can be identified.

It is contemplated that any embodiment discussed in this specification can be implemented with respect to any method, compound or composition of the invention, and vice versa. Furthermore, compounds and compositions of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. For example, "about" can be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF THE DRAWING

The foregoing aspects and many of the attendant advantages of this invention will become more readily appreciated as the same become better understood by reference to the following detailed description, when taken in conjunction with the accompanying drawing, wherein the figure represents an HPLC analysis of β-lactones following bis-cyclization (column type: Chiralcel® OD; 10% to 25% i-PrOH in hexane).

DESCRIPTION OF ILLUSTRATIVE EMBODIMENTS

The present invention overcomes the deficiencies of the prior art by providing a method that enables facile access to heterocyclic fused beta-lactones that are otherwise more difficult to generate using other methods. Since heterocyclic-fused beta-lactones are found in many natural products of therapeutic interest, this method and the compounds synthesized by this method enables access to a variety of compounds that act as intermediates to these natural products, as well as direct access to the compounds themselves. Compounds synthesized by the present invention may also be used for therapeutic purposes.

A. Chemical Definitions

As used herein, a "carbonyl/carboxylic acid difunctionalized amide" refers to any compound that contains both a carbonyl (that is, a ketone or aldehyde) and a carboxylic acid (—COOH) group. In certain embodiments, a carbonyl/carboxylic acid difunctionalized amide may be further defined as an alpha-amino acid that bears either a substituted N-beta-keto acyl group, substituted N-beta-aldehyde acyl group, substituted N-gamma-keto-acyl group, or substituted N-gamma-aldehyde acyl group.

As used herein, an "activating agent" refers to a reagent that is able to activate a carboxylic acid such that it undergoes nucleophilic substitution (addition/elimination) under mild conditions.

As used herein, a "nucleophilic promoter" refers to a nucleophilic species (e.g., a Lewis base) that undergoes nucleophilic substitution at an activated carboxylic acid and promotes the formation of an acyl ammonium followed by deprotonation, leading to an ammonium enolate and finally leading to a nucleophile catalyzed aldol-lactonization or bis-cyclization process. In certain embodiments, a pendant ketone or aldehyde results.

The term "nucleophile" or "nucleophilic" generally refers to atoms bearing lone pairs of electrons. Such terms are well known in the art and include —NH$_2$, thiolate, carbanion, and alcoholate (also known as hydroxyl).

As used herein, a "chiral auxiliary" refers to an easily removable chiral group that is capable of influencing the direction of nucleophilic attack. Chiral auxiliaries typically control the diastereoselectivity of a reaction. Persons of skill in the art are familiar with such compounds, and many are commercially available.

As used herein, the term "amino" means —NH$_2$; the term "nitro" means —NO$_2$; the term "halo" designates —F, —Cl, —Br or —I; the term "mercapto" means —SH; the term "cyano" means —CN; the term "azido" means —N$_3$; the term "silyl" means —SiH$_3$; the term "sulfonyl" means —SO$_2$H; "triflate" means —OSO$_2$CF$_3$; and the term "hydroxy" means —OH.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted C$_n$-alkyl, and heteroatom-substituted C$_n$-alkyl. In certain embodiments, lower alkyls are contemplated. The term "lower alkyl" refers to alkyls of 1-6 carbon atoms (that is, 1, 2, 3, 4, 5 or 6 carbon atoms). The term "heteroatom-unsubstituted C$_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted C$_1$-C$_{10}$-alkyl has 1 to 10 carbon atoms. The groups —CH$_3$ (Me), —CH$_2$CH$_3$ (Et), —CH$_2$CH$_2$CH$_3$ (n-Pr), —CH(CH$_3$)$_2$ (iso-Pr), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), and

are all non-limiting examples of heteroatom-unsubstituted alkyl groups. The term "heteroatom-substituted C$_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted C$_1$-C$_{10}$-alkyl has 1 to 10 carbon atoms. The following groups are all non-limiting examples of heteroatom-substituted alkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, —C(=N—OH)CH(CH$_3$)$_2$ and —CH$_2$Si(CH$_3$)$_3$.

The term "alkenyl" includes straight-chain alkenyl, branched-chain alkenyl, cycloalkenyl, cyclic alkenyl, heteroatom-unsubstituted alkenyl, heteroatom-substituted alkenyl, heteroatom-unsubstituted C$_n$-alkenyl, and heteroatom-substituted C$_n$-alkenyl. In certain embodiments, lower alkenyls are contemplated. The term "lower alkenyl" refers to alkenyls of 1-6 carbon atoms (that is, 1, 2, 3, 4, 5 or 6 carbon atoms). The term "heteroatom-unsubstituted C$_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted C$_2$-C$_{10}$-alkenyl has 2 to 10 carbon atoms. Heteroatom-unsubstituted alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, —CH=CH—C$_6$H$_5$ and cycloalkyls fused to cycloalkenyls (e.g.,

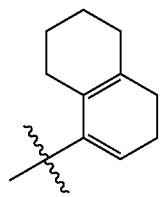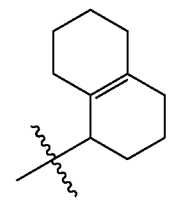 and

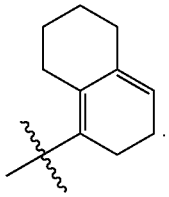

The term "heteroatom-substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —CH═CHF, —CH═CHCl and —CH═CHBr, are non-limiting examples of heteroatom-substituted alkenyl groups.

The term "alkynyl" includes straight-chain alkynyl, branched-chain alkynyl, cycloalkynyl, cyclic alkynyl, heteroatom-unsubstituted alkynyl, heteroatom-substituted alkynyl, heteroatom-unsubstituted $C_n$-alkynyl, and heteroatom-substituted $C_n$-alkynyl. In certain embodiments, lower alkynyls are contemplated. The term "lower alkynyl" refers to alkynyls of 1-6 carbon atoms (that is, 1, 2, 3, 4, 5 or 6 carbon atoms). The term "heteroatom-unsubstituted $C_n$-alkynyl" refers to a radical, having a linear or branched, cyclic or acyclic structure, further having at least one carbon-carbon triple bond, a total of n carbon atoms, at least one hydrogen atom, and no heteroatoms. For example, a heteroatom-unsubstituted $C_2$-$C_{10}$-alkynyl has 2 to 10 carbon atoms. The groups, —C≡CH, —C≡CCH$_3$, and —C≡CC$_6$H$_5$ are non-limiting examples of heteroatom-unsubstituted alkynyl groups. The term "heteroatom-substituted $C_n$-alkynyl" refers to a radical, having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkynyl has 2 to 10 carbon atoms. The group, —C≡CSi(CH$_3$)$_3$, is a non-limiting example of a heteroatom-substituted alkynyl group.

The term "aryl" includes heteroatom-unsubstituted aryl, heteroatom-substituted aryl, heteroatom-unsubstituted $C_n$-aryl, heteroatom-substituted $C_n$-aryl, heteroaryl, heterocyclic aryl groups, carbocyclic aryl groups, biaryl groups, and radicals derived from polycyclic fused hydrocarbons (PAHs). The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Non-limiting examples of heteroatom-unsubstituted aryl groups include methylphenyl, (dimethyl)phenyl, —C$_6$H$_4$—CH$_2$CH$_3$, —C$_6$H$_4$—CH$_2$CH$_2$CH$_3$, —C$_6$H$_4$—CH(CH$_3$)$_2$, —C$_6$H$_4$—CH(CH$_2$)$_2$, —C$_6$H$_3$(CH$_3$) CH$_2$CH$_3$, —C$_6$H$_4$—CH═CH$_2$, —C$_6$H$_4$—CH═CHCH$_3$, —C$_6$H$_4$C≡CH, —C$_6$H$_4$C≡CCH$_3$, naphthyl, and the radical derived from biphenyl. The term "heteroatom-substituted $C_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. Non-limiting examples of heteroatom-substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$—CH$_2$OH, —C$_6$H$_4$—CH$_2$OC(O)CH$_3$, —C$_6$H$_4$—CH$_2$NH$_2$, —C$_6$H$_4$CF$_3$, —C$_6$H$_4$CN, —C$_6$H$_4$—CHO, —C$_6$H$_4$—CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, —C$_6$H$_4$CON(CH$_3$)$_2$, furanyl, thienyl, pyridyl, pyrrolyl, pyrimidyl, pyrazinyl, indolyl, quinolyl, and imidazoyl.

The term "aralkyl" includes heteroatom-unsubstituted aralkyl, heteroatom-substituted aralkyl, heteroatom-unsubstituted $C_n$-aralkyl, heteroatom-substituted $C_n$-aralkyl, heteroaralkyl, and heterocyclic aralkyl groups. In certain embodiments, lower aralkyls are contemplated. Aralkyls generally refer to radicals comprising the formula -alkyl-aryl. The term "lower aralkyl" refers to aralkyls of 7-12 carbon atoms (that is, 7, 8, 9, 10, 11 or 12 carbon atoms). The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{11}$-aralkyl has 7 to 11 carbon atoms. Non-limiting examples of heteroatom-unsubstituted aralkyls are: 2,3-dihydro-1H-indenyl, 1,2,3,4-tetrahydronaphthalenyl, phenylmethyl (benzyl, Bn) and phenylethyl. The term "heteroatom-substituted $C_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms. Examples of heteroatom-substituted $C_n$-aralkyls include indolinyl, benzofuranyl and benzothiophenyl.

The term "acyl" includes straight-chain acyl, branched-chain acyl, cycloacyl, cyclic acyl, heteroatom-unsubstituted acyl, heteroatom-substituted acyl, heteroatom-unsubstituted $C_n$-acyl, heteroatom-substituted $C_n$-acyl, alkylcarbonyl, alkoxycarbonyl and aminocarbonyl groups. In certain embodiments, lower acyls are contemplated. The term "lower acyl" refers to acyls of 1-6 carbon atoms (that is, 1, 2, 3, 4, 5 or 6 carbon atoms). The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —CHO, —C(O)CH$_3$, —C(O) CH$_2$CH$_3$, —C(O)CH$_2$CH$_2$CH$_3$, —C(O)CH(CH$_3$)$_2$, —C(O) CH(CH$_2$)$_2$, —C(O)C$_6$H$_5$, —C(O)C$_6$H$_4$—CH$_3$, —C(O) C$_6$H$_4$—CH$_2$CH$_3$, and —COC$_6$H$_3$(CH$_3$)$_2$, are non-limiting examples of heteroatom-unsubstituted acyl groups. The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom, in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The groups, —C(O)CH$_2$CF$_3$, —CO$_2$H, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(C$_1$H$_3$)$_2$, —CONHCH(CH$_2$)$_2$, —CON(CH$_3$)$_2$, and —CONHCH$_2$CF$_3$, are non-limiting examples of heteroatom-substituted acyl groups.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted $C_n$-alkoxy, and heteroatom-substituted $C_n$-alkoxy. In certain embodiments, lower alkoxys are contemplated. The term "lower alkoxy" refers to alkoxys of 1-6 carbon atoms (that is, 1, 2, 3, 4, 5 or 6 carbon atoms). The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$. The term "heteroatom-substituted $C_n$-alkoxy" refers to a group, having the structure —OR, in which R is a heteroatom-substituted $C_n$-alkyl, as that term is defined above. For example, —OCH$_2$CF$_3$ is a heteroatom-substituted alkoxy group.

The term "alkenyloxy" includes straight-chain alkenyloxy, branched-chain alkenyloxy, cycloalkenyloxy, cyclic alkenyloxy, heteroatom-unsubstituted alkenyloxy, heteroatom-substituted alkenyloxy, heteroatom-unsubstituted $C_n$-alkenyloxy, and heteroatom-substituted $C_n$-alkenyloxy. In certain embodiments, lower alkenyloxys are contemplated. The term "lower alkenyloxy" refers to alkenyloxys of 1-6 carbon atoms (that is, 1, 2, 3, 4, 5 or 6 carbon atoms). The term "heteroatom-unsubstituted $C_n$-alkenyloxy" refers to a group, having the structure —OR, in which R is a heteroatom-unsubstituted $C_n$-alkenyl, as that term is defined above. The term "heteroatom-substituted $C_n$-alkenyloxy" refers to a group, having the structure —OR, in which R is a heteroatom-substituted $C_n$-alkenyl, as that term is defined above.

The term "alkynyloxy" includes straight-chain alkynyloxy, branched-chain alkynyloxy, cycloalkynyloxy, cyclic alkynyloxy, heteroatom-unsubstituted alkynyloxy, heteroatom-substituted alkynyloxy, heteroatom-unsubstituted $C_n$-alkynyloxy, and heteroatom-substituted $C_n$-alkynyloxy. In certain embodiments, lower alkynyloxys are contemplated. The term "lower alkynyloxy" refers to alkynyloxys of 1-6 carbon atoms (that is, 1, 2, 3, 4, 5 or 6 carbon atoms). The term "heteroatom-unsubstituted $C_n$-alkynyloxy" refers to a group, having the structure —OR, in which R is a heteroatom-unsubstituted $C_n$-alkynyl, as that term is defined above. The term "heteroatom-substituted $C_n$-alkynyloxy" refers to a group, having the structure —OR, in which R is a heteroatom-substituted $C_n$-alkynyl, as that term is defined above.

The term "aryloxy" includes heteroatom-unsubstituted aryloxy, heteroatom-substituted aryloxy, heteroatom-unsubstituted $C_n$-aryloxy, heteroatom-substituted $C_n$-aryloxy, heteroaryloxy, and heterocyclic aryloxy groups. The term "heteroatom-unsubstituted $C_n$-aryloxy" refers to a group, having the structure —OAr, in which Ar is a heteroatom-unsubstituted $C_n$-aryl, as that term is defined above. A non-limiting example of a heteroatom-unsubstituted aryloxy group is —OC$_6$H$_5$. The term "heteroatom-substituted $C_n$-aryloxy" refers to a group, having the structure —OAr, in which Ar is a heteroatom-substituted $C_n$-aryl, as that term is defined above.

The term "aralkyloxy" includes heteroatom-unsubstituted aralkyloxy, heteroatom-substituted aralkyloxy, heteroatom-unsubstituted $C_n$-aralkyloxy, heteroatom-substituted $C_n$-aralkyloxy, heteroaralkyloxy, and heterocyclic aralkyloxy groups. In certain embodiments, lower aralkyloxys are contemplated. The term "lower aralkyloxy" refers to alkenyloxys of 7-12 carbon atoms (that is, 7, 8, 9, 10, 11, or 12 carbon atoms). The term "heteroatom-unsubstituted $C_n$-aralkyloxy" refers to a group, having the structure —OAr, in which Ar is a heteroatom-unsubstituted $C_n$-aralkyl, as that term is defined above. The term "heteroatom-substituted $C_n$-aralkyloxy" refers to a group, having the structure —OAr, in which Ar is a heteroatom-substituted $C_n$-aralkyl, as that term is defined above.

The term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted $C_n$-acyloxy, heteroatom-substituted $C_n$-acyloxy, alkylcarbonyloxy, arylcarbonyloxy, alkoxycarbonyloxy, aryloxycarbonyloxy, and carboxylate groups. In certain embodiments, lower acyloxys are contemplated. The term "lower acyloxy" refers to acyloxys of 1-6 carbon atoms (that is, 1, 2, 3, 4, 5 or 6 carbon atoms). The term "heteroatom-unsubstituted $C_n$-acyloxy" refers to a group, having the structure —OAc, in which Ac is a heteroatom-unsubstituted $C_n$-acyl, as that term is defined above. For example, —OC(O)CH$_3$ is a non-limiting example of a heteroatom-unsubstituted acyloxy group. The term "heteroatom-substituted $C_n$-acyloxy" refers to a group, having the structure —OAc, in which Ac is a heteroatom-substituted $C_n$-acyl, as that term is defined above. For example, —OC(O)OCH$_3$, —OC(O)NHCH$_3$ and —OC(O)-benzophenone are non-limiting examples of heteroatom-unsubstituted acyloxy groups.

The term "alkylamino" includes straight-chain alkylamino, branched-chain alkylamino, cycloalkylamino, cyclic alkylamino, heteroatom-unsubstituted alkylamino, heteroatom-substituted alkylamino, heteroatom-unsubstituted $C_n$-alkylamino, and heteroatom-substituted $C_n$-alkylamino. In certain embodiments, lower alkylaminos are contemplated. The term "lower alkylamino" refers to alkylaminos of 1-6 carbon atoms (that is, 1, 2, 3, 4, 5 or 6 carbon atoms). The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl. The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "alkenylamino" includes straight-chain alkenylamino, branched-chain alkenylamino, cycloalkenylamino, cyclic alkenylamino, heteroatom-unsubstituted alkenylamino, heteroatom-substituted alkenylamino, heteroatom-unsubstituted Cfl-alkenylamino, heteroatom-substituted $C_n$-alkenylamino, dialkenylamino, and alkyl(alkenyl)amino groups. In certain embodiments, lower alkenylaminos are contemplated. The term "lower alkenylamino" refers to alkenylaminos of 1-6 carbon atoms (that is, 1, 2, 3, 4, 5 or 6 carbon atoms). The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. The term "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "alkynylamino" includes straight-chain alkynylamino, branched-chain alkynylamino, cycloalkynylamino, cyclic alkynylamino, heteroatom-unsubstituted alkynylamino, heteroatom-substituted alkynylamino, heteroatom-unsubstituted $C_n$-alkynylamino, heteroatom-substituted $C_n$-alkynylamino, dialkynylamino, alkyl(alkynyl)amino, and alkenyl(alkynyl)amino groups. In certain embodiments, lower alkynylaminos are contemplated. The term "lower alkynylamino" refers to alkynylaminos of 1-6 carbon atoms (that is, 1, 2, 3, 4, 5 or 6 carbon atoms). The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "arylamino" includes heteroatom-unsubstituted arylamino, heteroatom-substituted arylamino, heteroatom-unsubstituted $C_n$-arylamino, heteroatom-substituted $C_n$-arylamino, heteroarylamino, heterocyclic arylamino, and alkyl (aryl)amino groups. The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above.

The term "aralkylamino" includes heteroatom-unsubstituted aralkylamino, heteroatom-substituted aralkylamino, heteroatom-unsubstituted $C_n$-aralkylamino, heteroatom-substituted $C_n$-aralkylamino, heteroaralkylamino, heterocyclic aralkylamino groups, and diaralkylamino groups. In certain embodiments, lower aralkylaminos are contemplated. The term "lower aralkylamino" refers to aralkylaminos of 7-12 carbon atoms (that is, 7, 8, 9, 10, 11, or 12 carbon atoms). The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above.

The term "amido" includes straight-chain amido, branched-chain amido, cycloamido, cyclic amido, heteroatom-unsubstituted amido, heteroatom-substituted amido, heteroatom-unsubstituted $C_n$-amido, heteroatom-substituted $C_n$-amido, alkylcarbonylamino, arylcarbonylamino, alkoxycarbonylamino, aryloxycarbonylamino, acylamino, alkylaminocarbonylamino, arylaminocarbonylamino, and ureido groups. The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The group, —NHC(O)CH$_3$, is a non-limiting example of a heteroatom-unsubstituted amido group. The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is a non-limiting example of a heteroatom-substituted amido group.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted $C_n$-alkylthio, and heteroatom-substituted $C_n$-alkylthio. In certain embodiments, lower alkylthios are contemplated. The term "lower alkylthio" refers to alkylthios of 1-6 carbon atoms (that is, 1, 2, 3, 4, 5 or 6 carbon atoms). The term "heteroatom-unsubstituted $C_n$-alkylthio" refers to a group, having the structure —SR, in which R is a heteroatom-unsubstituted $C_n$-alkyl, as that term is defined above. The group, —SCH$_3$, is an example of a heteroatom-unsubstituted alkylthio group. The term "heteroatom-substituted $C_n$-alkylthio" refers to a group, having the structure —SR, in which R is a heteroatom-substituted $C_n$-alkyl, as that term is defined above.

The term "alkenylthio" includes straight-chain alkenylthio, branched-chain alkenylthio, cycloalkenylthio, cyclic alkenylthio, heteroatom-unsubstituted alkenylthio, heteroatom-substituted alkenylthio, heteroatom-unsubstituted $C_n$-alkenylthio, and heteroatom-substituted $C_n$-alkenylthio. In certain embodiments, lower alkenylthios are contemplated. The term "lower alkenylthio" refers to alkenylthios of 1-6 carbon atoms (that is, 1, 2, 3, 4, 5 or 6 carbon atoms). The term "heteroatom-unsubstituted $C_n$-alkenylthio" refers to a group, having the structure —SR, in which R is a heteroatom-unsubstituted $C_n$-alkenyl, as that term is defined above. The term "heteroatom-substituted $C_n$-alkenylthio" refers to a group, having the structure —SR, in which R is a heteroatom-substituted $C_n$-alkenyl, as that term is defined above.

The term "alkynylthio" includes straight-chain alkynylthio, branched-chain alkynylthio, cycloalkynylthio, cyclic alkynylthio, heteroatom-unsubstituted alkynylthio, heteroatom-substituted alkynylthio, heteroatom-unsubstituted $C_n$-alkynylthio, and heteroatom-substituted $C_n$-alkynylthio. In certain embodiments, lower alkynylthios are contemplated. The term "lower alkynylthio" refers to alkynylthios of 1-6 carbon atoms (that is, 1, 2, 3, 4, 5 or 6 carbon atoms). The term "heteroatom-unsubstituted $C_n$-alkynylthio" refers to a group, having the structure —SR, in which R is a heteroatom-unsubstituted $C_n$-alkynyl, as that term is defined above. The term "heteroatom-substituted $C_n$-alkynylthio" refers to a group, having the structure —SR, in which R is a heteroatom-substituted $C_n$-alkynyl, as that term is defined above.

The term "arylthio" includes heteroatom-unsubstituted arylthio, heteroatom-substituted arylthio, heteroatom-unsubstituted $C_n$-arylthio, heteroatom-substituted $C_n$-arylthio, heteroarylthio, and heterocyclic arylthio groups. The term "heteroatom-unsubstituted $C_n$-arylthio" refers to a group, having the structure —SAr, in which Ar is a heteroatom-unsubstituted $C_n$-aryl, as that term is defined above. The group, —SC$_6$H$_5$, is an example of a heteroatom-unsubstituted arylthio group. The term "heteroatom-substituted $C_n$-arylthio" refers to a group, having the structure —SAr, in which Ar is a heteroatom-substituted $C_n$-aryl, as that term is defined above.

The term "aralkylthio" includes heteroatom-unsubstituted aralkylthio, heteroatom-substituted aralkylthio, heteroatom-unsubstituted $C_n$-aralkylthio, heteroatom-substituted $C_n$-aralkylthio, heteroaralkylthio, and heterocyclic aralkylthio groups. In certain embodiments, lower aralkylthios are contemplated. The term "lower aralkylthio" refers to aralkylthios of 7-12 carbon atoms (that is, 7, 8, 9, 10, 11, or 12 carbon atoms). The term "heteroatom-unsubstituted $C_n$-aralkylthio" refers to a group, having the structure —SAr, in which Ar is a heteroatom-unsubstituted $C_n$-aralkyl, as that term is defined above. The group, —SCH$_2$C$_6$H$_5$, is an example of a heteroatom-unsubstituted aralkyl group. The term "heteroatom-substituted $C_n$-aralkylthio" refers to a group, having the structure —SAr, in which Ar is a heteroatom-substituted $C_n$-aralkyl, as that term is defined above.

The term "acylthio" includes straight-chain acylthio, branched-chain acylthio, cycloacylthio, cyclic acylthio, heteroatom-unsubstituted acylthio, heteroatom-substituted acylthio, heteroatom-unsubstituted $C_n$-acylthio, heteroatom-substituted $C_n$-acylthio, alkylcarbonyloxy, arylcarbonyloxy, alkoxycarbonyloxy, aryloxycarbonyloxy, and carboxylate groups. In certain embodiments, lower acylthios are contemplated. The term "lower acylthio" refers to acylthios of 1-6 carbon atoms (that is, 1, 2, 3, 4, 5 or 6 carbon atoms). The term "heteroatom-unsubstituted $C_n$-acylthio" refers to a group, having the structure —SAc, in which Ac is a heteroatom-unsubstituted $C_n$-acyl, as that term is defined above. The group, —SCOCH$_3$, is an example of a heteroatom-unsubstituted acylthio group. The term "heteroatom-substituted $C_n$-acylthio" refers to a group, having the structure —SAc, in which Ac is a heteroatom-substituted $C_n$-acyl, as that term is defined above.

The claimed invention is also intended to encompass salts of any of the compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred as described below, although other salts may be useful, as for example in isolation or purification steps.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphoric acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium and imidazolium.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (P. H. Stahl & C. G. Wermuth eds., Verlag Helvetica Chimica Acta, 2002), which is incorporated herein by reference.

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present invention are contemplated as being within the scope of the present invention. However, in certain aspects, particular diastereomers are contemplated. The chiral centers of the compounds of the present invention can have the S- or the R-configuration, as defined by the IUPAC 1974 Recommendations. In certain aspects, certain compounds of the present invention may comprise S- or R-configurations at particular carbon centers. The present invention is meant to comprehend all such isomeric forms of the compounds of the invention.

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification. Such derivatives may have the addition, removal, or substitution of one or more chemical moieties on the parent molecule. Non-limiting examples of the types modifications that can be made to the compounds and structures disclosed herein include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halo substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom to generate, for example, a heterocycloalkyl structure. A derivative may also be a compound displaying a protecting group, as opposed to the exposed functional group, and vice-versa.

Prodrugs and solvates of the compounds of the present invention are also contemplated herein. Any compound described herein may be a prodrug. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1991; Bundgaard, 1985). Solvates of the compounds of the present invention are preferably hydrates.

As used herein, "predominantly one enantiomer" or "substantially free" from other optical isomers means that the compound contains at least about 95% of one enantiomer, or more preferably at least about 98% of one enantiomer, or most preferably at least about 99% of one enantiomer. Any compound described herein may, in certain embodiments, be present as predominantly one enantiomer.

In certain embodiments, "substantially pure" compounds are contemplated. That is, any compound as described herein may be a substantially pure compound. As used herein, the term "substantially pure" refers to compounds that are at least about 95% pure, or more preferably at least about 98% pure, or most preferably at least about 99% pure.

In view of the above definitions, other chemical terms used throughout this application can be easily understood by those of skill in the art. Terms may be used alone or in any combination thereof. The preferred and more preferred chain lengths of the radicals apply to all such combinations.

When a chemical reaction is to be carried out selectively at one reactive site in a multifunctional compound, other reactive sites must be temporarily blocked. A "protecting group," "protected carboxylic acid," "protected amine," or "protected hydroxy," etc., as used herein, is defined as a group used for the purpose of this temporary blockage. During the synthesis of the compounds of the present invention, various functional groups must be protected using protecting groups (or protecting agents) at various stages of the synthesis. However, use of the phrase "protected hydroxy" or "protected amine" and the like does not mean that every functional group available to be protected is protected.

Compounds of the present invention, including compounds used and made during the practice of the method of the present invention, are contemplated both in protected and unprotected form. Persons of ordinary skill in the art will understand that functional groups necessary for the desired transformation should be unprotected.

There are a number of methods well known to those skilled in the art for accomplishing such a step. For protecting agents, their reactivity, installation and use, see, e.g., "Protective Groups in Organic Synthesis" (1999), herein incorporated by reference in its entirety. The function of a protecting group is to protect one or more functionalities (e.g., $-NH_2$, $-SH$, $-COOH$) during subsequent reactions which would not proceed well, either because the free (in other words, unprotected) functional group would react and be functionalized in a way that is inconsistent with its need to be free for subsequent reactions, or the free functional group would interfere in the reaction. The same protecting group may be used to protect one or more of the same or different functional group(s).

When a protecting group is no longer needed, it is removed by methods well known to those skilled in the art. For deprotecting agents and their use, see, e.g., "Protective Groups in Organic Synthesis" (1999). Agents used to remove the protecting group are called deprotecting agents. Protecting groups are typically readily removable (as is known to those skilled in the art) by methods employing deprotecting agents that are well known to those skilled in the art. It is well known that certain deprotecting agents remove some protective groups and not others, while other deprotecting agents remove several types of protecting groups from several types of functional groups. Thus, a first deprotecting agent may be used to remove one type of protecting group, followed by the use of a second deprotecting agent to remove a second type of protecting group, and so on.

In one embodiment of the present invention, the deprotecting agent is hydrofluoric acid in pyridine to remove a TBS (t-butyldimethylsilyl) protecting group to reveal a free hydroxy group. Persons of ordinary skill in the art will be familiar with the proper ordering of protective group removal using deprotecting agents. See e.g., "Protective Groups in Organic Synthesis" (1999). Particular non-limiting examples of protecting groups are discussed below.

Amino protecting groups are well known to those skilled in the art. See, for example, "Protective Groups in Organic Synthesis" (1999), Chapter 7. The amino protecting group may be a carbamate. In some embodiments, amino protecting group may be selected from the group consisting of t-butoxycarbonyl, benzyloxycarbonyl, formyl, trityl, acetyl, trichloroacetyl, dichloroacetyl, chloroacetyl, trifluoroacetyl, difluoroacetyl, fluoroacetyl, benzyl chloroformate, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluoyl)prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluoylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and 9-fluorenylmethyl carbonate. In some preferred embodiments, the amino protecting group is selected from the group consisting of p-methoxybenzyl, benzyloxymethyl and p-toluene sulfonyl.

Thiol protecting groups are well known to those skilled in the art. See, for example, "Protective Groups in Organic Synthesis" (1999), Chapter 6. In some embodiments, a thiol protecting group may be selected from the group consisting of acetamidomethyl, benzamidomethyl, 1-ethoxyethyl, benzoyl, triphenylmethyl, t-butyl, benzyl, adamantyl, cyanoethyl, acetyl, and trifluoroacetyl.

Alcohol protecting groups are well known to those skilled in the art. See, for example, "Protective Groups in Organic Synthesis" (1999), Chapter 2. In some embodiments, an alcohol protecting group may be selected from the group consisting of, methoxymethyl, (phenyldimethylsilyl)methoxymethyl, benzyloxymethyl, t-butyldimethylsilyl, t-butoxymethyl, and tetrahydropyranyl.

Carbonyl protecting groups are well known to those skilled in the art. See, for example, "Protective Groups in Organic Synthesis" (1999), Chapter 4. In some embodiments, a carbonyl protecting group may be selected from the group consisting of dimethylacetal, dimethylketal, diisopropylacetal, diisopropylketal, enamines and enol ethers.

Carboxylic acid protecting groups are well known to those skilled in the art. See, for example, "Protective Groups in Organic Synthesis" (1999), Chapter 5. In some embodiments, a carboxylic acid protecting group may be selected from the group consisting of dimethylacetal, methoxymethylester, phenylacetoxymethyl ester and tetrahydropyranyl ester.

Compounds as described herein may contain one or more asymmetric centers and thus can occur as racemates and racemic mixtures, single enantiomers, diastereomeric mixtures and individual diastereomers. All possible stereoisomers of the all the compounds described herein, unless otherwise noted, are contemplated as being within the scope of the present invention. The chiral centers of the compounds of the present invention can have the S- or the R-configuration, as defined by the IUPAC 1974 Recommendations. The present invention is meant to comprehend all such isomeric forms of the compounds of the invention.

The claimed invention is also intended to encompass salts of any of the synthesized compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred as described below, although other salts may be useful, as for example in isolation or purification steps.

Non-limiting examples of acid addition salts include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate.

Non-limiting examples of basic salts include but are not limited to ammonium salts; alkali metal salts such as sodium, lithium, and potassium salts; alkaline earth metal salts such as calcium and magnesium salts; salts comprising organic bases such as amines (e.g., dicyclohexylamine, alkylamines such as t-butylamine and t-amylamine, substituted alkylamines, arylalkylamines such as benzylamine, dialkylamines, substituted dialkylamines such as N-methyl glucamine (especially N-methyl D-glucamine), trialkylamines, and substituted trialkylamines); and salts comprising amino acids such as arginine, lysine and so forth. The basic nitrogen-containing groups may be quaternized with agents such as lower alkyl halides (e.g. methyl, ethyl. propyl, and butyl chlorides, bromides and iodides), dialkyl sulfates (e.g. dimethyl, diethyl, dibutyl, and diamyl sulfates), long chain halides (e.g. decyl, lauryl, myrtistyl and stearyl chlorides, bromides and iodides), arylalkyl halides (e.g. benzyl and phenethyl bromides), and others known in the art.

Reagents for preparation of the compositions of the present invention can be obtained from any source. A wide range of sources are known to those of ordinary skill in the art. For example, the reagents can be obtained from commercial sources such as Sigma-Aldrich Chemical Company (Milwaukee, Wis.), from chemical synthesis, or from natural sources. The reagents may be isolated and purified using any technique known to those of ordinary skill in the art, as described herein.

B. Pharmaceutical Formulations and Administration Thereof

1. Pharmaceutical Formulations and Routes for Administration to Subjects

Pharmaceutical compositions of the present invention comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 1990).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a compound of the present invention. In other embodiments, the compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

2. Combination Therapy

In order to increase the effectiveness of a compound of the present invention, the compound may be combined with traditional drugs. It is contemplated that this type of combination therapy may be used in vitro or in vivo. In a non-limiting example, an anti-cancer agent may be used in combination with a compound. An anti-viral or antibiotic agent may be used in combination with a compound, for example.

More generally, agents of the present invention may be provided in a combined amount with an effective amount of an anti-cancer agent. This process may involve contacting the cell(s) with the agents at the same time or within a period of time wherein separate administration of the substances produces a desired therapeutic benefit. This may be achieved by contacting the cell, tissue or organism with a single composition or pharmacological formulation that includes two or more agents, or by contacting the cell with two or more distinct compositions or formulations, wherein one composition includes one agent and the other includes another.

The compounds of the present invention may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein a compound is "A" and a second agent, such as an anti-cancer agent, is "B":

A/B/A B/A/B B/B/A A/A/B A/B/B B/A/A A/B/B/B B/A/
B/B B/B/B/A B/B/A/B A/A/B/B A/B/A/B A/B/B/A
B/B/A/A B/A/B/A B/A/A/B A/A/A/B B/A/A/A A/B/
A/A A/A/B/A

An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing tumor size, inhibiting tumor growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents are well-known in the art and include, for example, chemotherapy agents (chemotherapy), radiotherapy agents (radiotherapy), a surgical procedure, immune therapy agents (immunotherapy), genetic therapy agents (gene therapy), reoviral therapy, hormonal therapy, other biological agents (biotherapy), and/or alternative therapies.

C. Examples

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

All reactions were carried out under nitrogen atmosphere in flame-dried glassware. Dichloromethane, acetonitrile, methanol, tetrahydrofuran, diethyl ether were purified by passage through activated molecular sieves based (solvent system). Huinig's base and triethylamine were distilled from potassium hydroxide prior to use. All other commercial reagents were used as received. The preparation of modified Mukaiyama reagent 2b has been reported previously. (Oh, et al. 2005). While it is not absolutely necessary to transfer this reagent in a glove box, over time this reagent does hydrolyze since it is somewhat hygroscopic and is best stored in a dessicator. Furthermore, while this reagent is easily prepared on scale, it is best stored in small quantities in separate bottles to minimize exposure to moisture. $^1$H NMR chemical shifts are reported as δ values in ppm relative to $CDCl_3$ (7.26 ppm), coupling constants (J) are reported in Hertz (Hz), and multiplicity follows convention along with the use of e.g. "app t" to indicate "apparent triplet" in cases where multiplicity is less complex than theoretical. Unless indicated otherwise, deuterochloroform ($CDCl_3$) served as an internal standard (77.0 ppm) for all $^{13}$C spectra. Flash column chromatography was performed using 60A Silica Gel (Baker, 230-400 mesh or Silacycle, 230-400 mesh) as a stationary phase. Mass spectra were obtained at the center for Chemical Characterization and Analysis (Texas A&M University). Thin layer chromatography (TLC) was performed using glass-backed silica gel $60_{F254}$ (Merck, 250 μm thickness). beta-Lactone 35a was previously described. (Cortez, et al., 2001).

Example 1

Non-Limiting Examples of General Methods of the Present Invention

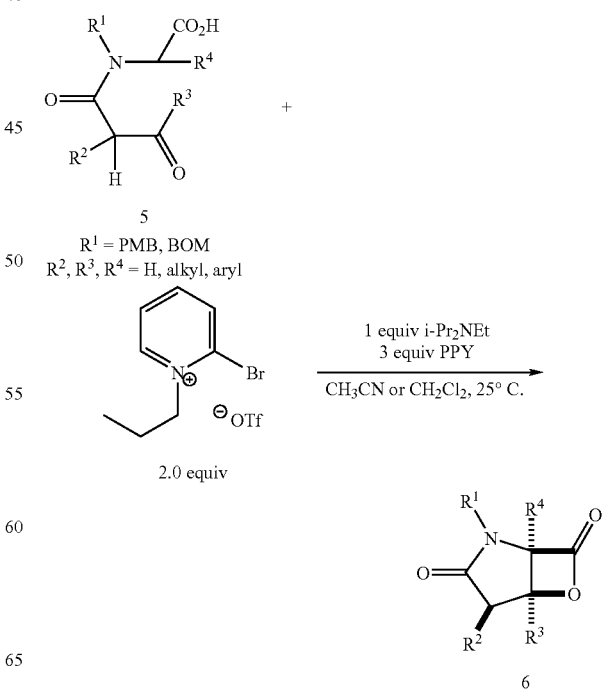

-continued

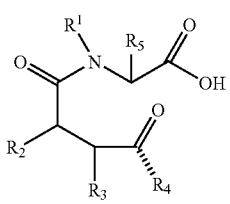

7
R[1] = PBM, BOM
R[2], R[3], R[4], R[5] = H, alkyl, aryl

+

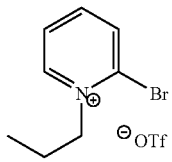

2.0 equiv.

$\xrightarrow{\begin{array}{c}\text{1 equiv i-Pr}_2\text{NEt}\\\text{3 equiv PPY}\\\hline\text{CH}_3\text{CN or CH}_2\text{Cl}_2\text{, 25° C.}\end{array}}$

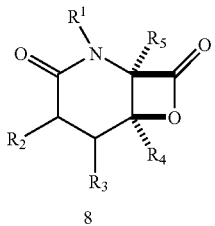

8

Example 2

Non-Limiting Example of a General Synthesis of Lactam-Fused Beta-Lactones

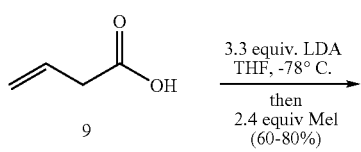

9

$\xrightarrow{\begin{array}{c}\text{3.3 equiv. LDA}\\\text{THF, -78° C.}\\\text{then}\\\text{2.4 equiv MeI}\\(60\text{-}80\%)\end{array}}$

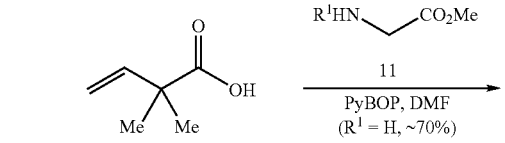

10

$\xrightarrow[\text{(R}^1 = \text{H, ~70\%)}]{\begin{array}{c}\text{R}^1\text{HN}\diagup\text{CO}_2\text{Me}\\\text{11}\\\hline\text{PyBOP, DMF}\end{array}}$

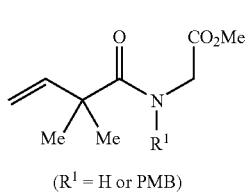

(R[1] = H or PMB)
12

$\xrightarrow{\begin{array}{c}\text{2.8 equiv LDA}\\\text{THF, -78° C.}\\\text{then E}^+\\(\text{E}^+ = \text{RI, RCHO})\end{array}}$ -continued

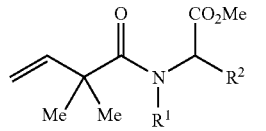

(R[1] = H, R[2] = CH(OH)Me[2])
(69%, dr ~1:1)
13

$\xrightarrow[(\text{R}^1 = \text{PMB; R}^2 = \text{O containing})]{\begin{array}{c}\text{TESOTf, 2,6-lut.}\\\text{CH}_2\text{Cl}_2\end{array}}$

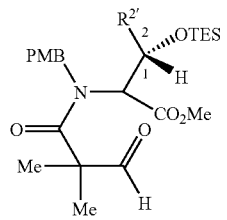

14

$\xrightarrow{\begin{array}{c}\text{1) LiOH, THF/H}_2\text{O}\\\text{2) O}_3\text{, DMS}\\\text{3) NCAL Process}\end{array}}$

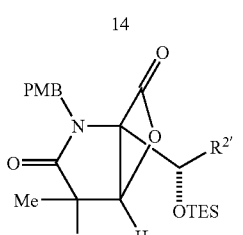

15

$\xrightarrow{\begin{array}{c}\text{1) HF • py, py.}\\\text{2) CAN, CH}_3\text{CN, H}_2\text{O}\end{array}}$

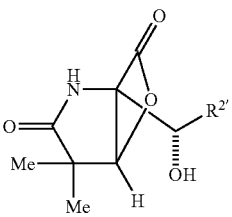

16

Example 3

Non-Limiting Example of a General Synthesis of Lactam-Fused Beta-Lactones

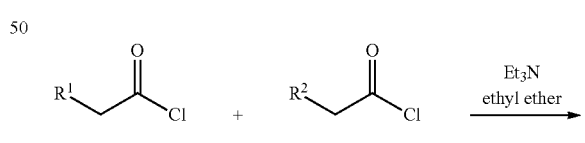

17    18

$\xrightarrow{\begin{array}{c}\text{Et}_3\text{N}\\\text{ethyl ether}\end{array}}$

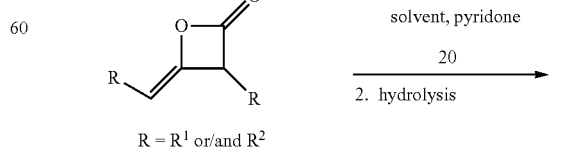

R = R[1] or/and R[2]
19

$\xrightarrow{\begin{array}{c}\text{1. } \begin{array}{c}\text{R}^3\diagup\text{CO}_2\text{R}^5\\|\\\text{NHR}^4\end{array}\\\text{solvent, pyridone}\\\underline{\hspace{2cm}20\hspace{2cm}}\\\text{2. hydrolysis}\end{array}}$

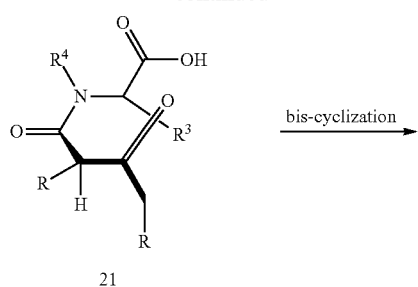
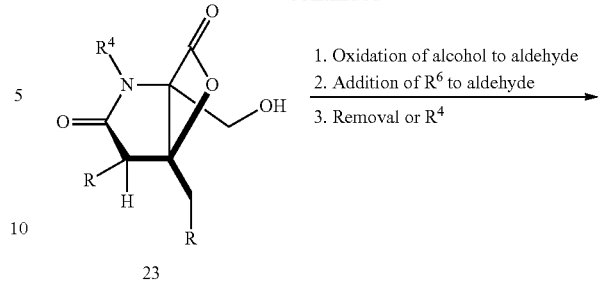
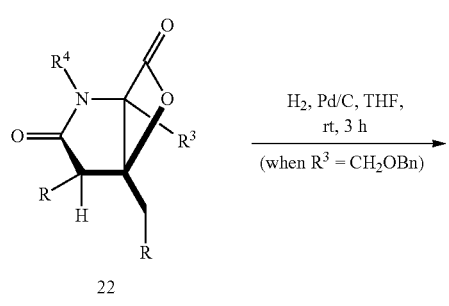
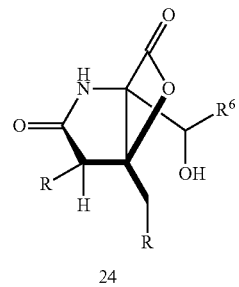
Example 4
General Strategy toward Salinosporamide and Cinnabaramide A via the Intramolecular NCAL Process
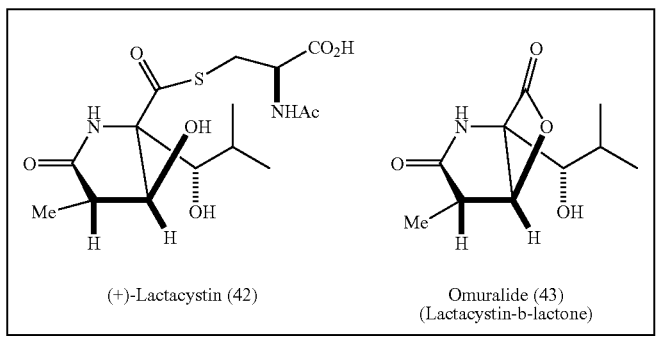
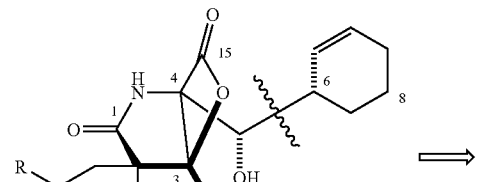
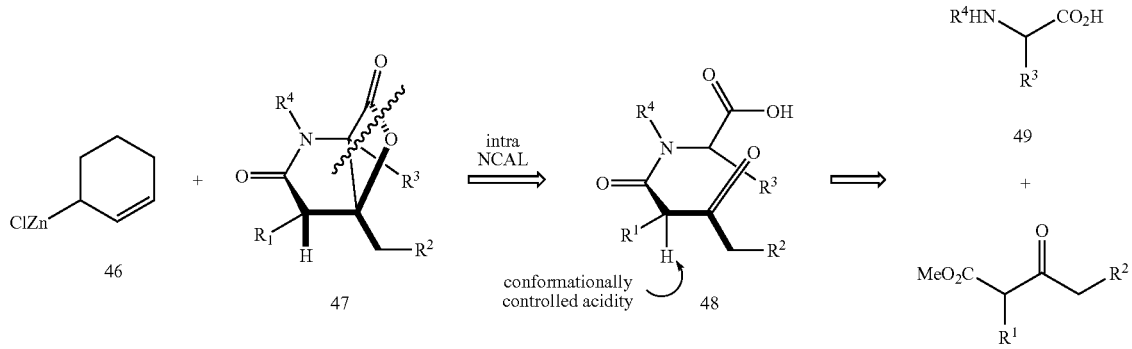

Example 5

Non-Limiting Example of the Synthesis of Simplified, C4-Unsubstituted Derivatives via the Intramolecular NCAL Process

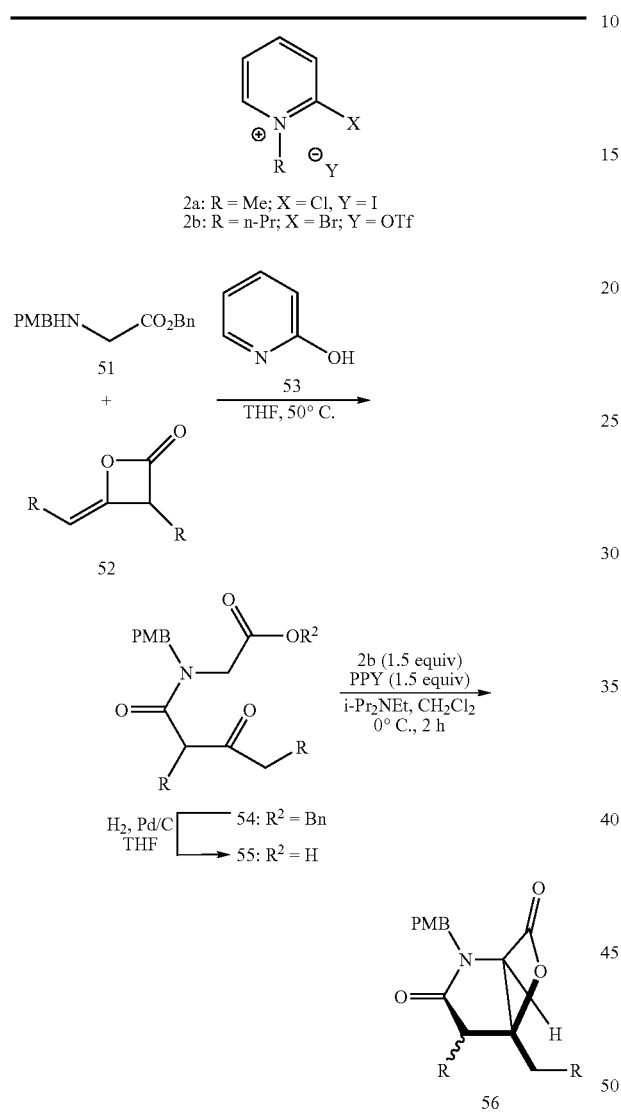

| entry | R | % yield (55)[a,b] | % yield (56)[b] | dr[c] |
|---|---|---|---|---|
| 1 | CyCH$_2$ | 84 (55a) | 93 (56a) | 2.2:1 |
| 2 | nHexyl | 80 (55b) | 90 (56b) | 2.2:1 |
| 3 | PhCH$_2$ | 72 (55c) | 85 (56c) | 2.5:1 (>19:1)[d] |
| 4 | Cl(CH$_2$)$_2$ | 40 (55d) | 45 | (>19:1)[d] |
| 5 | H | 77 (55d) | 25 (56d) | — |

[a] Yield is for 2 steps.
[b] Yields refer to isolated, purified (SiO$_2$) product.
[c] Determined by 1H NMR analysis of crude reaction mixtures.
[d] Observed diastereomeric ratio (dr) if reaction is allowed to proceed at 25° C. for 1.5 d (54% yield).
PMB = p-methoxybenzyl, 4-PPY = 4-pyrrolidinopyridine, Cy = cyclohexyl.

Example 6

Deprotection of Beta-Lactone (56b) and X-Ray Crystal Structure (POV Chem Rendering of Bicyclic Beta Lactone (57)

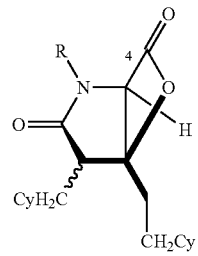

CAN
MeOH—H$_2$O
(89%)

56a: R = PMB
57: R = H

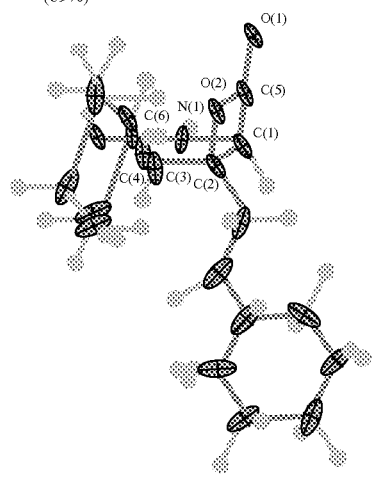

Example 7

Ketene-Homodimerization

Intermediates en Route to Certain Compounds of the Present Invention

Representative procedure (Method A) for 4-(2-cyclohexyl-ethylidene)-3-cyclohexylmethyl-oxetan-2-one ((±)-52a)

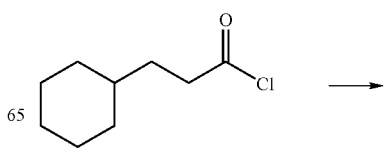

-continued

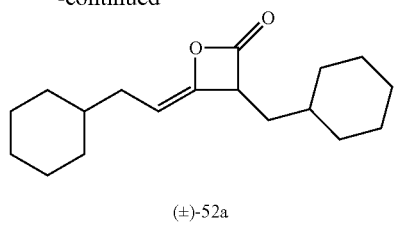

(±)-52a

To a solution of 3-cyclohexyl propionyl chloride (17.5 g, 100 mmol) in Et$_2$O (75 mL) was added triethylamine (16.0 mL, 110 mmol) at a rate sufficient to maintain gentle refluxing. During addition of triethylamine, a white solid precipitated. After complete addition of triethylamine, the reaction mixture was refluxed for an additional 1 h, cooled to ambient temperature, and filtered through a pad of Celite and SiO$_2$. The filtrate was concentrated under reduced pressure and the residue was purified by flash:chromatography (95:5 pentane:Et$_2$O) to afford ketene dimer (I)-52a (8.25 g, 60%) as a colorless oil.

4-Heptylidene-3-hexyl-oxetan-2-one ((±)-52b)

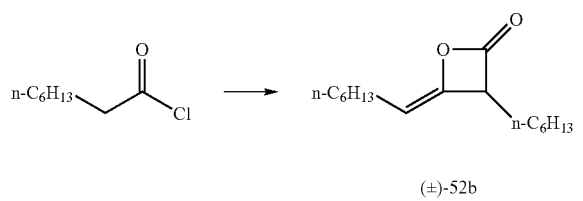

(±)-52b

Prepared according to the representative procedure (Method A) using octanoyl chloride (5.4 g, 33 mmol) in Et$_2$O (25 mL) and triethylamine (5.2 mL, 37 mmol). Purification by flash chromatography on SiO$_2$ (95:5 pentane:Et$_2$O) gave ketene dimer (I)-52b (3.0 g, 65%) as a clear oil. R$_f$=0.74 (20% EtOAc/hexanes); IR (neat) 1863, 1723 cm$^{-1}$; $^1$H NMR (500 MHz, C$_6$D$_6$) δ 4.36 (dt, J=1.5, 7.5 Hz, 1H), 3.33 (dt, J=1.0, 7.0 Hz, 1H), 2.01-2.15 (m, 2H), 1.02-1.36 (m, 18H), 0.87 (t, J=7.0 Hz, 3H), 0.84 (t, J=7.0 Hz, 3H); $^{13}$C NMR (125 MHz, C$_6$D$_6$) δ 169.0, 146.5, 101.0, 54.0, 31.9, 31.7, 29.8, 29.10, 29.08, 27.6, 26.5, 25.0, 23.0, 22.8, 14.3, 14.2; LRMS (CI) Calcd. for C$_{16}$H$_{28}$O$_2$ [M+H] 253, found 253; HRMS (ESI) Calcd. for C$_{16}$H$_{28}$O$_2$ [M+H] 253.2168, found 253.2169.

(Z)-3-Benzyl-4-phenethylidene-oxetan-2-one ((±)-52c)

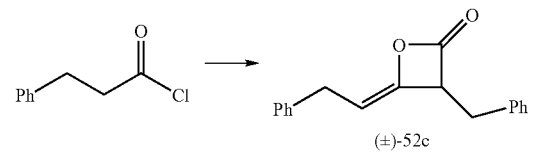

(±)-52c

Prepared according to the representative procedure (Method A) using hydrocinnamoyl chloride (5.0 g, 30 mmol) in diethyl ether (25 mL) and triethylamine (4.6 mL, 33 mmol). Purification by flash chromatography on SiO$_2$ (95:5 pentane:Et$_2$O) gave ketene dimer (±)-52c (1.75 g, 46%) as a clear oil.

(Z)-3-(2-Chloroethyl)-4-(3-chloropropylidene)oxetan-2-one ((±)-52d)

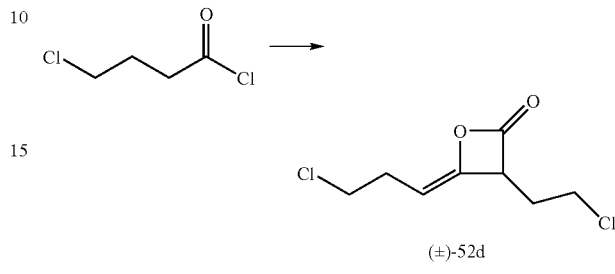

(±)-52d

Prepared according to the representative procedure (Method A) using 4-chlorobutyrylchloride (5.0 g, 34 mmol) in ethyl ether (25 mL), triethylamine (6.0 mL, 42 mmol). Purification by flash chromatography on SiO$_2$ (95:5 pentane:Et$_2$O) gave ketene dimer (±)-52d (1.6 g, 43%) as a clear oil. $^1$H NMR (500 MHz, C$_6$D$_6$) δ 4.20 (dt, J=1.5, 7.5 Hz, 1H), 3.37 (dt, J=1.0, 8.0 Hz, 1H), 3.01 (dd, J=2.0, 6.5 Hz, 2H), 2.86-2.98 (m, 2H), 2.09-2.21 (m, 2H), 1.32-1.47 (m, 2H).

Example 8

Ring Opening of Ketene Dimers to give Ketoamides

Intermediates En Route to Certain Compounds of the Present Invention

Representative procedure (Method B) for [(5-cyclohexyl-2-cyclohexylmethyl-3-oxo-pentanoyl)-(4-methoxy-benzyl)-amino]-acetic acid benzyl ester ((±)-54a)

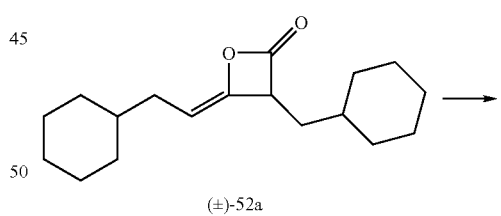

(±)-52a

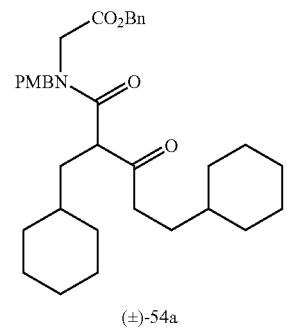

(±)-54a

To a solution of (4-methoxy-benzylamino)-acetic acid benzyl ester (178 mg, 0.624 mmol) and 2-hydroxypyridine (59 mg, 0.624 mmol) in THF (2 mL) was added ketene dimer (±)-52a (259 mg, 0.936 mmol). The reaction mixture was stirred at 50° C. for 1 day (or treated at 60° C. for 3 with microwave irradiation) and the solvent was evaporated under reduced pressure. The residue was purified by flash chromatography (1:4 EtOAc/hexanes) to afford keto ester (±)-54a (303 mg, 86%) as a colorless oil and as a 2.2:1 ratio of rotamers: IR (neat) 1749, 1652 cm$^{-1}$; $^1$H NMR (300 MHz, CDCl$_3$) δ 7.30-7-40 (m, 5H), 7.07-7.13 (m, 2H), 6.81-6.89 (m, 2H), 5.15 (s, 1.4H), 5.14 (0.6H), 4.73 (d, J=16.5 Hz, 0.7H), 4.68 (d, J=15.3 Hz, 0.3H), 4.49 (d, J=15.6 Hz, 0.3H), 4.43 (d, J=16.5 Hz, 0.7H), 4.27 (d, J=17.1 Hz, 0.7H), 4.13 (d, J=18.6 Hz, 0.3H), 3.94 (d, J=17.4 Hz, 0.7H), 3.93 (d, J=18.3 Hz, 0.3H), 3.78-3.83 (m, 3.7H) 3.55 (t, J=9.0 Hz, 0.3H), 2.40-2.58 (m, 2H), 0.76-1.94 (m, 26H); $^{13}$C NMR were complex due to the presence of rotamers and attempted VT NMR did not lead to coalescence so these are not included; LRMS (ESI) Calcd. for C$_{35}$H$_{47}$NO$_5$ [M+H] 561, found 562.

[(2-Hexyl-3-oxo-decanoyl)-(4-methoxy-benzyl)-amino]-acetic acid benzyl ester ((±)-54b)

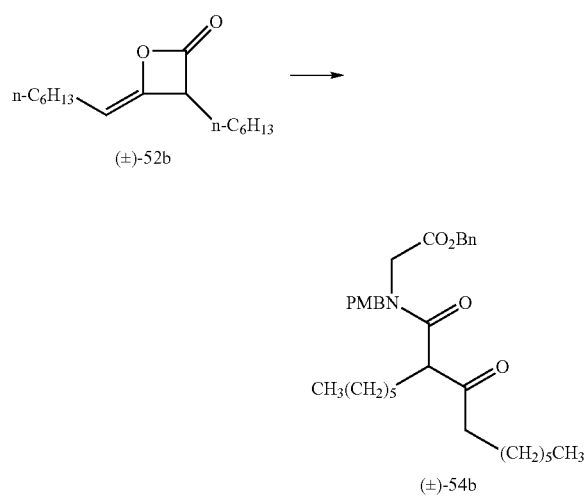

Prepared according to the representative procedure (Method B) using (4-methoxy-benzylamino)-acetic acid benzyl ester (910 mg, 3.02 mmol), 2-hydroxypyridine (304 mg, 3.02 mmol) in THF (13 mL), and ketene-dimer (±)-52b (800 mg, 3.02 mmol). Purification by flash chromatography on SiO$_2$ (1:4 EtOAc/hexanes) gave keto ester (i)-54b (1.36 g, 82%) as a colorless oil and as a 2.2:1 ratio of rotamers: IR (neat) 1750, 1646 cm$^{-1}$; $^1$H NMR (500 MHz, CDCl$_3$) δ 7.31-7.38 (m, 5H), 7.11 (d, J=8.0 Hz, 0.6H), 7.08 (d, J=8.5 Hz, 1.4H), 6.87 (d, J=8.5 Hz, 1.4H), 6.82 (d, J=8.5 Hz, 0.6H), 5.09-5.17 (m, 2H), 4.72 (d, J=16.5 Hz, 0.7H), 4.64 (d, J=15.0 Hz, 0.3H), 4.53 (d, J=15.0 Hz, 0.3H), 4.43 (d, J=16.5 Hz, 0.7H), 4.25 (d, J=17.5 Hz, 0.7H), 4.13 (d, J=19.0 Hz, 0.3H), 3.93 (d, J=18.5 Hz, 0.3H), 3.92 (d, J=17.5 Hz, 0.7H), 3.80 (s, 2.1H), 3.78 (s, 0.9H), 3.65 (t, J=7.0 Hz, 0.7H), 3.40 (t, J=7.0 Hz, 0.3H), 2.42-2.57 (m, 2H), 1.94-2.01 (m, 1H), 1.79-1.86 (m, 1H), 1.47-1.55 (m, 2H), 1.17-1.31 (m, 16H), 0.86-0.90 (m, 6H); $^{13}$C NMR were complex due to the presence of rotamers and attempted VT NMR did not lead to coalescence so these are not included; LRMS (ESI) Calcd. for C$_{33}$H$_{47}$NO$_5$ [M+Li] 544, found 544.

[(2-Benzyl-3-oxo-5-phenyl-pentanoyl)-(4-methoxy-benzyl)-amino]-acetic acid benzyl ester ((±)-54c)

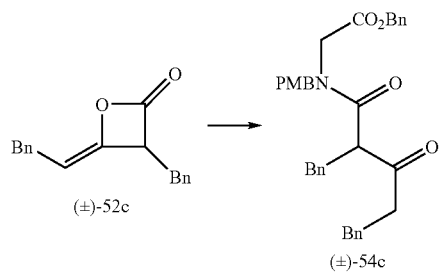

Prepared according to the representative procedure (Method B) using (4-methoxy-benzylamino)-acetic acid benzyl ester (636 mg, 2.23 mmol), 2-hydroxypyridine (212 mg, 2.23 mmol) in THF (22 mL), and ketene-dimer (±)-52c (588 mg, 2.22 mmol). Purification by flash chromatography on SiO$_2$ (1:4 EtOAc/hexanes) gave keto ester (±)-54c (1.04 g, 85%) as a colorless oil. 2.2:1 ratio of rotamers: IR (neat) 1745 1642 cm$^1$; $^{-1}$H NMR (500 MHz, CDCl$_3$) δ 7.08-7.38 (m, 15H), 6.98 (d, J=8.5 Hz, 0.6H), 6.78 (d, J=9.0 Hz, 0.6H), 6.72 (d, J=8.5 Hz, 1.4H), 6.69 (d, J=9.0 Hz, 1.4H), 5.14 (s, 1.4H), 5.05 (s, 0.6H), 4.77 (d, J=14.5 Hz, 0.3H), 4.56 (d, J=16.5 Hz, 0.7H), 4.31 (d, J=17.5 Hz, 0.7H), 4.28 (d, J=12.5 Hz, 0.3H), 4.18 (d, J=16.5 Hz, 0.7H), 3.96 (d, J=8.5 Hz, 0.3H), 3.95 (d, J=9.0 Hz, 0.3H), 3.79 (s, 0.9H), 3.78 (s, 2.1H), 3.64-3.72 (m, 1.7H), 3.29 (dd, J=9.0, 14.0 Hz, 0.7H), 3.16-3.24 (m, 0.6H), 3.12 (dd, J=5.5, 13.5 Hz, 0.7H), 2.77-2.96 (m, 4H); $^{13}$C NMR were complex due to the presence of rotamers and attempted VT NMR did not lead to coalescence so these are not included; LRMS (ESI) Calcd. for C$_{35}$H$_{35}$NO$_5$ [M+Li] 556, found 556.

[[6-Chloro-2-(2-chloro-ethyl)-3-oxo-hexanoyl]-(4-methoxy-benzyl)-amino]-acetic acid benzyl ester ((±)-54d)

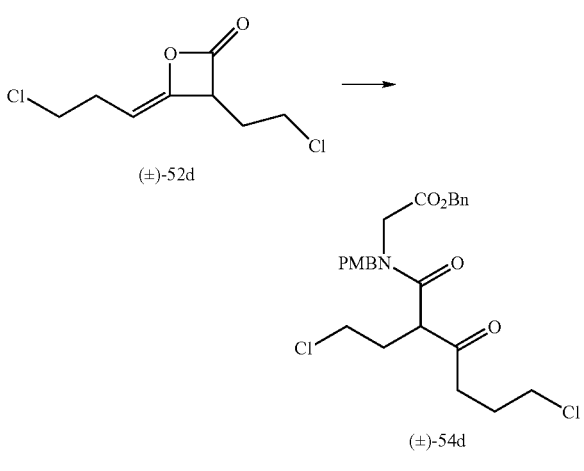

Prepared according to the representative procedure (Method B) using (4-methoxy-benzylamino)-acetic acid benzyl ester (180 mg, 0.622 mmol), 2-hydroxypyridine (60 mg, 0.622 mmol) in THF (8 mL), and ketene-dimer (±)-52d (130 mg, 0.622 mmol). Purification by flash chromatography on SiO$_2$ (1:4 EtOAc/hexanes) gave keto ester (±)-54d (155 mg, 50%) as a colorless oil. 2.2:1 ratio of rotamers: $^1$H NMR (500 MHz, CDCl$_3$) δ 7.31-7.40 (m, 5H), 7.11-7.18 (m, 2H), 6.82-6.92 (m, 2H), 5.17 (d, J=12.0 Hz, 1H), 5.13 (d, J=12.5 Hz, 1H), 4.54-4.71 (m, 2H), 4.04-4.22 (m, 2H), 3.78-3.81 (m, 4H), 3.60 (t, J=6.0 Hz, 2H), 3.46-3.57 (m, 2H), 2.24-2.77 (m, 4H), 1.96-2.04 (m, 2H); $^{13}$C NMR were complex due to the presence of rotamers and attempted VT NMR did not lead to coalescence so these are not included; LRMS (ESI) Calcd. for C$_{25}$H$_{29}$Cl$_2$NO$_5$ [M+H] 494, found 494.

[(4-Methoxy-benzyl)-(3-oxo-butyryl)-amino]-acetic acid benzyl ester (54e)

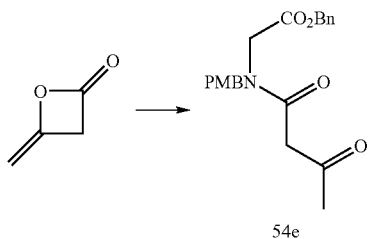

54e

Prepared according to the representative procedure (Method B) using (4-methoxy-benzylamino)-acetic acid benzyl ester (910 mg, 3.19 mmol), 2-hydroxypyridine (304 mg, 3.20 mmol) in THF (25 mL), and ketene dimer (1.0 mL, 16 mmol). Purification by flash chromatography on SiO$_2$ (1:4 EtOAc/hexanes) gave keto ester 54e (930 mg, 78%) as a colorless oil. Due to the presence of enol tautomers and amide rotamers, the NMR spectra of this compound is extremely complex and so line listing is not provided. R$_f$=0.28 (33% EtOAc/hexanes); IR (neat) 1747, 1720, 1646 cm$^{-1}$; LRMS (ESI) Calcd. for C$_{21}$H$_{23}$NO$_5$ [M+H] 370, found 370; HRMS (ESI) Calcd. for C$_{21}$H$_{23}$NO$_5$ [M+H] 370.1654, found 370.1655.

Example 9

Preparation of Keto Acid Intermediates

Intermediates En Route to Certain Compounds of the Present Invention

Representative procedure (Method C) from benzyl ester for [(5-cyclohexyl-2-cyclohexylmethyl-3-oxo-pentanoyl)-(4-methoxy-benzyl)-amino]-acetic acid ((±)-55a)

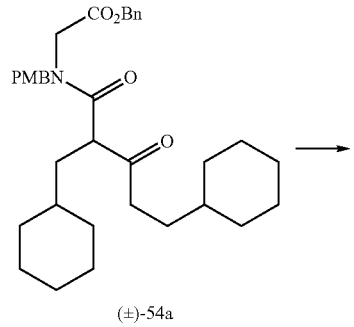

(±)-54a

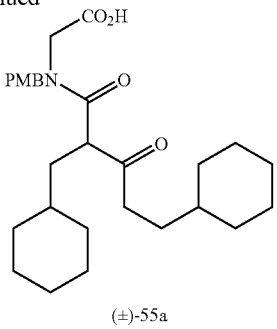

(±)-55a

A racemic mixture of keto ester benzyl ester (±)-54a (270 mg, 0.481 mmol), and 10 wt % palladium on carbon (27 mg) in a mixture of solvent THF (10 mL) was stirred at ambient temperature for 3 h under H$_2$ atmosphere. The reaction mixture was filtered through a pad of Celite, and concentrated to afford keto acid (±)-55a (222 mg, 98%) as a white solid and as a 2.2:1 ratio of two rotamers: IR (neat) 1729, 1652 cm$^{-1}$; $^1$H NMR (500 MHz, CDCl$_3$) δ 7.13 (d, J=8.5 Hz, 0.6H), 7.09 (d, J=8.5 Hz, 1.4H), 6.89 (d, J=9.0 Hz, 1.4H), 6.84 (d, J=9.0 Hz, 0.6H), 4.71 (d, J=16.5 Hz, 0.7H), 4.68 (d, J=13.5 Hz, 0.3H), 4.47 (d, J=15.0 Hz, 0.3H), 4.42 (d, J=16.5 Hz, 0.7H), 4.25 (d, J=17.5 Hz, 0.7H), 4.13 (d, J=19.0 Hz, 0.3H), 3.94 (d, J=18.0 Hz, 0.3H), 3.90 (d, J=17.0 Hz, 0.7H), 3.81 (s, 3H), 3.79 (dd, J=1.5, 4.5 Hz, 0.7H), 3.57 (t, J=7.0 Hz, 0.3H), 2.44-2.56 (m, 2H), 1.88-1.94 (m, 1H), 1.54-1.74 (m, 1H), 1.35-1.43 (m, 2H), 1.07-1.20 (m, 8H), 0.78-0.92 (m, 4H); LRMS (APCI) Calcd. for C$_{28}$H$_{41}$NO$_5$ [M−H] 470, found 470.

[(2-Hexyl-3-oxo-decanoyl)-(4-methoxy-benzyl)-amino]-acetic acid ((±)-55b)

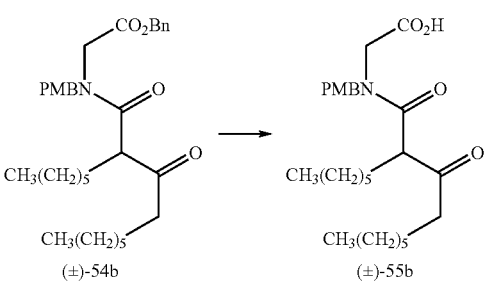

(±)-54b    (±)-55b

Prepared according to the representative procedure (Method C) for preparation of keto-acid intermediate from benzyl ester (±)-54b (415 mg, 0.772 mmol), palladium on carbon (40 mg) in a mixture of solvent THF (10 mL) afford keto acid (±)-55b (340 mg, 98%) as a colorless oil and as a 3:1 ratio of rotamers: IR (neat) 1721, 1649, 1614 cm$^{-1}$; $^1$H NMR (500 MHz, CDCl$_3$) δ 7.13 (d, J=8.5 Hz, 0.5H), 7.09 (d, J=8.5 Hz, 1.5H), 6.89 (d, J=9.0 Hz, 1.5H), 6.84 (d, J=8.5 Hz, 0.5H), 4.71 (d, J=16.5 Hz, 0.75H), 4.65 (d, J=14.5 Hz, 0.25H), 4.51 (d, J=14.5 Hz, 0.25H), 4.42 (d, J=16.5 Hz, 0.75H), 4.23 (d, J=17.5 Hz, 0.75H), 4.12 (d, J=19.0 Hz, 0.25H), 3.94 (d, J=19.0 Hz, 0.25H), 3.89 (d, J=17.5 Hz, 0.75H), 3.81 (s, 2.25H), 3.79 (s, 0.75H), 3.66 (dd, J=6.0, 8.0 Hz, 0.75H), 3.43 (t, J=7.0 Hz, 0.25H), 2.45-2.55 (m, 2H), 1.95-2.04 (m, 1H), 1.79-1.87 (m, 1H), 1.48-1.55 (m, 2H), 1.16-1.34 (m, 16H), 0.85-0.88 (m, 6H); LRMS (ESI) Calcd. for $C_{26}H_{41}NO_5$ [M–H] 446, found 446.

[(2-Benzyl-3-oxo-5-phenyl-pentanoyl)-(4-methoxy-benzyl)-amino]-acetic acid ((±)-55c)

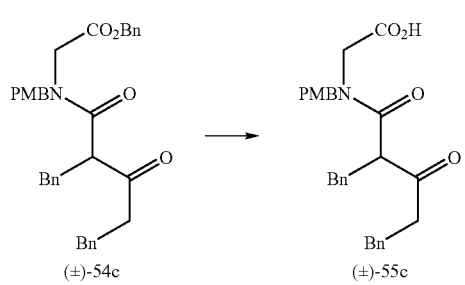

Prepared according to the representative procedure (Method C) for preparation of keto-acid intermediate from benzyl ester (±)-54c (985 mg, 1.79 mmol), palladium on carbon (99 mg) in a mixture of solvent THF (20 mL) and MeOH (4 mL) afford keto acid (±)-55c (0.70 g, 85%) as a white solid and as a 2.2:1 ratio of rotamers: IR (neat) 1722, 1634, 1612 cm$^{-1}$; $^1$H NMR (500 MHz, CDCl$_3$) δ 7.10-7.28 (m, 10H), 6.98 (d, J=8.5 Hz, 0.6H), 6.79 (d, J=9.0 Hz, 0.6H), 6.73 (d, J=9.0 Hz, 1.4H), 6.69 (d, J=9.0 Hz, 1.4H), 4.81 (d, J=15.0 Hz, 0.3H), 4.50 (d, J=16.5 Hz, 0.7H), 4.22 (d, J=14.5 Hz, 0.3H), 4.21 (d, J=17.0 Hz, 0.7H), 4.14 (d, J=16.5 Hz, 0.7H), 3.96 (d, J=9.0 Hz, 0.3H), 3.95 (d, J=9.0 Hz, 0.3H), 3.78 (s, 0.9H), 3.77 (s, 2.1H), 3.69 (d, J=17.5 Hz, 0.7H), 3.30 (dd, J=9.0, 13.0 Hz, 0.7H), 3.24 (dd, J=9.0, 13.0 Hz, 0.3H), 3.18 (dd, J=5.0, 13.5 Hz, 0.3H), 3.12 (dd, J=5.0, 13.5 Hz, 0.7H), 2.76-2.97 (m, 5H); LRMS (ESI) Calcd. for $C_{28}H_{29}NO_5$ [M–H] 458, found 458.

[[6-Chloro-2-(2-chloro-ethyl)-3-oxo-hexanoyl]-(4-methoxy-benzyl)-amino]-acetic acid ((±)-55d)

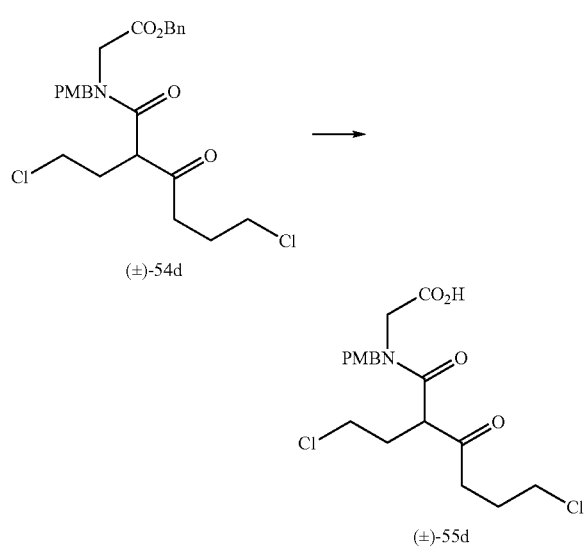

Prepared according to the representative procedure (Method C) for preparation of keto-acid intermediate from benzyl ester (±)-54d (155 mg, 0.314 mmol), palladium on carbon (50 mg) in a mixture of solvent THF (15 mL) and MeOH (3 mL) afford keto acid (±)-55d (100 mg, 80%) as a mixture of rotamers.

[(4-Methoxy-benzyl)-(3-oxo-butyryl)-amino]-acetic acid (55e)

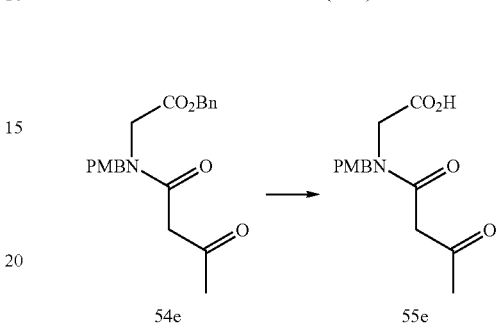

Prepared according to the representative procedure (Method C) for preparation of keto-acid intermediate from benzyl ester 54e (0.320 mg, 0.866 mmol), palladium on carbon (35 mg) in a mixture of solvent THF (10 mL) afford keto acid 55e (250 mg, 99%) as a colorless oil. IR (neat) 1723, 1612 cm$^{-1}$; $^1$H NMR (500 MHz, CDCl$_3$) δ 7.13 (d, J=8.5 Hz, 2H), 6.90 (d, J=8.0 Hz, 2H), 4.51 (s, 2H), 4.05 (s, 2H), 3.81 (s, 3H), 3.68 (s, 2H), 2.30 (s, 3H) (only major peaks were assigned); LRMS (ESI) Calcd. for $C_{14}H_{17}NO_5$ [M–H] 278, found 278; HRMS (ESI) Calcd. for $C_{14}H_{17}NO_5$ [M–H] 278.1028, found 278.1025.

Example 10

Preparation of Beta-Lactones Via Biscyclization

Representative Procedure (Method D) for 5-(2-cyclohexyl-ethyl)-4-cyclohexylmethyl-2-(4-methoxy-benzyl)-6-oxa-2-azabicyclo[3.2.0]heptane-3,7-dione ((±)-56a)

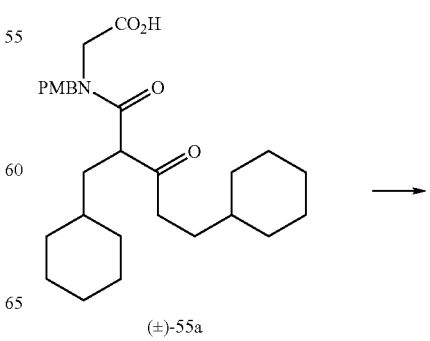

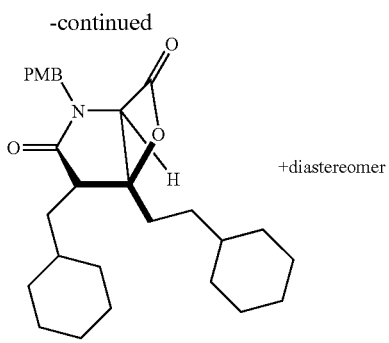

(±)-56a

To a suspension of N-propyl-2-bromo pyridinium triflate (95 mg, 0.27 mmol) and 4-pyrrolidinopyridine (40 mg, 0.27 mmol) in CH$_2$Cl$_2$ (4 mL) was added Hünig's base (63 µL, 0.36 mmol) at 0° C. After stirring for 10 min, a solution of keto-acid (±)-55a (85 mg, 0.18 mmol) in CH$_2$Cl$_2$ (3 mL) was added via syringe pump over 1 h at 0° C. The resulting suspension was stirred for 2 h at 0° C. The crude reaction mixture was diluted with Et$_2$O (50 mL) and washed with aqueous NH$_4$Cl solution and brine (each 30 mL). The organic layer were dried over Na$_2$SO$_4$, filtered, and concentrated. The residue was purified by flash chromatography (1:10 EtOAc/hexanes) to give a mixture of two beta-lactones (76 mg, 93%, dr 2.2:1) as a colorless oil. (±)-56a (major): R$_f$=0.76 (40% EtOAc/hexanes); IR (neat) 1825, 1709 cm$^{-1}$; $^1$H NMR (500 MHz, CDCl$_3$) δ 7.20 (d, J=8.5 Hz, 2H), 6.88 (d, J=8.5 Hz, 2H), 5.03 (d, J=14.5 Hz, 1H), 4.34 (s, 1H), 4.04 (d, J=14.5 Hz, 1H), 3.81 (s, 3H), 2.70 (dd, J=6.0, 7.5 Hz, 1H), 1.86-1.97 (m, 2H), 1.60-1.81 (m, 11H), 1.08-1.32 (m, 10H), 0.80-1.00 (m, 5H); $^{13}$C NMR (75 MHz, CDCl$_3$) δ 174.7, 166.2, 159.5, 130.0, 126.8, 114.3, 83.1, 68.2, 53.3, 45.2, 43.8, 37.3, 34.8, 33.6, 33.4, 33.2, 32.9, 32.6, 32.5, 31.2, 26.5, 26.4, 26.2, 26.1, 26.0 (2); LRMS (ESI) Calcd. for C$_{28}$H$_{39}$NO$_4$ [M+Li] 460, found 460.

4,5-Dihexyl-2-(4-methoxy-benzyl)-6-oxa-2-aza-bicyclo[3.2.0]heptane-3,7-dione ((±)-56b)

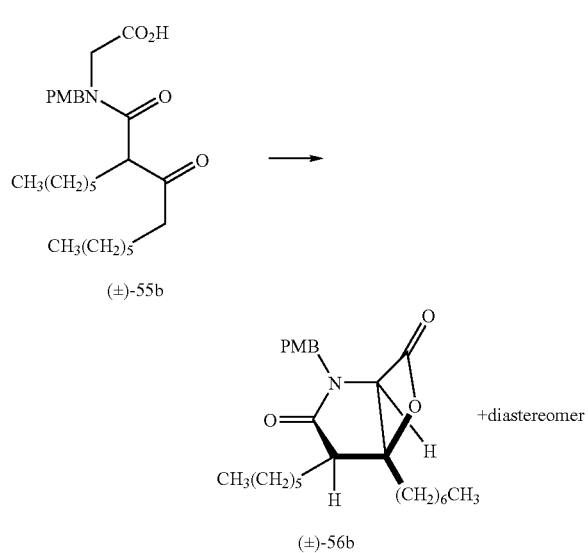

Prepared according to the representative procedure (Method D) for preparation of beta-lactone via bis-cyclization using N-propyl-2-bromo pyridinium triflate (141 mg, 0.402 mmol), 4-pyrrolidinopyridine (60 mg, 0.40 mmol), Hünig's base (93 µL, 0.54 mmol), and keto-acid (±)-55b (120 mg, 0.268 mmol) in CH$_2$Cl$_2$ (11 mL). Purification by flash chromatography on SiO$_2$ (1:10 EtOAc/hexanes) gave a mixture of two beta-lactones (104 mg, 90%, dr=2.2:1). (±)-56b (major): IR (neat) 1836, 1705 cm$^{-1}$; $^1$H NMR (500 MHz, CDCl$_3$) δ 7.20 (d, J=8.5 Hz, 2H), 6.88 (d, J=9.0 Hz, 2H), 5.04 (d, J=15.0 Hz, 1H), 4.36 (s, 1H), 4.05 (d, J=15.0 Hz, 1H), 3.80 (s, 3H), 2.55 (dd, J=5.5, 9.0 Hz, 1H), 1.85-2.00 (m, 3H), 1.69-1.77 (m, 1H), 1.47-1.58 (m, 2H), 1.18-1.39 (m, 16H), 0.89 (t, J=6.8 Hz, 3H), 0.87 (t, J=7.0 Hz, 3H); $^{13}$C NMR (75 MHz, CDCl$_3$) δ 174.5, 166.3, 159.7, 130.2, 127.0, 114.5, 83.0, 68.5, 55.4, 47.4, 45.4, 35.6, 31.74, 31.68, 29.5, 29.4, 29.1, 28.0, 26.3, 24.0, 22.8, 22.7, 14.24, 14.19; LRMS (ESI) Calcd. for C$_{26}$H$_{39}$NO$_4$ [M+H] 430, found 430.

4-Benzyl-2-(4-methoxy-benzyl)-5-phenethyl-6-oxa-2-aza-bicyclo[3.2.0]heptane-3,7-dione ((±)-56c)

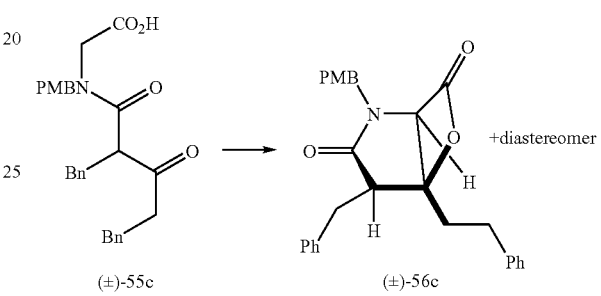

Prepared according to the representative procedure (Method D) for preparation of beta-lactone via biscyclization using N-propyl-2-bromo pyridinium triflate (84.6 mg, 0.245 mmol), 4-pyrrolidinopyridine (36.2 mg, 0.245 mmol), Hünig's base (57 µL, 0.33 mmol), and keto-acid (±)-55c (75 mg, 0.16 mmol) in CH$_2$Cl$_2$ (6.5 mL). Purification by flash chromatography on SiO$_2$ (1:4 EtOAc/hexanes) gave beta-lactone (I)-56c (61 mg, 85%, dr=2.5:1). R$_f$=0.29 (20% EtOAc/hexanes); IR (neat) 1830, 1702, 1612 cm$^{-1}$; $^1$H NMR (500 MHz, CDCl$_3$) δ 6.83-7.34 (m, 14H), 4.99 (d, J=15.0 Hz, 1H), 4.12 (s, 1H), 4.07 (d, J=14.0 Hz, 1H), 3.83 (s, 3H), 3.38 (dd, J=3.0, 13.0 Hz, 1H), 2.98 (dd, J=11.5, 13.0 Hz, 1H), 2.92 (dd, J=3.5, 11.5 Hz, 1H), 2.34-2.43 (m, 2H), 1.63-1.79 (m, 2H); $^{13}$C NMR (75 MHz, CDCl$_3$) δ 172.8, 166.1, 159.7, 139.3, 138.6, 130.4, 129.4, 128.9, 128.8, 128.1, 127.0, 126.7, 126.6, 114.5, 82.5, 68.8, 55.5, 49.7, 45.6, 36.2, 31.6, 30.1; LRMS (ESI) Calcd. for C$_{28}$H$_{27}$NO$_4$ [M+H] 442, found 442.

4-(2-Chloro-ethyl)-5-(3-chloro-propyl)-2-(4-methoxy-benzyl)-6-oxa-2-aza-bicyclo[3.2.0]heptane-3,7-dione ((±)-56d):

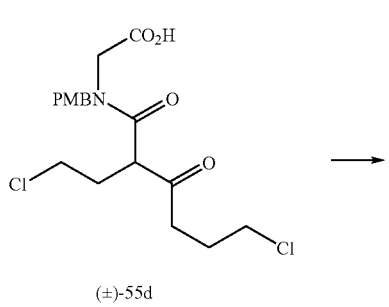

(±)-55d

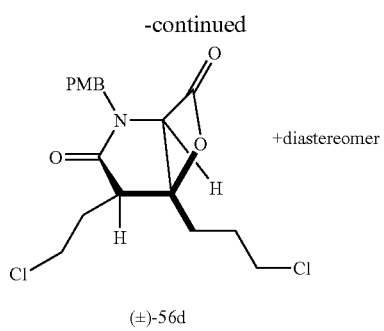

(±)-56d
+diastereomer

Prepared according to the representative procedure (Method D) for preparation of beta-lactone via biscyclization using N-propyl-2-bromo pyridinium triflate (286 mg, 0.83 mmol), 4-pyrrolidinopyridine (177 mg, 1.24 mmol), Hünig's base (50 µL, 0.25 mmol), and keto-acid (±)-55d (100 mg, 0.247 mmol) in CH$_2$Cl$_2$ (10 mL). Purification by flash chromatography on SiO$_2$ (1:3 EtOAc/hexanes) gave beta-lactone (±)-56d (40 mg, 45%, dr=2.5:1). IR (neat) 1832, 1702 cm$^{-1}$; $^1$H NMR (500 MHz, CDCl$_3$) δ 7.22 (d, J=14.5 Hz, 2H), 6.90 (d, J=14.5 Hz, 1H), 5.05 (d, J=24.5 Hz, 1H), 4.45 (s, 1H), 4.02-4.10 (m, 2H), 3.82 (s, 3H), 3.73-3.81 (m, 1H), 3.49-3.62 (m, 2H), 2.98 (t, J=12 Hz, 1H), 2.08-2.40 (m, 4H), 1.84-1.93 (m, 2H); $^{13}$C NMR (125 MHz, CDCl$_3$) δ 173.1, 165.1, 159.6, 130.1, 126.3, 114.4, 81.4, 68.9, 55.3, 45.3, 43.8, 43.7, 42.4, 32.4, 29.0, 26.6.

2-(4-Methoxy-benzyl)-6-oxa-2-aza-bicyclo[3.2.0]heptane-3,7-dione ((1)-19d)

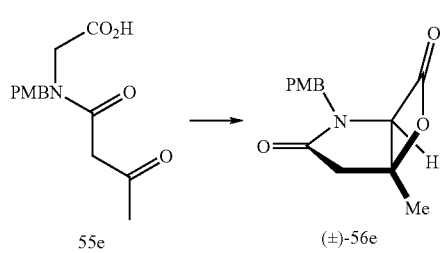

55e                    (±)-56e

Prepared according to the representative procedure (Method D) for preparation of beta-lactone via biscyclization using N-propyl-2-bromo pyridinium triflate (188 mg, 0.537 mmol), 4-pyrrolidinopyridine (79.6 mg, 0.577 mmol), Hünig's base (125 µL, 0.716 mmol), and keto-acid 55e (100 mg, 0.358 mmol) in CH$_2$Cl$_2$ (14 mL). Purification by flash chromatography on SiO$_2$ (2:3 EtOAc/hexanes) gave beta-lactone (O)-56e (23 mg, 25%). R$_f$=0.14 (33% EtOAc/hexanes); IR (neat) 1836, 1702 cm$^{-1}$; $^1$H NMR (300 MHz, CDCl$_3$) δ 7.24 (d, J=8.4 Hz, 2H), 6.90 (d, J=8.4 Hz, 2H), 5.06 (d, J=14.7 Hz, 1H), 4.41 (s, 1H), 4.07 (d, J=14.7 Hz, 1H), 3.82 (s, 3H), 3.05 (d, J=18.9 Hz, 1H), 2.70 (d, J=18.6 Hz, 1H), 1.70 (s, 3H); $^{13}$C NMR (75 MHz, CDCl$_3$) δ 171.4, 165.8, 159.8, 130.4, 126.7, 114.5, 77.9, 71.7, 55.5, 45.5, 41.6, 22.2; LRMS (APCI) Calcd. for C$_{14}$H$_{15}$NO$_4$ [M+Li] 268, found 268.

Example 11

PMB-Deprotection

Representative Procedure for 5-(2-cyclohexyl-ethyl)-4-cyclohexylmethyl-6-oxa-2-aza-bicyclo[3.2.0]heptane-3,7-dione ((±)-57a):

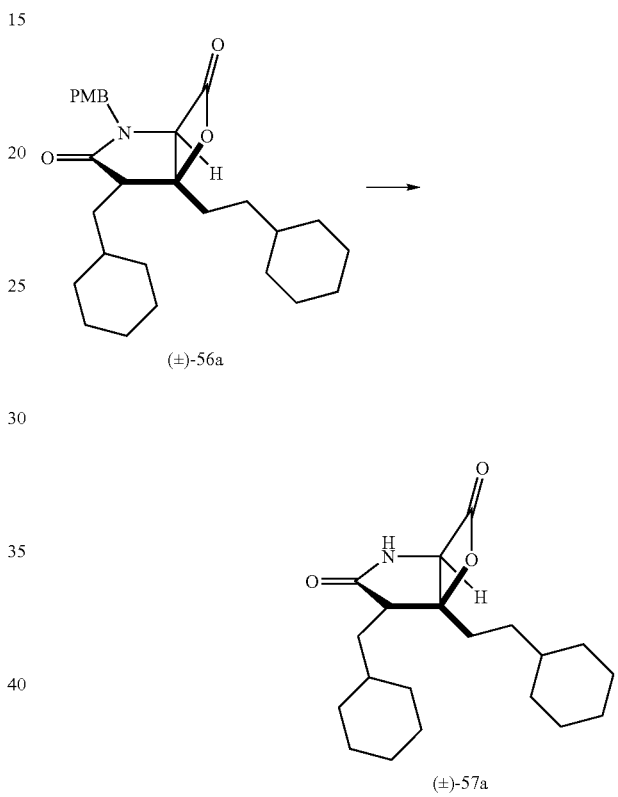

To a solution of (±)-56a (20 mg, 0.044 mmol) in CH$_3$CN (1 mL) was added an aqueous solution of CAN (123 mg, 0.225 mmol) in H$_2$O (0.4 mL) at 0° C. dropwise. After stirring at ambient temperature for 1 h, the reaction mixture was diluted with saturated NaHCO$_3$ (2 mL) and extracted EtOAc (5 mL×5). The combined organic layer was washed with brine, dried over MgSO$_4$, filtered and concentrated. The residue was purified by flash chromatography (1:6 to 1:1 EtOAc/hexanes) to give the desired product (±)-57a (13 mg, 89%) as a white solid. A crystal suitable for X-ray analysis was obtained by slow evaporation from Et$_2$O with ~5% CH$_2$Cl$_2$. R$_f$=0.55 (40% EtOAc/hexanes); IR (neat) 1832, 1709 cm$^{-1}$; $^1$H NMR (500 MHz, CDCl$_3$) δ 6.48 (s, 1H), 4.61 (s, 1H), 2.62 (dd, J=6.5, 8.5 Hz, 1H), 1.98-2.02 (m, 2H), 1.51-1.81 (m, 13H), 1.12-1.35 (m, 9H), 0.87-0.98 (m, 4H); $^{13}$C NMR (125 MHz, CDCl$_3$) δ 178.4, 166.7, 85.6, 65.2, 42.8, 37.5, 34.7, 33.7, 33.2, 33.1, 32.9, 32.7, 32.5, 31.4, 26.44, 26.37, 26.12, 26.09, 26.08, 26.0; LRMS (ESI) Calcd. for $C_{20}H_{31}NO_3$ [M+H] 334, found 334.

Example 12

Preparation of Beta-Lactone 62

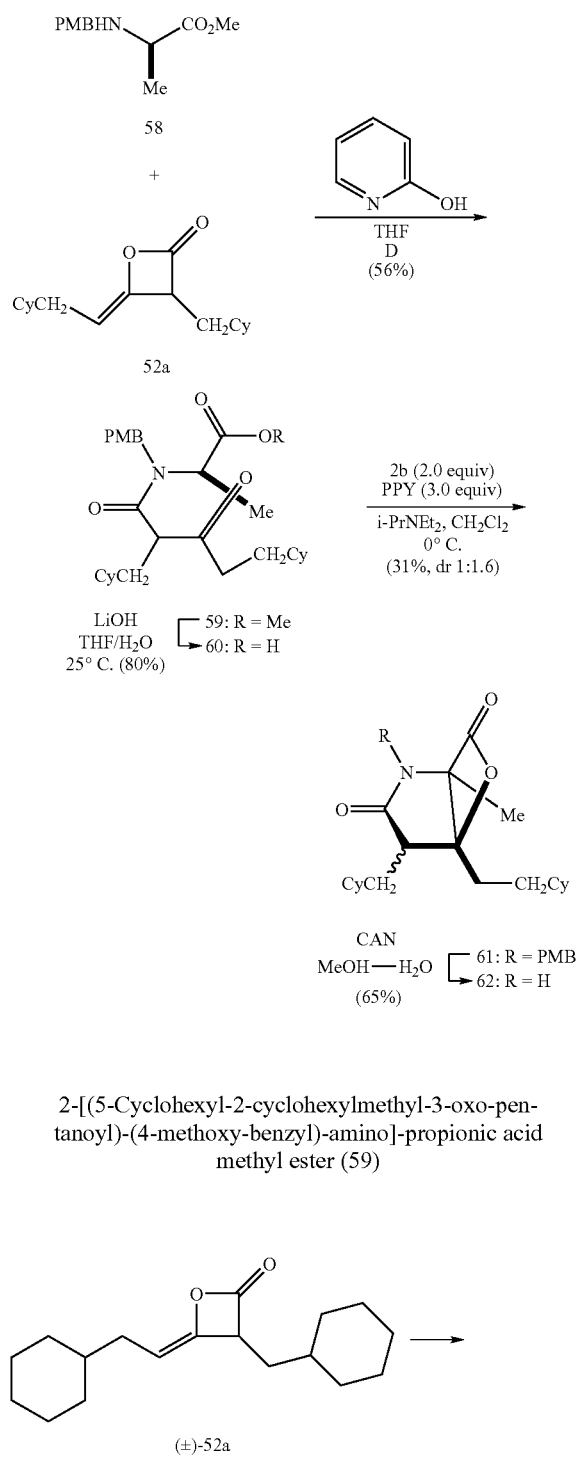

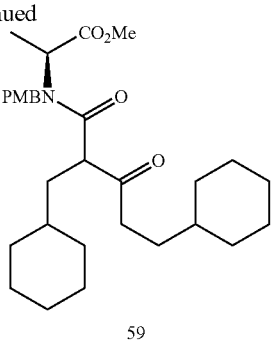

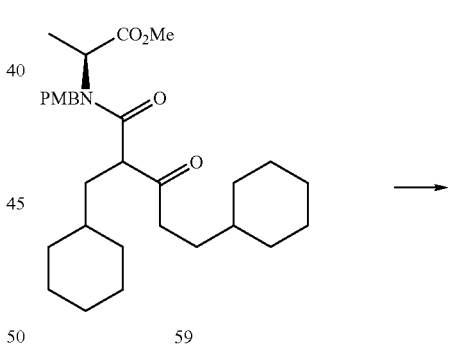

Prepared according to the representative procedure (Method B) for ring opening of ketene dimers to give ketoamides using (4-Methoxy-benzylamino)-acetic acid methyl ester (646 mg, 2.90 mmol), 2-hydroxypyridine (280 mg, 2.94 mmol) in THF (2.5 mL), and ketene-dimer (±)-52a (800 mg, 2.90 mmol). The reaction mixture was stirred at 50° C. for 2 day and the reaction mixture was purified by flash chromatography (1:10 EtOAc/hexanes) to give to afford a mixture of two diastereomers 59 (805 mg, 56%) as a colorless oil. IR (neat) 1746, 1650, 1613 $cm^{-1}$; $^1$H NMR (500 MHz, $CDCl_3$) δ 7.18 (d, J=8.5 Hz, 2H), 6.88 (d, J=8.5 Hz, 2H), 4.72 (d, J=17.5 Hz, 1H), 4.52 (q, J=7.5 Hz, 1H), 4.32 (d, J=17.0 Hz, 1H), 3.79 (s, 3H), 3.70 (s, 3H), 3.63 (dd, J=6.0, 8.5 Hz, 2H), 2.48 (t, J=7.5 Hz, 2H), 1.91 (ddd, J=5.5, 8.0, 14.0 Hz, 1H), 0.69-1.69 (m, 28H); LRMS (APCI) Calcd. for $C_{30}H_{45}NO_5$ [M+H] 500, found 500.

2-[(5-Cyclohexyl-2-cyclohexylmethyl-3-oxo-pentanoyl)-(4-methoxy-benzyl)-amino]-propionic acid (60)

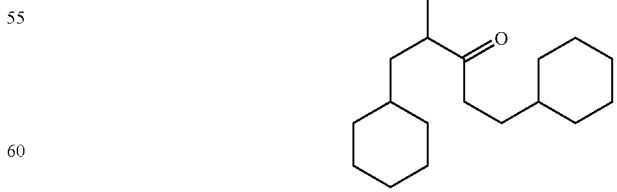

To a solution of methyl esters 59 (200 mg, 4.00 mmol) in $THF/H_2O$ (25 mL/4.5 mL) was added LiOH (1 M in $H_2O$, 0.50 mL, 4.4 mmol) at 10° C. dropwise. The reaction mixture was stirred at ambient temperature for 12 h and THF was removed under reduced pressure. The aqueous layer was acidified to pH2 with 1 M HCl and extracted with CH$_2$Cl$_2$ (25 mL×3). The combined organic layer was washed with brine, dried over MgSO$_4$, filtered and concentrated. The residue was purified by flash chromatography (1:3 EtOAc/hexanes) to give the desired acids 60 (155 mg, 80%) as a white solid. IR (neat) 3199, 1719, 1648, 1612 cm$^{-1}$; $^1$H NMR (500 MHz, CDCl$_3$) δ 7.18 (d, J=8.5 Hz, 2H), 6.89 (d, J=9.0 Hz, 2H), 4.69 (d, J=17.5 Hz, 1H), 4.54 (q, J=7.0 Hz, 1H), 4.34 (d, J=17.0 Hz, 1H), 3.80 (s, 3H), 3.64 (dd, J=5.5, 8.5 Hz, 2H), 2.49 (dd, J=7.0, 8.5 Hz, 2H), 1.91 (ddd, J=6.0, 8.5, 14.0 Hz, 1H), 0.69-1.70 (m, 28H); LRMS (ESI) Calcd. for C$_{29}$H$_{43}$NO$_5$ [M+H] 486, found 486.

5-(2-Cyclohexyl-ethyl)-4-cyclohexylmethyl-2-(4-methoxy-benzyl)-1-methyl-6-oxa-2-aza-bicyclo[3.2.0]heptane-3,7-dione ((O)-61)

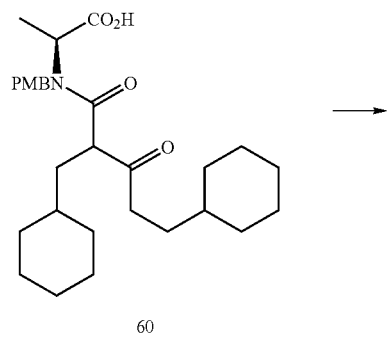

60

To a suspension of N-propyl-2-bromo pyridinium triflate (285 mg, 0.824 mmol) and 4-pyrrolidinopyridine (183 mg, 1.24 mmol) in CH$_2$Cl$_2$ (11.5 mL) was added Hünig's base (72 µL, 0.41 mmol) at 0° C. After stirring for 10 min, a solution of keto-acid 60 (200 mg, 0.412 mmol) in CH$_2$Cl$_2$ (5 mL) was added via syringe pump over 1 h at 0° C. The resulting suspension was stirred for 3 h at 0° C., at which point the volatiles were removed up to one-third under reduced pressure. The crude reaction mixture was diluted with Et$_2$O (100 mL) and washed with aqueous NH$_4$Cl solution and brine (each 30 mL). The organic layer were dried over Na$_2$SO$_4$, filtered, and concentrated. The residue was purified by flash chromatography (1:10 EtOAc/hexanes) to give a mixture of two beta-lactones (60 mg, 31%, dr 1:1.6) as a colorless oil. (±)-61 (major): R$_f$=0.56 (20% EtOAc/hexanes); IR (neat) 1829,1701 cm$^{-1}$; $^1$H NMR (500 MHz, CDCl$_3$) δ 7.22 (d, J=8.5 Hz, 2H), 6.84 (d, J=9.0 Hz, 2H), 4.76 (d, J=15.5 Hz, 1H), 4.28 (d, J=15.0 Hz, 1H), 3.80 (s, 3H), 2.75 (t, J=7.0 Hz, 1H), 1.65-2.03 (m, 15H), 1.39 (s, 3H), 0.85-1.34 (m, 13H); $^{13}$C NMR (75 MHz, CDCl$_3$) δ 175.0, 169.2, 159.3, 129.6, 129.4, 114.2, 86.8, 76.4, 55.4, 44.4, 42.2, 38.1, 35.0, 33.6, 33.5 (2), 33.3, 33.2, 31.7, 30.8, 26.7, 26.6, 26.3 (3), 13.0; LRMS (ESI) Calcd. for C$_{29}$H$_{41}$NO$_4$ [M+H] 468, found 468. (±)-61b (minor): R$_f$=0.63 (20% EtOAc/hexanes); IR (neat) 1829, 1702 cm$^{-1}$; $^1$H NMR (500 MHz, CDCl$_3$) δ 7.18 (d, J=8.5 Hz, 2H), 6.83 (d, J=8.5 Hz, 2H), 4.87 (d, J=15.5 Hz, 1H), 4.17 (d, J=15.5 Hz, 1H), 3.79 (s, 3H), 2.87 (dd, J=3.5, 11.0 Hz, 1H), 2.06 (br d, J=12.5 Hz, 1H), 1.46-1.87 (m, 12H), 1.14-1.42 (m, 12H), 0.79-1.10 (m, 4H); $^{13}$C NMR (125 MHz, CDCl$_3$) δ 174.3, 169.3, 159.0, 129.6, 128.9, 114.0, 87.2, 76.8, 55.2, 44.2, 43.8, 37.9, 37.4, 34.7, 34.5, 33.2, 33.0, 32.1, 30.4, 27.3, 26.5, 26.4, 26.2, 25.8, 12.3.

5-(2-Cyclohexyl-ethyl)-4-cyclohexylmethyl-1-methyl-6-oxa-2-aza-bicyclo[3.2.0]heptane-3,7-dione ((±)-62):

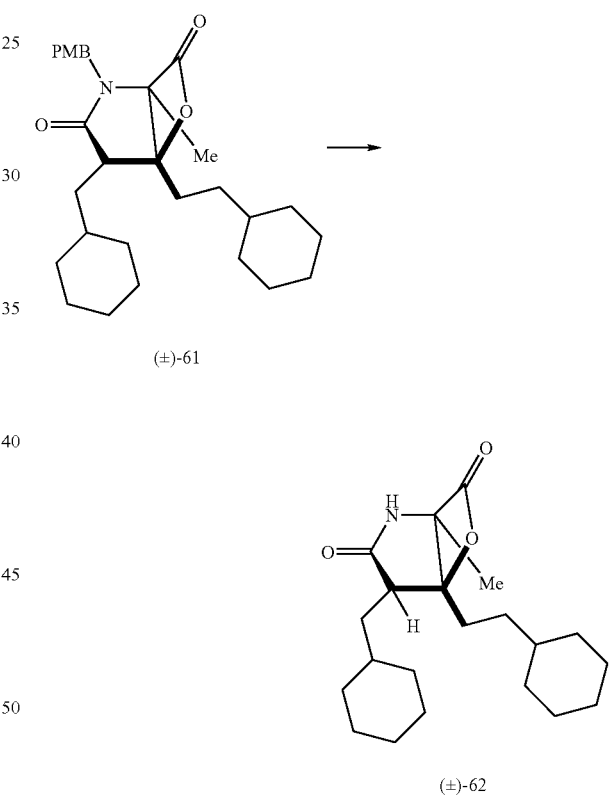

Prepared according to the representative procedure (Method E) for PMB-deprotection using (±)-61 (15.5 mg, 0.0331 mmol) in CH$_3$CN (0.4 mL) and CAN (50 mg, 0.091 mmol) in H$_2$O (0.1 mL). After stirring at 0° C. for 3 h, Purification by flash chromatography on SiO$_2$ (1:20 EtOAc/CH$_2$Cl$_2$) gave the desired product (±)-62 (7.5 mg, 65%) as a white solid. R$_f$=0.47 (10% EtOAc/CH$_2$Cl$_2$); IR (neat) 3223, 1832, 1708 cm$^{-1}$; $^1$H NMR (500 MHz, CDCl$_3$) δ 6.05 (s, 1H), 2.68 (t, J=7.0 Hz, 1H), 2.00 (ddd, J=5.0, 11.5, 15.8 Hz, 1H), 1.89 (ddd, J=4.5, 11.0, 15.0 Hz, 1H), 1.56-1.83 (m, 14H), 1.52 (s, 3H), 1.13-1.34 (m, 8H), 0.86-1.00 (m, 4H); $^{13}$C NMR (125 MHz, CDCl$_3$) δ 177.0, 170.3, 88.6, 72.2, 42.4, 38.1,

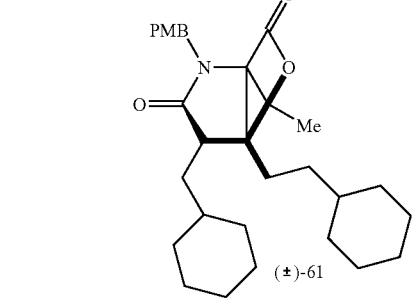

+ diastereomer (61b)

34.8, 33.5, 33.42, 33.36, 33.2, 31.6, 30.9, 26.7, 26.6, 26.4, 26.3, 13.8; LRMS (ESI) Calcd. for $C_{21}H_{33}NO_3$ [M+H] 338, found 338.

Example 13

Synthesis of (±)Cinnabaramide A

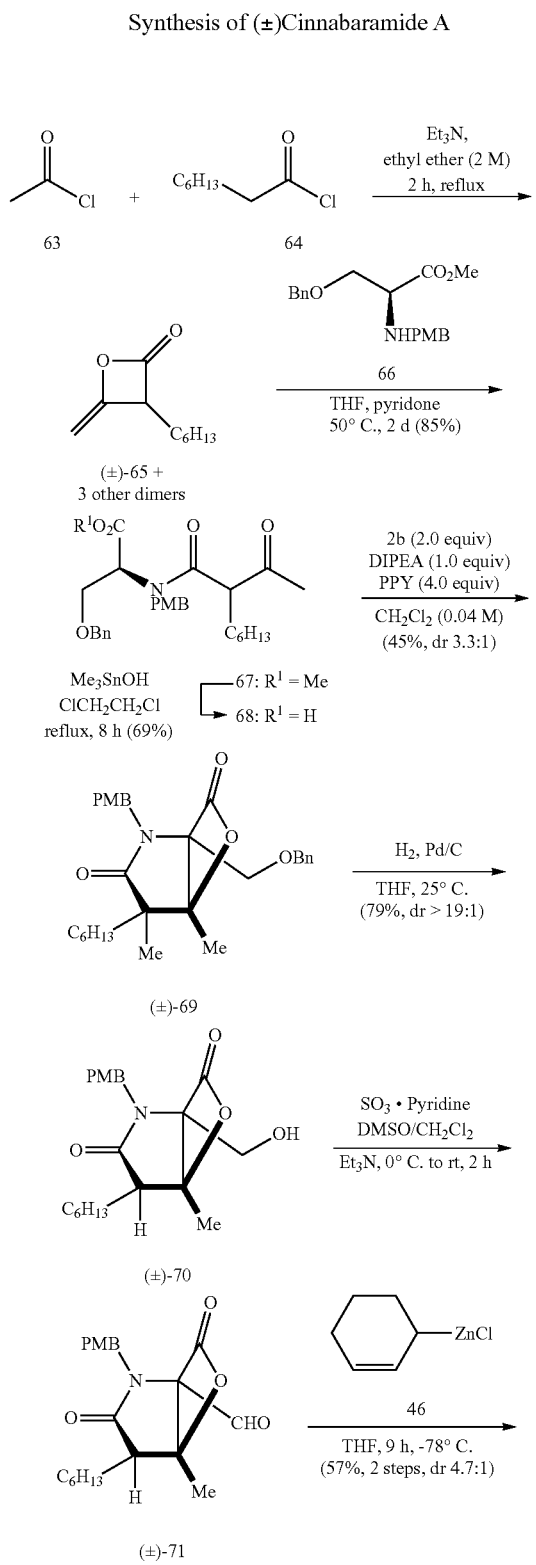

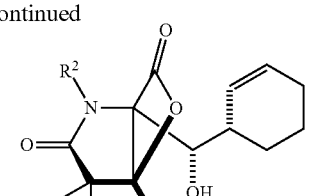

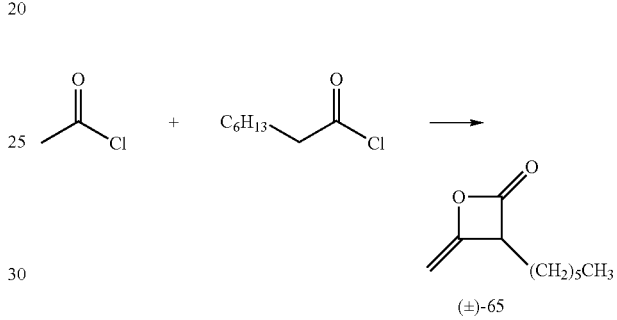

Representative Procedure (Method F) for Ketene-Heterodimerization as Described for 3-Hexyl-4-methylene-oxetan-2-one ((±)-65)

To a solution of acetyl chloride (9.0 mL, 120 mmol) and octanoyl chloride (10.2 mL, 60 mmol) in ethyl ether (90 mL) was added triethylamine (27 mL, 192 mmol) at a rate sufficient to maintaining refluxing. During addition of triethylamine, the triethylamine hydrochloride precipitated as a white solid. The reaction mixture was stirred for additional 1 h without further heating and filtered through a pad of Celite. The filtrate was concentrated under reduced pressure and the crude residue was distilled under vacuum to give a mixture of two ketene-dimers, which was purified by flash chromatography (5:95 $Et_2O$/hexanes) to afford ketene-dimer (±)-65 (0.5 g, 5%) as a colorless oil. IR (neat) $v_{max}$ 1888, 1860 1702 $cm^{-1}$; $^1H$ NMR (500 MHz, benzene-$d_6$) δ 4.51 (dd, J=2.0, 4.0 Hz, 1H), 3.91 (dd, J=1.0, 4.0 Hz, 1H), 3.21 (t, J=7.0 Hz, 1H), 0.94-1.30 (m, 10H), 0.85 (t, J=7.0 Hz, 3H); $^{13}C$ NMR (125 MHz, benzene-$d_6$) δ 168.4, 154.2, 84.8, 54.6, 31.6, 29.0, 27.2, 26.3, 22.8, 14.2; LRMS (ESI) Calcd. for $C_{10}H_{16}O_2$ [M+H] 169, found 169.

(S)-3-Benzyloxy-2-(4-methoxy-benzylamino)-propionic acid methyl ester (66)

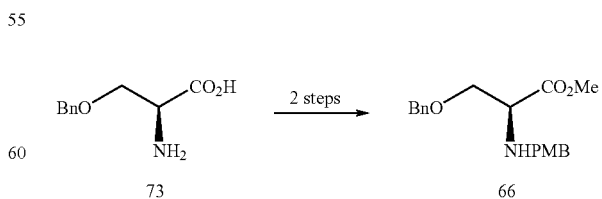

To the suspension of O-benzyl-L-serine 73 (3.85 g, 19.6 mmol) and p-anisaldehyde (3.21 g, 23.5 mmol) in MeOH (40 mL) was added triethylamine (3.28 mL, 23.5 mmol) at ambient temperature. The resulting suspension was stirred at ambient temperature for 1 h. The resulting solution was diluted with additional MeOH (40 mL) and NaBH$_4$ (1.11 g, 29.4 mmol) was added at 0° C. portionwise. After stirring at ambient temperature for 2 h, all volatiles were removed under reduced pressure. The remained solid was dissolved in water (50 mL) and acidified to pH 2 with 1 N HCl. The precipitate white solid was filtered, washed with water (2×30 mL) and Et$_2$O (2×30 mL), and dried under vacuum to give O-benzyl-N-PMB serine (5.21 g, 84%) as a white solid.

The suspension of O-benzyl-N-PMB serine (2.00 g, 6.34 mmol) in MeOH/Et$_2$O (each 16 mL) was added TMSCHN$_2$ (2 M in Et$_2$O, 6.4 mL, 12.8 mmol) dropwise until a yellow tint persisted. The reaction mixture was stirred at ambient temperature for additional 30 min and the all volatiles were removed under reduced pressure. The residue was purified by flash chromatography (1:3 EtOAc/hexanes) to give the desired methyl ester 66 (1.43 g, 69%) as a yellow oil. R$_f$=0.12 (20% EtOAc/hexanes); IR (neat) 1737 cm$^{-1}$; $^1$H NMR (500 MHz, CDCl$_3$) δ 7.27-7.35 (m, 5H), 7.25 (d, J=8.5 Hz, 2H), 6.85 (d, J=8.5 Hz, 2H), 4.53 (d, J=12.5 Hz, 1H), 4.49 (d, J=12.0 Hz, 1H), 3.82 (d, J=12.5 Hz, 1H), 3.79 (s, 3H), 3.73 (s, 3H), 3.71 (dd, J=5.5, 9.5 Hz, 1H), 3.66 (dd, J=5.0, 9.5 Hz, 1H), 3.65 (d, J=13.0 Hz, 1H), 3.50 (t, J=5.0 Hz, 1H), 2.15 (br, 1H); $^{13}$C NMR (125 MHz, CDCl$_3$) δ 173.6, 158.7, 137.8, 131.6, 129.5, 128.3, 127.6, 127.5, 113.7, 73.1, 70.9, 60.3, 55.2, 51.9, 51.4☐ LRMS (ESI) Calcd. for C$_{19}$H$_{23}$NO$_4$ [M+H] 330, found 330.

Representative Procedure for Ring Opening of Ketene Dimers to Give Ketoamides as Described for 2-[(2-Acetyl-octanoyl)-(4-methoxy-benzyl)-amino]-3-benzyloxy-propionic Acid Methyl Ester (67)

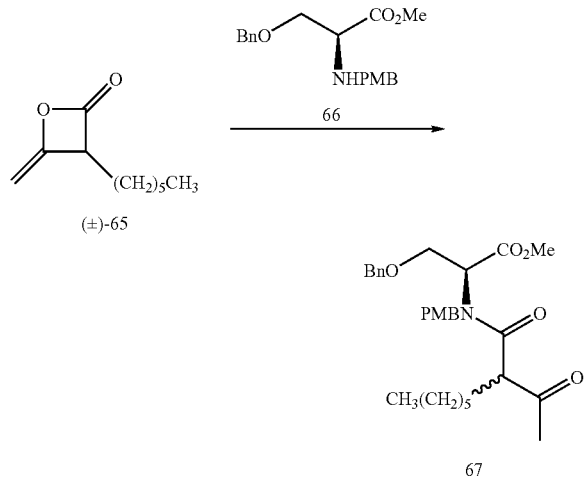

To a solution of (S)-3-benzyloxy-2-(4-methoxy-benzylamino)-propionic acid methyl ester 66 (670 mg, 2.03 mmol) and 2-hydroxypyridine (251 mg, 2.64 mmol) in THF (5 mL) was added ketene-dimer (O)-65 (450 mg, 2.64 mmol). The reaction mixture was stirred at 50° C. for 2 days and the solvent was evaporated under reduced pressure. The residue was purified by flash chromatography (1:10 EtOAc/hexanes) to afford a 1:1 mixture of diastereomeric keto esters 67 (855 mg, 85%) as a colorless oil. 67a: R$_f$=0.24 (20% EtOAc/hexanes); IR (neat) 1743, 1648 cm$^{-1}$; $^1$H NMR (300 MHz, CDCl$_3$) δ 7.20-7.38 (m, 7H), 6.86 (d, J=8.7 Hz, 2H), 4.83 (d, J=17.1 Hz, 1H), 4.52-4.65 (m, 2H), 4.41 (d, J=7.8 Hz, 1H), 4.39 (d, J=7.8 Hz, 1H), 4.00 (dd, J=7.2, 10.2 Hz, 1H), 3.94 (dd, J=4.5, 10.2 Hz, 1H), 3.81 (s, 3H), 3.72 (s, 3H), 3.53 (t, J=3.6 Hz, 1H), 2.15 (s, 3H), 1.93-2.02 (m, 1H), 1.68-1.80 (m, 1H), 1.08-1.35 (m, 8H), 0.88 (t, J=6.9 Hz, 3H); $^{13}$C NMR (75 MHz, CDCl$_3$) δ 205.1, 170.6, 169.3, 159.2, 137.8, 128.9, 128.6, 128.3, 128.0, 127.8, 114.1, 73.4, 68.4, 59.7, 58.8, 55.3, 52.2, 51.7, 31.6, 29.7, 29.1, 27.5, 27.0, 22.6, 14.1; LRMS (ESI) Calcd. for C$_{29}$H$_{39}$NO$_6$ [M+H] 498, found 498. 67b: R$_f$=0.16 (20% EtOAc/hexanes); IR (neat) 1742, 1645 cm$^{-1}$; $^1$H NMR (500 MHz, CDCl$_3$) δ 7.21-7.36 (m, 7H), 6.87 (d, J=9.0 Hz, 2H), 4.68 (s, 2H), 4.42-4.48 (m, 3H), 4.03 (dd, J=5.0, 10.5 Hz, 1H), 4.00 (dd, J=7.5, 10.5 Hz, 1H), 3.81 (s, 3H), 3.69 (s, 3H), 3.57 (t, J=6.5 Hz, 1H), 2.08 (s, 3H), 1.82-1.89 (m, 2H), 1.18-1.31 (m, 8H), 0.87 (t, J=6.5 Hz, 3H); $^{13}$C NMR (125 MHz, CDCl$_3$) δ 204.3, 170.9, 169.3, 159.3, 137.9, 128.7, 128.48, 128.46, 127.8, 127.7, 114.2, 73.4, 68.8, 60.0, 58.0, 55.4, 52.6, 52.2, 31.7, 29.5, 29.3, 27.7, 27.6, 22.7, 14.2.

Representative Procedure for Hydrolysis of Methyl Ester to Give Ketoacid Substrates as Described for 2-[(2-Acetyl-octanoyl)-(4-methoxy-benzyl)-amino]-3-benzyloxy-propionic acid (68)

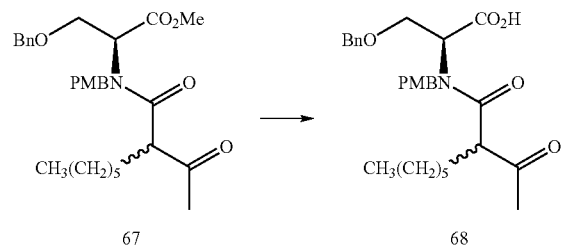

To a solution of diastereomeric methyl esters 67 (320 mg, 0.643 mmol) in 1,2-dichloroethane (4.5 mL) and in a sealed tube was added trimethyltin hydroxide (349 mg, 1.93 mmol) at ambient temperature. The reaction mixture was stirred at 80° C. for 8 h and diluted with EtOAc. The organic layer was washed with 0.5 N HCl (3×25 mL) and brine, dried over Na$_2$SO$_4$ and concentrated. The residue was purified by flash chromatography (1:10 EtOAc/hexanes to 1:1 CH$_2$Cl$_2$/EtOAc) to give the desired acid 68 (215 mg, 69%) and the recovered ester (68 mg, 21%) as colorless oils. Data for one diastereomer: IR (neat) 3153, 1726, 1650 cm$^{-1}$; $^1$H NMR (500 MHz, CDCl$_3$) δ 9.81 (br, 1H), 7.18-7.35 (m, 7H), 6.86 (d, J=8.5 Hz, 2H), 4.81 (d, J=17.0 Hz, 1H), 4.62 (dd, J=4.0, 7.5 Hz, 1H), 4.57 (d, J=17.0 Hz, 1H), 4.41 (s, 2H), 4.00 (dd, J=8.0, 10.0 Hz, 1H), 3.96 (dd, J=4.0, 10.5 Hz, 1H), 3.80 (s, 3H), 3.53 (dd, J=6.0, 7,5 Hz, 1H), 2.18 (s, 3H), 1.92-2.01 (m, 1H), 1.70-1.76 (m, 1H), 1.06-1.28 (m, 8H), 0.85 (t, J=6.5 Hz, 3H); $^{13}$C NMR (125 MHz, CDCl$_3$) δ 205.4, 173.9, 170.9, 159.3, 137.6, 128.6, 128.5, 128.3, 127.9, 127.8, 114.3, 73.5, 68.3, 59.7, 58.8, 55.4, 51.9, 31.7, 29.7, 29.1, 27.6, 27.1, 22.7, 14.2; LRMS (ESI) Calcd. for C$_{28}$H$_{37}$NO$_6$ [M−H] 482, found 482.

Representative Procedure for Bis-cyclization Process to give Bicyclic-β-lactone as Described for 1-Benzyloxymethyl-4-hexyl-2-(4-methoxy-benzyl)-5-methyl-6-oxa-2-aza-bicyclo[3.2.0]heptane-3,7-dione ((±)-69):

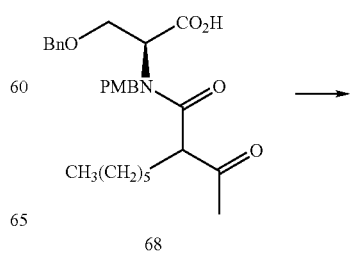

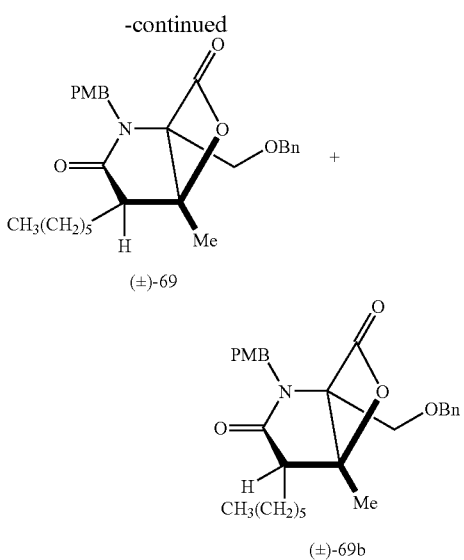

(±)-69

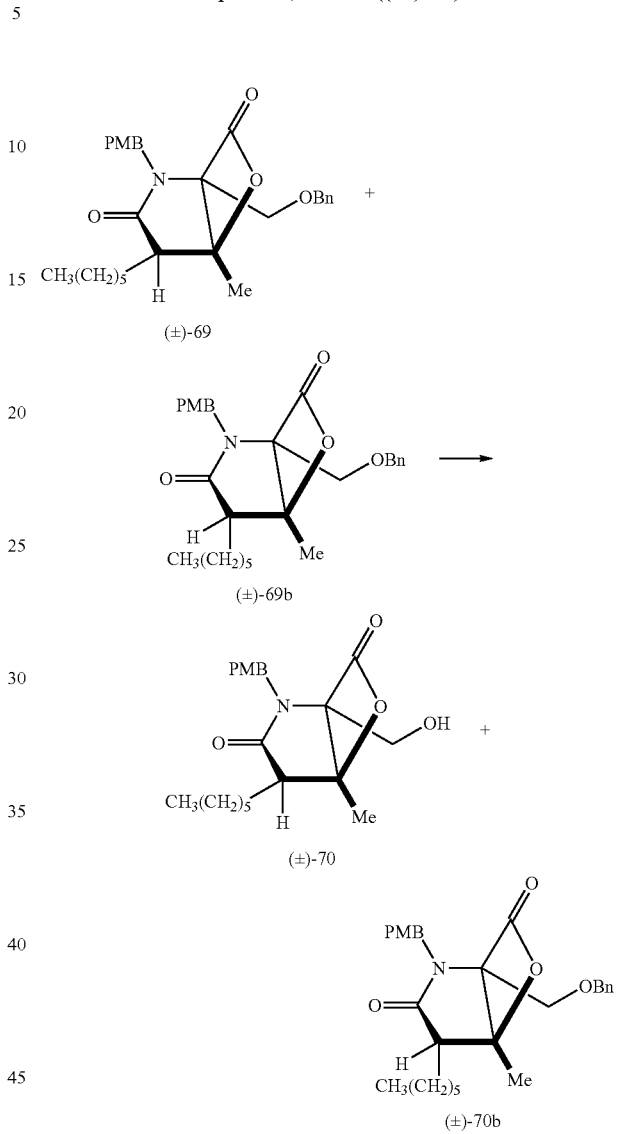

Representative Procedure for Debenzylation as Described for Hexyl-1-hydroxymethyl-2-(4-methoxy-benzyl)-5-methyl-6-oxa-2-aza-bicyclo[3.2.0]heptane-3,7-dione ((IL)-70)

To a suspension of N-propyl-2-bromo pyridinium triflate (343 mg, 0.993 mmol) and 4-pyrrolidinopyridine (294 mg, 1.98 mmol) in $CH_2Cl_2$ (6.5 mL) was added Hünig's base (86 μL, 0.50 mmol) at 0° C. After stirring for 10 min, a solution of keto-acids 68 (240 mg, 0.496 mmol) in $CH_2Cl_2$ (6 mL) was added via syringe pump over 1 h at 0° C. The resulting suspension was stirred for 7 h at 0° C., at which point the volatiles were removed to reduce to two-thirds original volume under reduced pressure. The crude reaction mixture was diluted with $Et_2O$ (100 mL) and washed with aqueous $NH_4Cl$ solution and brine (each 30 mL). The organic layer were dried over $Na_2SO_4$, filtered, and concentrated. The residue was purified by flash chromatography (1:10 EtOAc/hexanes) to give a mixture of two β-lactones (±)-69:69b (105 mg, 45%, dr 3.3:1, 500 MHz $^1$H NMR) as a colorless oil. (±)-69: $R_f$=0.36 (20% EtOAc/hexanes); IR (neat) 1835, 1704 cm$^{-1}$; $^1$H NMR (500 MHz, $C_6D_6$) δ 7.06-7.18 (m, 5H), 6.99 (dd, J=1.5, 8.0 Hz, 2H), 6.71 (dd, J=2.5, 7.0 Hz, 2H), 4.83 (d, J=15.5 Hz, 1H), 4.32 (d, J=15.5 Hz, 1H), 3.78 (s, 2H), 3.42 (d, J=11.5 Hz, 1H), 3.32 (d, J=11.5 Hz, 1H), 3.24 (s, 3H), 2.19 (dd, J=6.0, 9.0 Hz, 1H), 1.99-2.06 (m, 1H), 1.70-1.77 (m, 1H), 1.44-1.53 (m, 2H), 1.31 (s, 3H), 1.18-1.27 (m, 6H), 0.88 (t, J=7.0 Hz, 3H); $^{13}$C NMR (125 MHz, $C_6D_6$) δ 174.8, 166.8, 159.3, 136.7, 129.4, 129.0, 128.7, 128.3, 128.1, 114.0, 84.1, 79.2, 73.6, 61.9, 55.4, 48.7, 44.4, 31.7, 29.5, 28.1, 25.8, 22.8, 20.3, 14.2; LRMS (ESI) Calcd. for $C_{28}H_{35}NO_5$ [M+Li] 472, found 472.

The diastereomers were not readily separable and thus the minor diastereomer was characterized following subsequent benzyl group deprotection.

NOE Analysis of (±)-69 to Determine Relative Stereochemistry

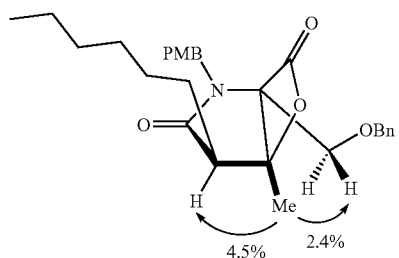

A mixture of beta-lactones (61 mg, 0.13 mmol) and 10 wt % palladium on carbon (10 mg) in THF (1.5 ml) was stirred at ambient temperature for 3 h under $H_2$ atmosphere. The reaction mixture was filtered through a pad of Celite, concentrated and purified by flash chromatography (1:5 to 1:1 EtOAc/hexanes) to give the desired major diastereomer (±)-70 (39 mg, 79%) and minor diastereomer (±)-70b (7 mg, 14%) as a waxy solid. (±)-70: $R_f$=0.20 (33% EtOAc/hexanes); IR (neat) 1831, 1700 cm$^{-1}$; $^1$H NMR (500 MHz, $CDCl_3$) δ 7.30 (d, J=8.5 Hz, 2H), 6.88 (d, J=8.5 Hz, 2H), 5.07 (d, J=15.0 Hz, 1H), 4.10 (d, J=15.5 Hz, 1H), 3.92 (dd, J=8.0, 13.0 Hz, 1H), 3.85 (dd, J=3.5, 13.5 Hz, 1H), 3.80 (s, 3H), 2.52 (dd, J=5.5, 8.5 Hz, 1H), 1.88-1.95 (m, 1H), 1.79 (s, 3H), 1.69-1.74 (m, 1H), 1.52-1.64 (m, 2H), 1.28-1.41 (m, 6H), 1.07 (dd, J=4.5, 8.5 Hz, 1H), 0.90 (t, J=7.0 Hz, 3H); $^{13}$C NMR (125 MHz, $CDCl_3$) δ 175.2, 167.3, 160.0, 129.3, 129.2, 114.9, 84.4, 80.2, 55.5, 55.3, 48.8, 44.3, 31.7, 29.5, 28.1, 25.7, 22.8, 20.1, 14.2; LRMS (ESI) Calcd. for $C_{21}H_{29}NO_5$ [M+Li] 382, found 382.

Minor diastereomer (±)-70b: $R_f$=0.33 (33% EtOAc/hexanes); IR (neat) 3424, 1830, 1679 cm$^{-1}$; $^1$H NMR (300 MHz, $C_6D_6$) δ 7.11 (d, J=8.1 Hz, 2H), 6.62 (d, J=8.7 Hz, 2H), 5.07 (d, J=15.0 Hz, 1H), 3.96 (d, J=15.0 Hz, 1H), 3.51 (dd, J=5.1, 13.8 Hz, 1H), 3.43 (dd, J=8.1, 13.5 Hz, 1H), 3.16 (s, 3H), 2.67 (t, J=6.3 Hz, 1H), 1.40-1.60 (m, 4H), 1.23 (s, 3H), 1.12-1.22 (m, 7H), 0.87 (t, J=6.3 Hz, 3H), 0.54 (dd, J=5.1, 9.0 Hz, 1H); $^{13}$C NMR (125 MHz, CDCl$_3$) δ 175.4, 167.5, 159.7, 129.4, 129.1, 114.9, 85.1, 81.0, 55.5, 55.3, 49.1, 44.2, 31.7, 29.5, 27.1, 22.8, 16.3, 14.3; LRMS (ESI) Calcd. for $C_{21}H_{29}NO_5$ [M+H] 376, found 376.

Representative Procedure as Described for 1-(Cyclohex-2-enyl-hydroxy-methyl)-4-hexyl-2-(4-methoxybenzyl)-5-methyl-6-oxa-2-aza-bicyclo[3.2.0]heptane-3,7-dione ((±)-70)

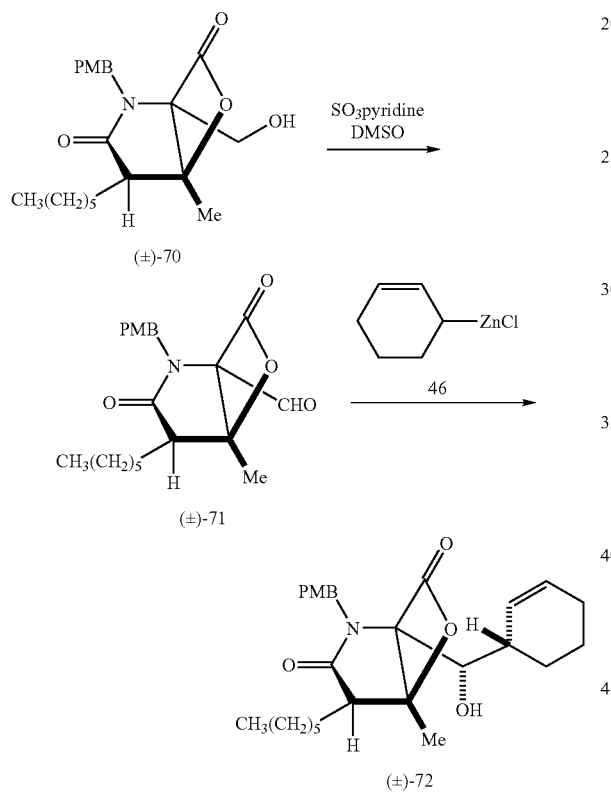

To a solution of alcohol (±)-70 (78.0 mg, 0.208 mmol) and Et$_3$N (116 μL, 0.832 mmol) in DMSO/CH$_2$Cl$_2$ (1.6 mL/0.8 mL) was added SO$_3$·pyridine (132 mg, 0.832 mmol) at 0° C. The reaction mixture was stirred at ambient temperature for 1 h and diluted with Et$_2$O (100 mL). The organic layer was washed with 0.2 N HCl and brine, dried over Na$_2$SO$_4$, filtered, and concentrated. The residue was used for the next step without further purification due to some instability of resulting aldehyde on purification by flash chromatography. Based on $^1$H NMR, conversion to the aldehyde was ~86%.

A solution of tri-n-butyl-2-cyclohexenyltin (309 mg, 0.832 mmol) in THF (1.6 mL) was treated with n-BuLi (2.5 M in hexanes, 0.37 mL, 0.92 mmol) at −78° C. After 30 min, the mixture was further treated with ZnCl$_2$ (0.5 M in THF, 1.66 mL, 0.832 mmol). After 30 min, a solution of the crude aldehyde (±)-71 in THF (2 mL) was slowly added to the freshly prepared zinc reagent 46. The resulting mixture was stirred at −78° C. for 8 h, quenched with water and diluted with EtOAc (100 mL). The organic layer was washed with saturated NH$_4$Cl and brine, dried over Na$_2$SO$_4$, filtered, and concentrated. The residue was purified by flash chromatography (1:4 EtOAc/hexanes) to give a mixture of two diastereomers (54 mg, 57% over 2 steps, dr 4.7:1, 500 MHz $^1$H NMR) as colorless oils and the desired diastereomer (±)-72 was the major as confirmed by subsequent conversion to the Bayer isolate (below). (±)-72: $R_f$=0.65 (33% EtOAc/hexanes); IR (neat) 1828, 1700, 1683 cm$^{-1}$; $^1$H NMR (500 MHz, CDCl$_3$) δ 7.24 (d, J=8.5 Hz, 2H), 6.84 (d, J=8.5 Hz, 2H), 5.78-5.82 (m, 1H), 5.51-5.56 (m, 1H), 4.67 (d, J=15.5 Hz, 1H), 4.45 (d, J=15.5 Hz, 1H), 4.09 (t, J=7.0 Hz, 1H), 3.79 (s, 3H), 2.52 (dd, J=6.0, 7.5 Hz, 1H), 2.27 (br, 1H), 2.05 (d, J=6.5 Hz, 1H), 1.90 (s, 3H), 1.59-1.89 (m, 5H), 1.30-1.42 (m, 9H), 0.99-1.06 (m, 1H), 0.91 (t, J=7.0 Hz, 3H); $^{13}$C NMR (75 MHz, CDCl$_3$) δ 175.4, 168.0, 159.5, 130.8, 130.0, 128.9, 126.1, 114.3, 85.9, 82.2, 70.7, 55.5, 49.0, 45.7, 37.4, 31.8, 29.6, 28.3, 25.9, 25.5, 24.9, 22.8, 21.4, 21.2, 14.3; LRMS (APCI) Calcd. for $C_{27}H_{37}NO_5$ [M+H] 456, found 456.

Representative Procedure as Described for 1-(Cyclohex-2-enyl-hydroxy-methyl)-4-hexyl-5-methyl-6-oxa-2-aza-bicyclo[3.2.0]heptane-3,7-dione ((I)-45)

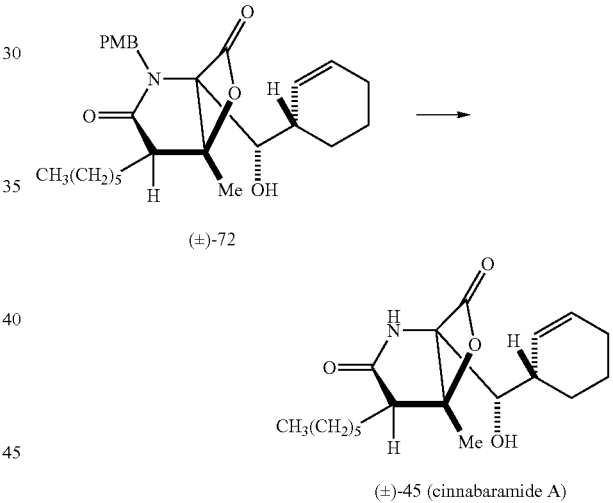

To a solution of alcohol (±)-72 (6.2 mg, 0.018 mmol), along with trace amounts of a diastereomer from the previous step, in CH$_3$CN (0.6 mL) was added an aqueous solution of CAN (146 mg, 0.266 mmol) in H$_2$O (0.2 mL) at 0° C. dropwise. After stirring at 0° C. for 4 h, the reaction mixture was diluted with EtOAc (25 mL) and washed with brine. The organic layer was dried over Na$_2$SO$_4$, filtered, and concentrated. The residue was purified by flash chromatography (1:5 EtOAc/CH$_2$Cl$_2$) to give cinnabaramide A (i)-45 (2.2 mg, 48%) as a white solid (dr>19:1, 500 MHz $^1$H NMR). A crystal suitable for X-ray analysis was obtained by slow evaporation from Et$_2$O with ~5% CH$_2$Cl$_2$: $R_f$=0.50 (33% EtOAc/hexanes); IR (neat) 3346, 1820, 1698 cm$^{-1}$; $^1$H NMR (500 MHz, DMSO-d$_6$) δ 8.96 (s, 1H), 5.84 (d, J=11.5 Hz, 1H), 5.75-5.77 (m, 1H), 5.56 (d, J=8.0 Hz, 1H), 3.70 (dd, J=8.0, 9.0 Hz, 1H), 2.46 (dd, J=6.0, 8.0 Hz, 1H), 2.29-2.36 (m, 1H), 1.92-1.98 (m, 1H), 1.81-1.88 (m, 1H), 1.77 (s, 3H), 1.24-1.75 (m, 13H), 0.91 (t, J=6.8 Hz, 3H); $^{13}$C NMR (125 MHz, DMSO-d$_6$) δ 177.0, 169.9, 129.5, 128.8, 87.2, 79.6, 70.1, 48.7, 38.7, 32, 29.8, 28.1, 26.3, 25.7, 25.6, 23.0, 22.0, 21.1, 15.0; LRMS (ESI) Calcd. for $C_{19}H_{29}NO_4$ [M+Li] 342, found 342.

Example 14

Synthesis of (±)rac-salinosporamide A

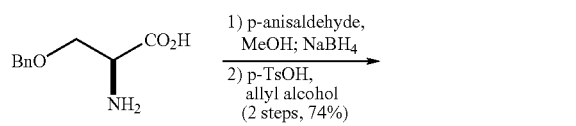

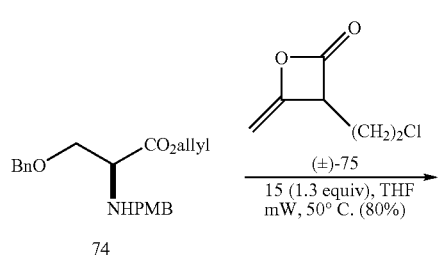

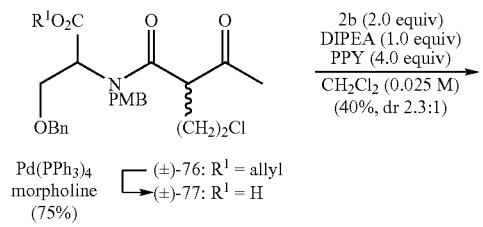

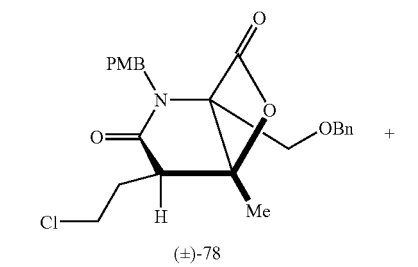

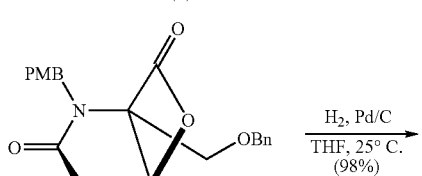

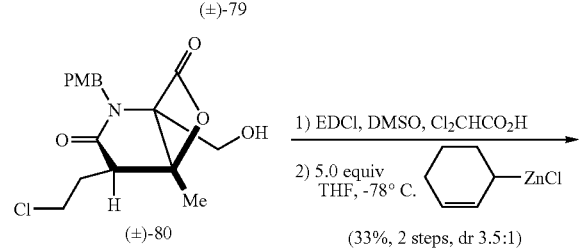

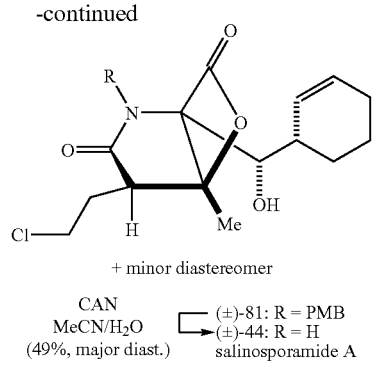

(S)-3-Benzyloxy-2-(4-methoxy-benzylamino)-propionic acid allyl ester (74)

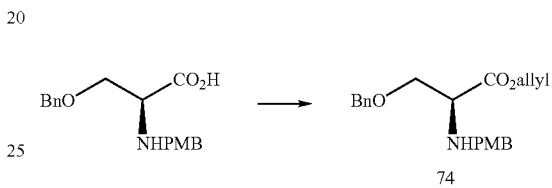

The suspension of O-benzyl-N-PMB serine (12.8 g, 40.6 mmol) and p-TsOH (9.65 g, 50.8 mmol) in allyl alcohol (30 mL) and benzene (100 mL) was stirred at reflux with a Dean-Stark apparatus until the calculated amount of water had been collected. The resulting solution was concentrated in vacuo, re-suspended in 5% aqueous $NaHCO_3$ (100 mL), the pH was adjusted to 9.0 with 1 M NaOH, and the product was extracted with $Et_2O$:EtOAc (1:1, 100 mL×3). The organic layer was washed with brine, dried over $Na_2SO_4$, and concentrated. The residue was purified by flash chromatography (1:6 EtOAc/hexanes) to give the desired allyl ester 74 (12.7 g, 88%) as a yellow oil. $R_f$=0.61 (33% EtOAc/hexanes); IR (neat) 1738, 1612 $cm^{-1}$; $^1H$ NMR (300 MHz, $CDCl_3$) δ 7.29-7.40 (m, 7H), 6.90 (d, J=8.4 Hz, 2H), 5.88-6.01 (m, 1H), 5.26-5.40 (m, 2H), 4.69 (dt, J=1.2, 5.7 Hz, 2H), 4.58 (d, J=12.3 Hz, 1H), 4.53 (d, J=12.0 Hz, 1H), 3.89 (d, J=12.6 Hz, 1H), 3.82 (s, 3H), 3.70-3.82 (m, 2H), 3.71 (d, J=13.2 Hz, 1H), 3.57 (t, J=4.8 Hz, 1H), 2.28 (s, 1H); $^{13}C$ NMR (75 MHz, $CDCl_3$) δ 172.9, 158.9, 138.0, 132.1, 131.8, 129.6, 128.4, 127.8, 127.7, 118.6, 113.9, 73.3, 71.2, 65.6, 60.5, 55.3, 51.5 LRMS (ESI) Calcd. for $C_{21}H_{26}NO_4$ [M+H] 356, found 356.

3-(2-Chloroethyl)-4-methyleneoxetan-2-one ((±)-75)

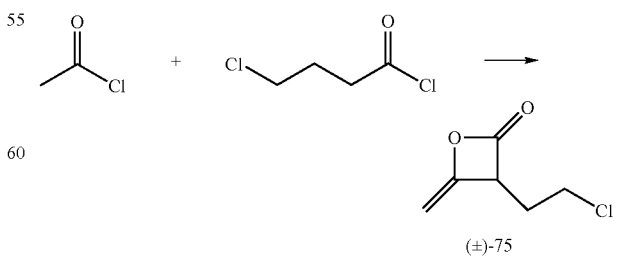

Prepared according to the representative procedure for ketene-heterodimerization using acetyl chloride (10.0 g, 0.127 mol), 4-chlorobutyrylchloride (15.0 g, 0.106 mol), and triethylamine (34.0 mL, 0.245 mol) in Et$_2$O (160 mL). Purification by flash chromatography on SiO$_2$ (95:5 pentane:Et$_2$O) gave ketene dimer (i)-75 (1.9 g, 12%) as a clear oil. R$_f$=0.67 (30% EtOAc/hexanes); IR (neat) 1860, 1694 cm$^{-1}$; $^1$H NMR (300 MHz, benzene-d$_6$) δ 4.41 (dd, J=2.1, 4.5 Hz, 1H), 3.80 (dd, J=1.5, 4.51H), 3.35 (t, J=7.8 Hz, 1H), 2.79-2.95 (m, 2H), 1.25-1.46 (m, 2H); $^{13}$C NMR (125 MHz, benzene-d$_6$) δ 167.4, 152.6, 85.7, 51.7, 40.9, 29.9; LRMS (CI) Calcd. for C$_6$H$_7$ClO$_2$ [M+H] 147, found 147.

3-Benzyloxy-2-[[2-(2-chloro-ethyl)-3-oxo-butyryl]-(4-methoxy-benzyl)-amino]-propionic acid allyl ester (76)

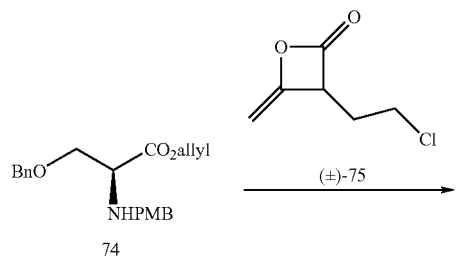

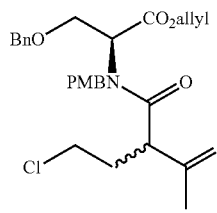

Prepared according to the representative procedure for ring opening of hetero-ketene dimers using allyl ester 74 (1.92 g, 5.40 mmol), 2-hydroxypyridine (642 mg, 6.75 mmol) in THF (14 mL), and ketene-dimer (O)-75 (990 mg, 6.75 mmol). The reaction mixture was stirred at 60° C. for 36 h and purification by flash chromatography on SiO$_2$ (1:4 EtOAc:Hexanes) gave a mixture of two diastereomers 76 (2.17 g, 80%) as a colorless oil.

76a: R$_f$=0.58 (40% EtOAc/Hexanes); $^1$H NMR (500 MHz, CDCl$_3$) δ 7.18-7.36 (m, 7H), 6.87 (d, J=8.0 Hz, 2H), 5.85-5.93 (m, 1H), 5.24-5.33 (m, 2H), 4.82 (d, J=16.5 Hz, 1H), 4.66 (d, J=17.0 Hz, 1H), 4.59-4.61 (m, 2H), 4.50 (dd, J=4.0, 8.5 Hz, 1H), 4.47 (d, J=11.5 Hz, 1H), 4.44 (d, J=11.5 Hz, 1H), 4.08 (dd, J=8.5, 10.0 Hz, 1H), 4.01 (dd, J=3.5, 10.0 Hz, 1H), 3.93 (dd, J=5.5, 8.5 Hz, 1H), 3.81 (s, 3H), 3.46-3.58 (m, 2H), 2.34-2.43 (m, 1H), 2.17-2.24 (m, 1H), 2.11 (s, 3H); LRMS (APCI) Calcd. for C$_{27}$H$_{32}$ClNO$_6$ [M+H] 502, found 502.
76b: R$_f$=0.50 (40% EtOAc/Hexanes); IR (neat) 1738, 1642, 1613 cm$^{-1}$; $^1$H NMR (500 MHz, CDCl$_3$) δ 7.25-7.36 (m, 7H), 6.89 (d, J=8.5 Hz, 2H), 5.86-5.94 (m, 1H), 5.24-5.33 (m, 2H), 4.88 (d, J=16.5 Hz, 1H), 4.69 (d, J=17.0 Hz, 1H), 4.57-4.66 (m, 3H), 4.50 (d, J=11.5 Hz, 1H), 4.45 (d, J=11.5 Hz, 1H), 4.03-4.06 (m, 2H), 3.92 (t, J=7.0 Hz, 1H), 3.82 (s, 3H), 3.57 (t, J=6.0 Hz, 2H), 2.34-2.41 (m, 1H), 2.15-2.21 (m, 1H), 1.97 (s, 3H); $^{13}$C (125 MHz, CDCl$_3$) δ 202.5, 170.9, 168.5, 159.5, 137.8, 131.8, 128.8, 128.7, 128.6, 128.0, 127.9, 119.1, 114.4, 73.6, 68.5, 66.3, 60.3, 55.5, 53.7, 52.7, 43.3, 31.9, 28.7.

3-Benzyloxy-2-[[2-(2-chloro-ethyl)-3-oxo-butyryl]-(4-methoxy-benzyl)-amino]-propionic acid (77)

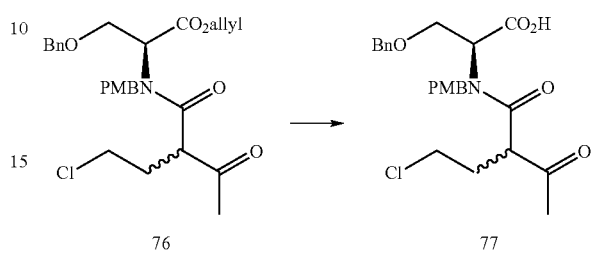

To a solution of allyl ester 76 (1.24 g, 2.47 mmol) in THF (20 mL) was added morpholine (646 mg, 7.41 mmol) and Pd(PPh$_3$)$_4$ (29 mg, 0.025 mmol) at ambient temperature. The reaction mixture was stirred at ambient temperature for 7 h and diluted with Et$_2$O (200 mL). The organic layer was washed with 0.2 N HCl and brine, dried over MgSO$_4$ and concentrated. The residue was purified by flash chromatography on SiO$_2$ (15:85 acetone:CH$_3$Cl) to give acid 77 (620 mg, 75%). Data provided for only one diastereomer: IR (neat) 1721, 1639 cm$^{-1}$; $^1$H NMR (300 MHz, CDCl$_3$) δ 7.20-7.40 (m, 7H), 6.89 (d, J=8.7 Hz, 2H), 4.82 (d, J=16.5 Hz, 1H), 4.70 (d, J=16.5 Hz, 1H), 4.48 (s, 2H), 4.41-4.45 (m, 1H), 4.00-4.10 (m, 3H), 3.84 (s, 3H), 3.50-3.65 (m, 2H), 2.20-2.50 (m, 2H), 2.13 (s, 3H); LRMS (ESI) Calcd. for C$_{24}$H$_{28}$ClNO$_6$ [M−H] 460, found 460.

1-(Benzyloxymethyl)-4-(2-chloroethyl)-2-(4-methoxybenzyl)-5-methyl-6-oxa-2-azabicyclo[3.2.0]heptane-3,7-dione ((±)-79):

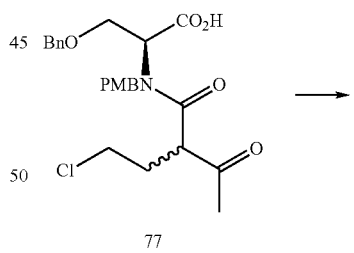

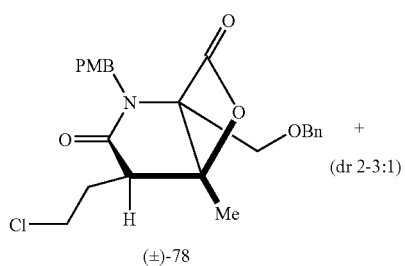

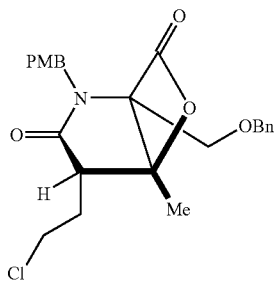

(±)-79

Prepared according to the representative procedure for bis-cyclization process using N-propyl-2-bromo pyridinium triflate (273 mg, 0.789 mmol), 4-pyrrolidinopyridine (223 mg, 1.56 mmol), Hünig's base (70 μL, 0.39 mmol), and keto-acid 77 (180 mg, 0.390 mmol) in CH$_2$Cl$_2$ (15 mL). Purification by flash chromatography (SiO$_2$, 10% EtOAc/hexanes) gave a mixture of two beta-lactones (±)-78 and (±)-79 (59 mg, 34%, dr=2:1, 500 MHz $^1$H NMR).

(±)-78: R$_f$=0.32 (20% EtOAc/hexanes); IR (neat) 1830, 1703 cm$^{-1}$; $^1$H NMR (500 MHz, CDCl$_3$) δ 7.32-7.36 (m, 3H), 7.13-7.15 (m, 4H), 6.80 (d, J=8.5 Hz, 2H), 4.73 (d, J=15.5 Hz, 1H), 4.31 (d, J=15.5 Hz, 1H), 4.17 (d, J=12.0 Hz, 1H), 4.13 (d, J=11.5 Hz, 1H), 4.01 (ddd, J=5.0, 7.5, 12.5 Hz, 1H), 3.77-3.81 (m, 1H), 3.77 (s, 3H), 3.73 (d, J=11.5 Hz, 1H), 3.57 (d, J=11.5 Hz, 1H), 2.91 (t, J=7.5 Hz, 1H), 2.31-2.38 (m, 1H), 2.10-2.16 (m, 1H), 1.72 (s, 3H); $^{13}$C NMR (125 MHz, CDCl$_3$) δ 173.8, 166.1, 159.2, 136.4, 129.2, 128.6, 128.5, 128.2, 128.0, 113.9, 83.4, 79.3, 73.5, 61.6, 55.2, 45.0, 44.3, 42.5, 28.4, 19.2; LRMS (ESI) Calcd. for C$_{24}$H$_{26}$ClNO$_5$ [M+H] 444, found 444.

4-(2-Chloro-ethyl)-1-hydroxymethyl-2-(4-methoxy-benzyl)-5-methyl-6-oxa-2-aza-bicyclo[3.2.0]heptane-3,7-dione ((±)-80)

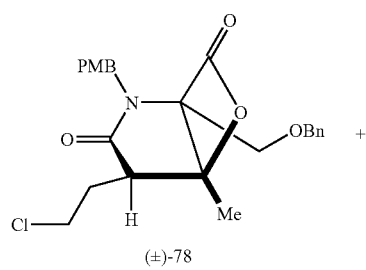

(±)-78

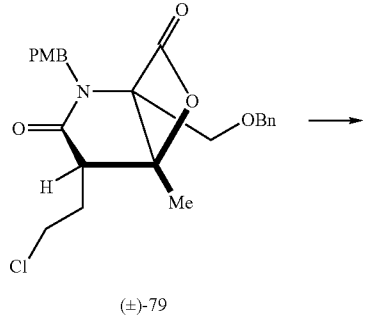

(±)-79

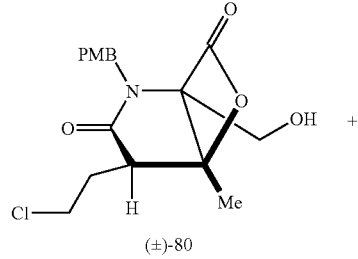

(±)-80

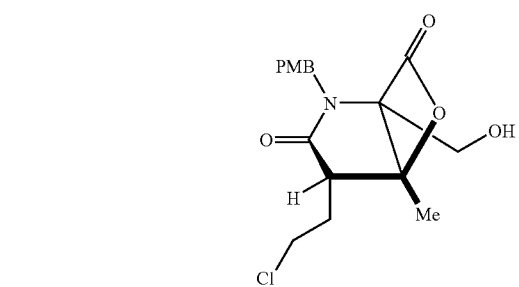

(±)-80b

Prepared according to the representative procedure for debenzylation using the mixture of beta-lactones (38 mg, 0.13 mmol, dr 6:1) and 10 wt % palladium on carbon (10 mg) in THF (5 mL) at ambient temperature for 5 h under H$_2$ atmosphere. Purification by flash chromatography (1:40 EtOAc/CH$_2$Cl$_2$) gave the desired alcohol (±)-80 along with the minor diastereomer (29.9 mg, 98%, dr 6:1) as a waxy solid. Further purification allowed enrichment to ~10-19:1 dr (500 MHz $^1$H NMR).

(±)-80: R$_f$=0.29 (4.8% EtOAc/CH$_2$Cl$_2$); IR (neat) 3449, 1831, 1687 cm$^{-1}$; $^1$H NMR (500 MHz, CDCl$_3$) δ 7.30 (d, J=8.5 Hz, 2H), 6.89 (d, J=8.5 Hz, 2H), 5.13 (d, J=15.0 Hz, 1H), 4.06 (d, J=15.5 Hz, 1H), 4.03 (ddd, J=5.5, 7.5, 12.5 Hz, 1H), 3.92 (dd, J=9.0, 13.5 Hz, 1H), 3.85 (dd, J=4.5, 13.5 Hz, 1H), 3.80 (s, 3H), 3.78-3.82 (m, 1H), 2.94 (t, J=7.0 Hz, 1H), 2.32-2.38 (m, 1H), 2.01-2.18 (m, 1H), 1.77 (s, 3H), 0.86 (dd, J=5.0, 9.5 Hz, 1H); $^{13}$C NMR (125 MHz, CDCl$_3$) δ 174.2, 166.7, 159.6, 129.0, 128.7, 114.7, 83.6, 80.2, 55.3, 55.1, 44.9, 44.1, 42.4, 28.4, 19.1; LRMS (ESI) Calcd. for C$_{17}$H$_{20}$ClNO$_5$ [M+H] 354, found 354.

4-(2-Chloro-ethyl)-1-(cyclohex-2-enyl-hydroxymethyl)-2-(4-methoxy-benzyl)-5-methyl-6-oxa-2-aza-bicyclo[3.2.0]heptane-3,7-dione ((±)-81):

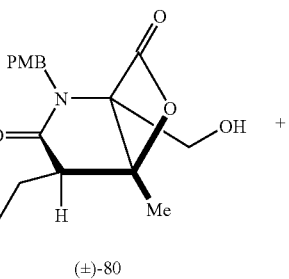

(±)-80

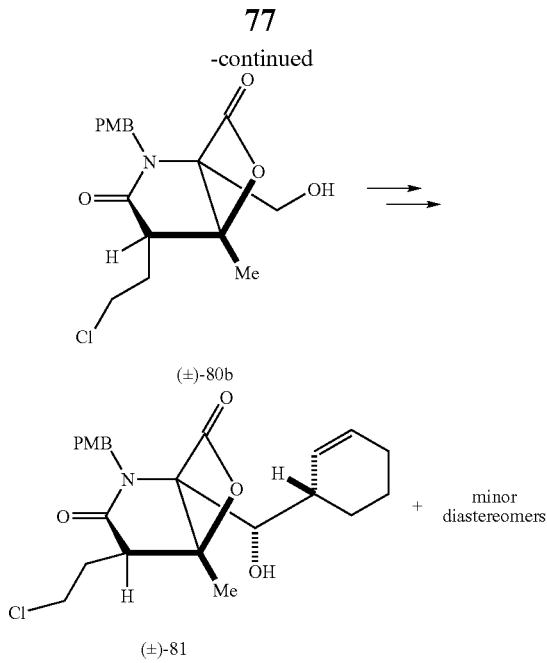

(±)-80b (±)-81

To a solution of diastereomeric alcohols, (±)-80 plus minor diastereomer (29 mg, 0.082 mmol, dr>10:1), in DMSO/toluene (0.8 mL/0.8 mL) was added EDCI (79 mg, 0.41 mmol), followed by dichloroacetic acid (14 µL, 0.16 mmol) at ambient temperature. The reaction mixture was stirred at ambient temperature for 2 h and diluted with EtOAc (50 mL). The organic layer was washed with 0.1 N HCl, and brine, dried over MgSO$_4$, filtered, and concentrated. The residue was used for the next step without further purification due to some instability of resulting aldehyde to column chromatography.

A solution of tri-n-butyl-2-cyclohexenyltin (140 mg, 0.377 mmol) in THF (0.7 mL) was treated with n-BuLi (2.5 M in hexanes, 133 µL, 0.333 mmol) at −78° C. After 30 min, ZnCl$_2$ (0.5 M in THF, 0.77 mL, 0.39 mmol) was added and following an additional 30 min, a solution of the crude aldehyde in THF (1.3 mL) was slowly added to the freshly prepared zinc reagent 46. The resulting mixture was stirred at −78° C. for 2.5 h, quenched with water and diluted with EtOAc (50 mL). The organic layer was washed with saturated NH$_4$Cl and brine, dried over Na$_2$SO$_4$, filtered, and concentrated. The residue was purified by flash chromatography (1:6 EtOAc/hexanes) to give a mixture of predominantly two diastereomers (12 mg, 33%, dr 3.5:1+trace minor diasts., 500 MHz $^1$H NMR) as a colorless oil which was carried directly to the next step without further characterization. The major diastereomer (±)-81 was confirmed to possess the correct relative stereochemistry following subsequent conversion to salinosporamide A (below): R$_f$=0.64 (40% EtOAc/Hexanes); IR (neat) 3467, 1828, 1692 cm$^{-1}$; LRMS (ESI) Calcd. for C$_{23}$H$_{28}$ClNO$_5$ [M+Li] 440, found 440.

Rac-Salinosporamide A, 4-(2-Chloro-ethyl)-1-(cyclohex-2-enyl-hydroxy-methyl)-5-methyl-6-oxa-2-aza-bicyclo[3.2.0]heptane-3,7-dione ((±)-44):

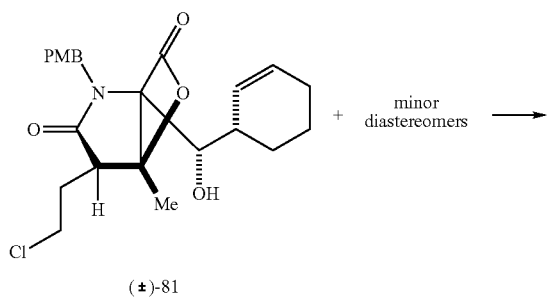

(±)-81

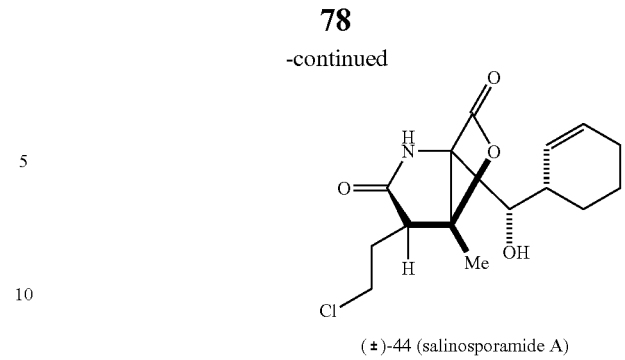

(±)-44 (salinosporamide A)

To a mixture of diastereomer (±)-81 (10 mg, 0.023 mmol, dr=3.5:1) in CH$_3$CN (0.1 mL) was added an aqueous solution of CAN (63 mg, 0.12 mmol) in H$_2$O (25 µL) at 0° C. After stirring at 0° C. for 2 h, the reaction mixture was diluted with EtOAc (25 mL) and washed with brine. The organic layer was dried over anhydrous MgSO$_4$, filtered, and concentrated. The residue was purified by flash chromatography (1:10 to 1:4 EtOAc/CH$_2$Cl$_2$) providing diastereomerically pure salinosporamide A (±)-44 (3.5 mg, 49%) as a white solid (dr>19:1, 500 MHz $^1$H NMR). A crystal suitable for X-ray analysis was obtained by slow evaporation from CH$_2$Cl$_2$ with ~5% CH$_3$CN: R$_f$=0.09 (5% EtOAc/CH$_2$Cl$_2$); IR (neat) 3413, 1821, 1700 cm$^{-1}$; $^1$H NMR (500 MHz, pyridine-d$_5$) δ 10.63 (s, 1H), 6.42 (d, J=10.5 Hz, 1H), 5.86-5.90 (m, 1H), 4.26 (t, J=9.0 Hz, 1H), 4.13 (dt, J=7.5, 10.5 Hz, 1H), 4.02 (dt, J=7.0, 10.5 Hz, 1H), 3.18 (t, J=7.0 Hz, 1H), 2.82-2.89 (m, 1H), 2.45-2.52 (m, 1H), 2.27-2.36 (m, 2H), 2.07 (s, 3H), 1.89-1.95 (m, 2H), 1.66-1.72 (m, 1H), 1.35-1.40 (m, 1H) 1H was overlapped with H$_2$O; $^{13}$C NMR (125 MHz, pyridine-d$_5$) δ 176.9, 169.4, 129.1, 128.7, 86.3, 80.4, 71.0, 46.2, 43.3, 39.3, 29.0, 26.5, 25.4, 21.7, 20.0; LRMS (ESI) Calcd. for C$_{15}$H$_{20}$ClNO$_4$ [M+Li] 314, found 314.

ORTEP Plot of the X-Ray Structure of Rac-Salinosporamide A ((±)-44)

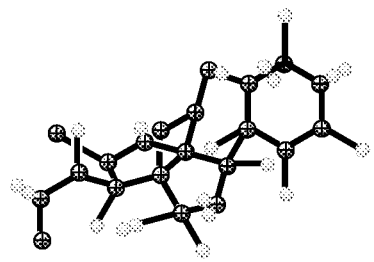

Example 15

Enantioselective Synthesis of (±)-Salinosporamide A ((±)-44)

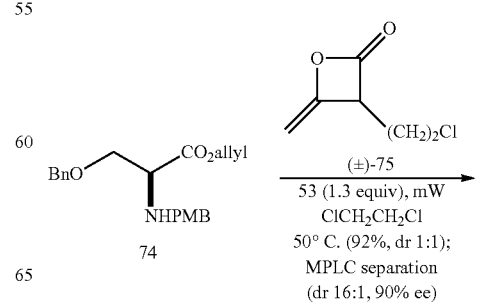

79

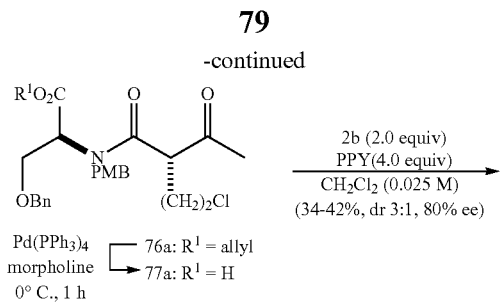

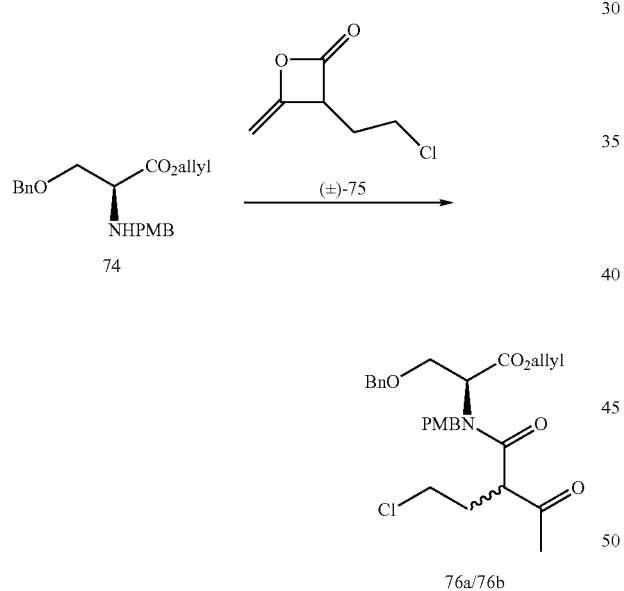

3-Benzyloxy-2-[[2-(2-chloro-ethyl)-3-oxo-butyryl]-(4-methoxy-benzyl)-amino]-propionic acid allyl ester (76)

To a solution of (S)-allyl ester 74 (300 mg, 0.844 mmol) and 2-hydroxypyridine (40 mg, 0.422 mmol) in 1,2-dichloroethane (3 mL) was added ketene-dimer (±)-75 (186 mg, 1.27 mmol). The reaction mixture was stirred at 50° C. for 1 h under microwave irradiation and the solvent was evaporated under reduced pressure. The combined residues from 6 batches were purified by flash chromatography (1:4 EtOAc/hexanes) to afford a 1:1 mixture of diastereomeric keto esters 76 as a colorless oil. Each diastereomer could be enriched up to dr 16:1 (76a, less polar on TLC) or 1:10 (76b, more polar on TLC) by MPLC separation (1:5 EtOAc/hexanes). Enantiomeric purity of 76 was determined to be ~92% ee by chiral HPLC analysis.

80

3-Benzyloxy-2-[[2-(2-chloro-ethyl)-3-oxo-butyryl]-(4-methoxy-benzyl)-amino]-propionic acid (77a)

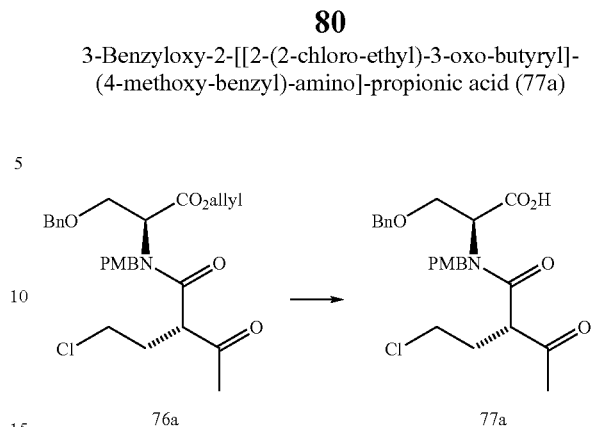

To a solution of allyl ester 76a (800 mg, 1.59 mmol, dr 10:1) in THF (27 mL) was added morpholin (0.40 mL, 4.8 mmol) and Pd(PPh$_3$)$_4$ (98 mg, 5 mol %) at −5° C. The reaction mixture was stirred at −5° C. for 2 h and diluted with Et$_2$O (100 mL). The organic layer was washed with 2 N HCl and brine, dried over MgSO$_4$ and concentrated to give the desired acid 77a (615 mg, 82%, dr 8:1). Major diastereomer of acid 77a could be enriched up to dr 11:1 by flash chromatography on SiO$_2$.

1-(Benzyloxymethyl)-4-(2-chloroethyl)-2-(4-methoxybenzyl)-5-methyl-6-oxa-2-azabicyclo[3.2.0]heptane-3,7-dione (78):

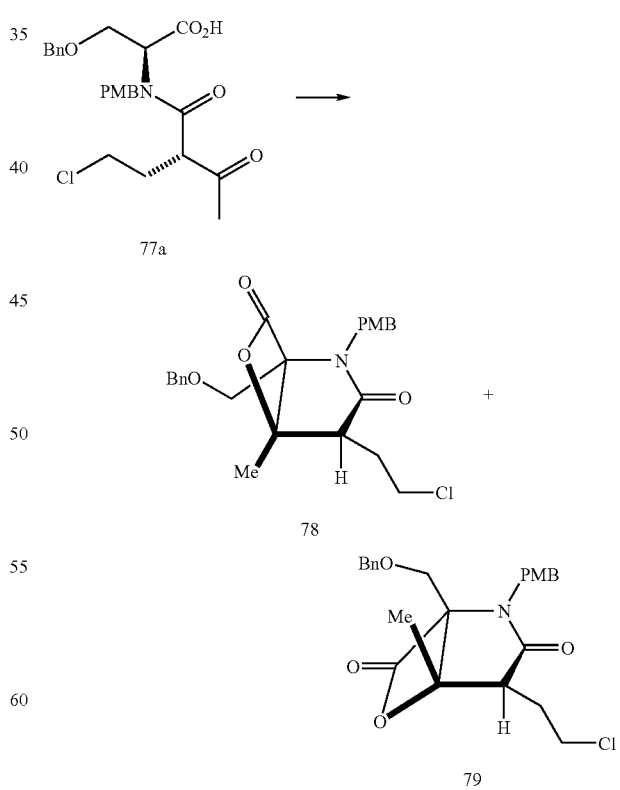

Prepared according to the representative procedure for bis-cyclization process using N-propyl-2-bromo pyridinium triflate (300 mg, 0.857 mmol), 4-pyrrolidinopyridine (380 mg, 2.66 mmol) and keto-acid 77a (160 mg, 0.346 mmol, dr 9:1) in CH$_2$Cl$_2$ (18 mL). Purification by flash chromatography (2:3, EtOAc/hexanes) gave a mixture of two β-lactones 78 and 79 (59 mg, 41%, dr=3:1) as a yellow oil. Enantiomeric purity of 78 was determined to be 80% ee by chiral HPLC analysis (not shown). Note: Studies of the asymmetric version revealed that rapid chromatography with a more polar solvent system (e.g. 2:3, EtOAc/hexanes) minimized loss of beta-lactone 78 on the column.

(±)-Salinosporamide A:

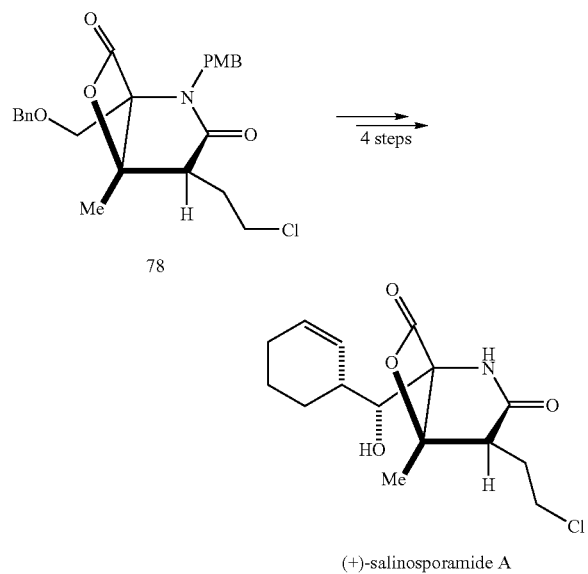

(+)-salinosporamide A beta-Lactone 78 was converted to salinosporamide A via an identical 4-step sequence as described above for the racemic series. Synthetic salinosporamide A: [α]$_D$+42.6 (c=0.22, MeOH). Natural (−)-Salinosporamide A: [α]$_D$−72.9 (c=0.5, MeOH).

In a similar manner, using the other diastereomer 77b, (−)-salinosporamide could be obtained.

Example 16

Representative HPLC Analyses of Certain Beta-Lactones Described Herein

The figure represents an HPLC analysis of two beta-lactones following bis-cyclization.

HPLC Analysis of β-Lactones following Bis-Cyclization

Example 17

Non-Limiting Examples Of (a) hybrid-compounds of salinosporamide A and belactosin;
(b) interrogation the C3-Me group pocket (Asp17, Thr21, Tyr168) of proteasome 20S using compounds accessible by methods of the present invention;
(c) interrogating the hydrophobic pocket (Ala27, Ala20, Val31) of proteasome 20S: compounds accessible by methods of the present invention designed based on inhibitor-binding mode and overlay of crystal structures of salinosporamide and homobelactosin C bound to the yeast 20S proteasome (a)

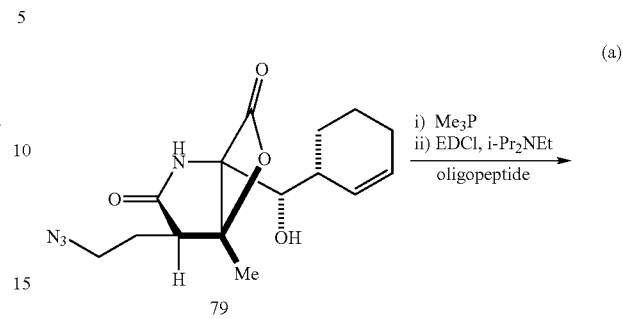

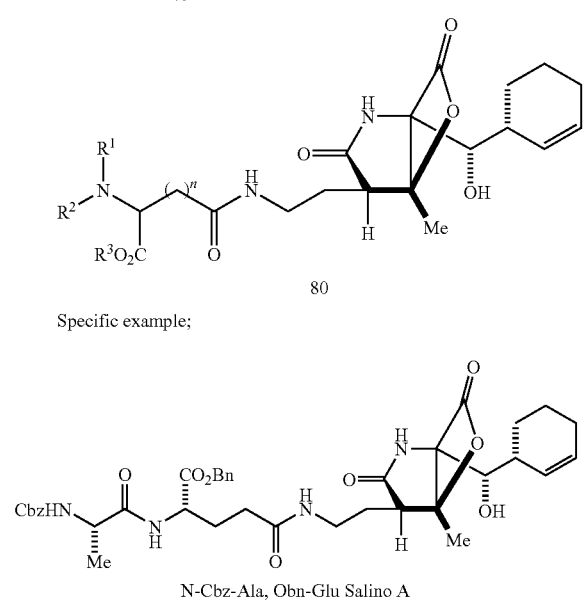

Specific example;

N-Cbz-Ala, Obn-Glu Salino A
81

(b)

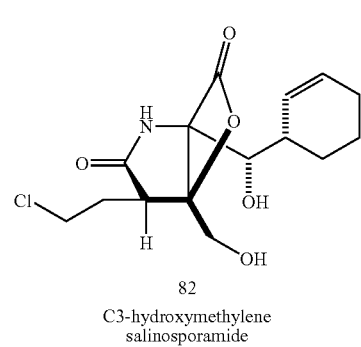

82
C3-hydroxymethylene salinosporamide

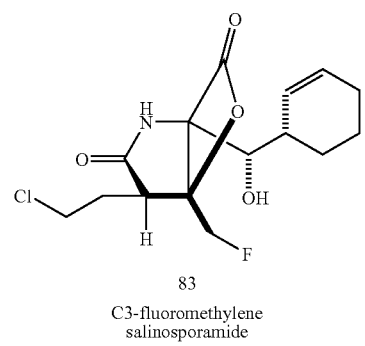

83
C3-fluoromethylene salinosporamide (c)
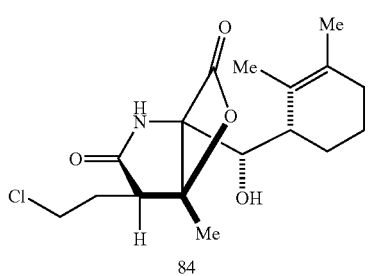
84
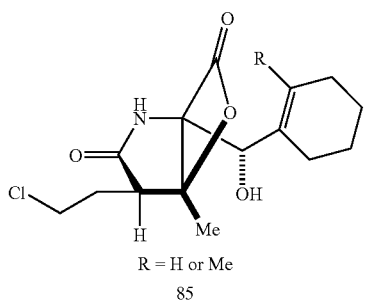
R = H or Me
85
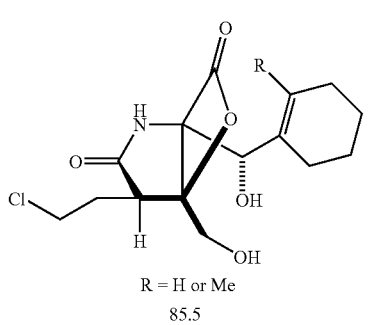
R = H or Me
85.5
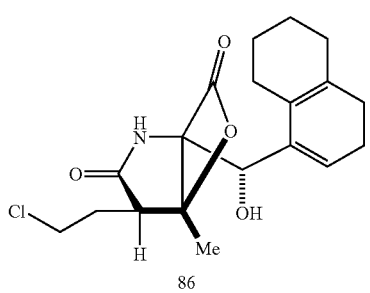
86
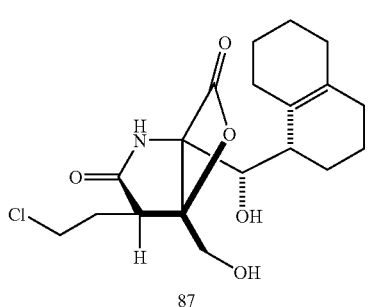
87
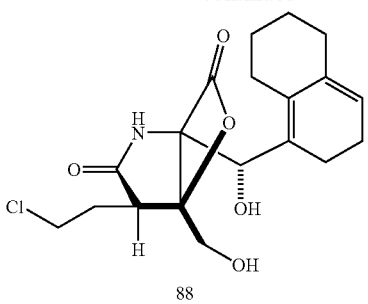
88
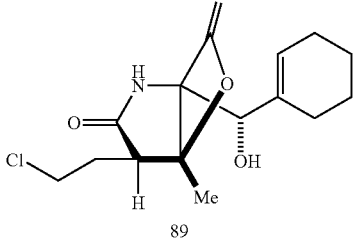
89
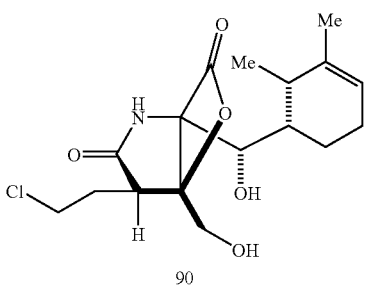
90
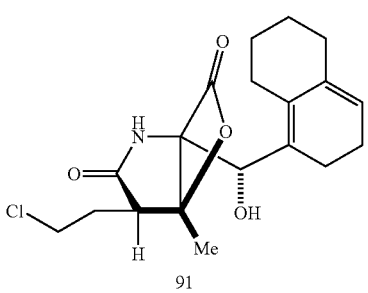
91
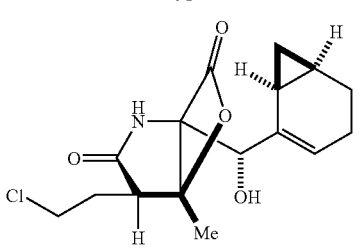
92
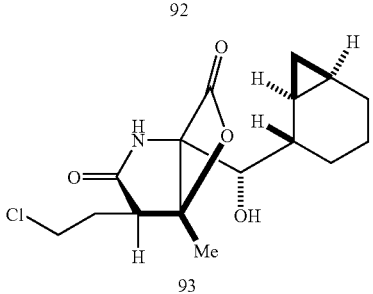
93

Example 18

Non-Limiting Examples of Compounds Accessible by Methods of the Present Invention (94)

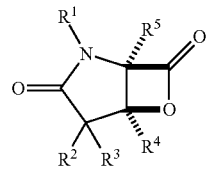

R¹ = H, alkyl, para-methoxy benzyl, benzyloxymethyl, para-tolylsulfonyl
R², R³ = H, C1-C6 alkyl, cycloalkyl, substituted alkyl with halogen, hydroxy, alkoxy, siliyloxy, aryl and sulfonyl
R⁴ = H, C1-C7 alkyl, aryl, cycloalkyl, substituted alkyl with halogen, hydroxy, alkoxy, silyloxy, aryl and sulfonyl
R⁵ = H, alkyl, aryl, cycloalkyl, substituted alkyl with halogen, hydroxy, alkoxy, silyloxy, aryl, aminocarbonyl, amino, alkylamino, dialkylamino, and/or sulfonyl (95)

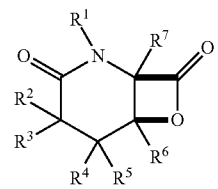

R¹ = H, alkyl, para-methoxy benzyl, benzyloxymethyl, para-tolylsulfonyl
R², R³, R⁴, R⁵ = H, C1-C6 alkyl, cycloalkyl, and substituted alkyl with halogen, hydroxy, alkoxy, siliyloxy, aryl and sulfonyl
R⁶ = H, C1-C7 alkyl, aryl, cycloalkyl, and substituted alkyl with halogen, hydroxy, alkoxy, silyloxy, aryl and sulfonyl
R⁷ = H, alkyl, aryl, cycloalkyl, substituted alkyl with halogen, hydroxy, alkoxy, silyloxy, aryl, aminocarbonyl, amino, alkylamino, dialkylamino, and/or sulfonyl

96

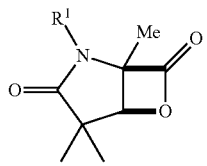

97

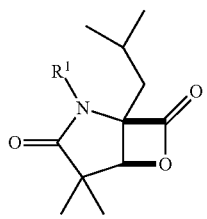

98

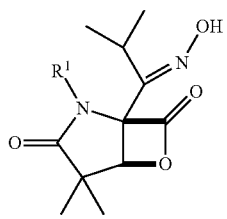

99

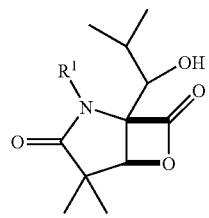

100

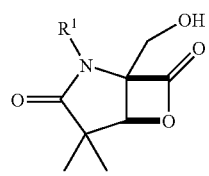

101

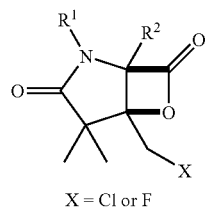

X = Cl or F
R² = alkyl, aryl

102

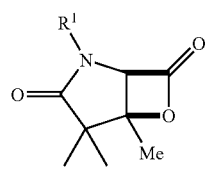

103

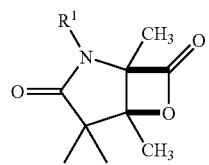

104

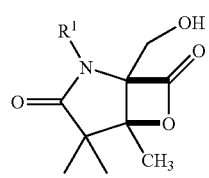

105

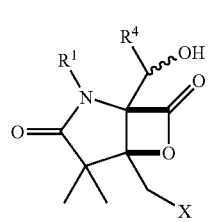

X = Cl or F
R² = alkyl, aryl

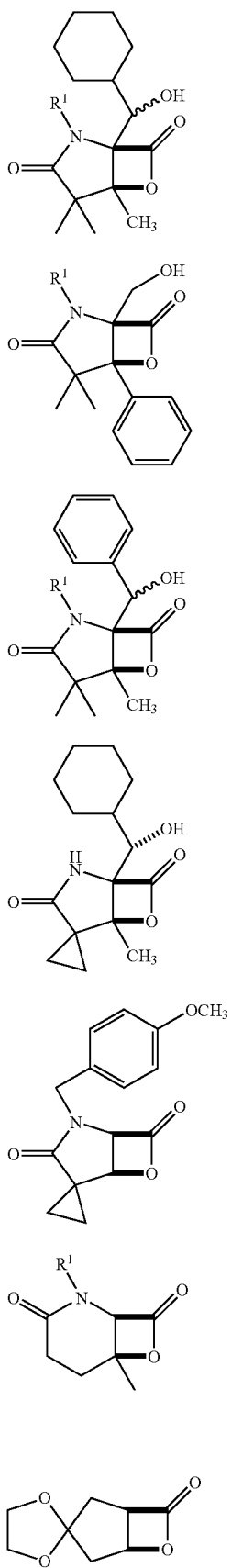
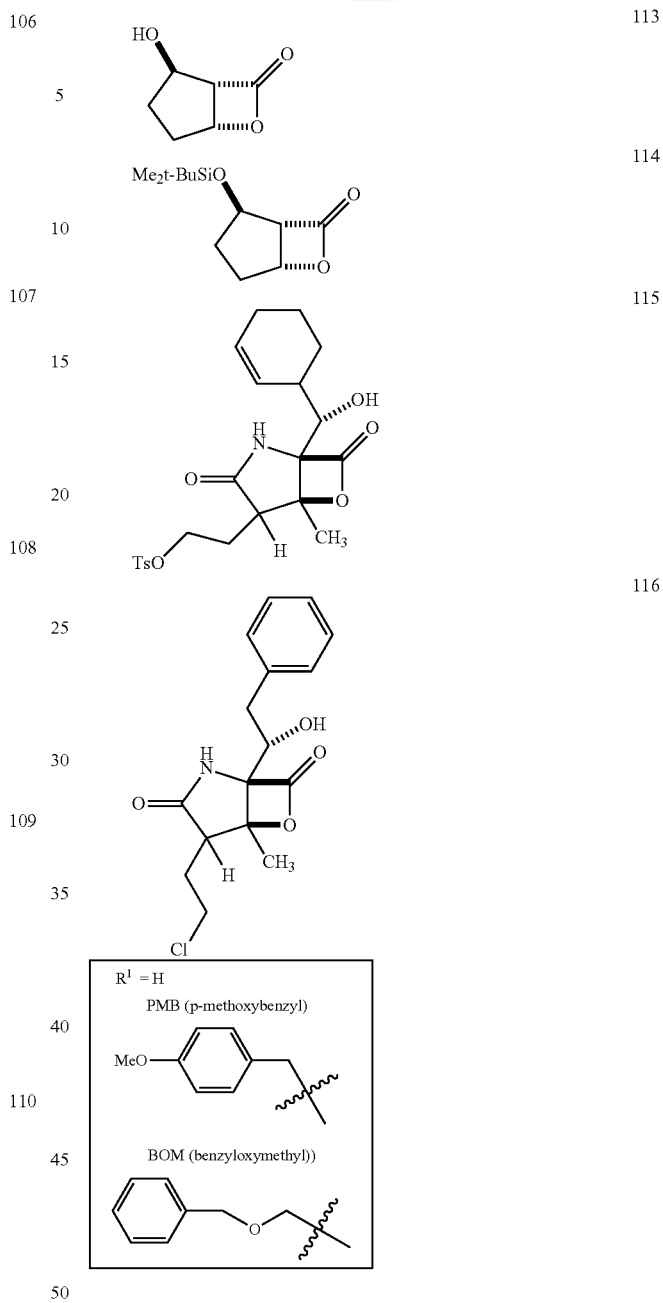

All of the compositions and/or methods disclosed and claimed in this specification can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Provisional Application entitled, "Novel Belactosin Derivatives as Therapeutic Agents/Biological Probes and Their Synthesis," by Daniel Romo, Sung Wook Cho, Jeffrey W. Smith and Robyn D. Richardson, filed Jul. 9, 2007.
U.S. Provisional Application Ser. No. 60/819,444
Adams et al., *Cancer Res.* 59:2615-22, 1999.
Allen et al., *J. Chem. Soc. Perkin Trans.*, 2:S1, 1987.
Akaishi et al., *Brain Res.*, 722:139-144, 1996.
Behenna and Stoltz, *J. Am. Chem. Soc.*, 126:15044-15045, 2004.
Browne, *FASEB J.*, 20:2027-35, 2006.
Bundgaard, H., Design of Prodrugs, pp. 7-9, 21-24, Elsevier, Amsterdam 1985.
Bundgaard, *Drugs of the Future*, 16:443-458, 1991.
Calter et al., *Org. Lett.*, 7:1809, 2005.
Chakravarty et al., *Proc. Natl. Acad. Sci. USA*, 101:15567-72, 2004.
Cortez et al., *J. Am. Chem. Soc.*, 123:7945-7946, 2001.
Duffy et al., *J. Am. Chem. Soc.* 127:16754-16755, 2005.
Enders et al., *ACIE*, 41:1743-1645, 2002.
FluoProbes® BioDirectory of Fluorescence.
Getzler et al., *Am. Chem. Soc.*, 124:1174, 2002.
Gingerich and Jennings, *J. Org. Chem.*, 48:2606-2608, 1983.
Greene & Wuts, In: *Protective Groups in Organic Synthesis*, 3rd ed., John Wiley & Sons, New York, N.Y., 1999.
Groll et al., *PNAS*, 103:4576, 2006.
Gu and Snider, *Org. Lett.* 5:4385, 2003.
*Handbook of Pharmaceutical Salts: Properties, Selection and Use*, P. H. Stahl & C. G. Wermuth eds., Verlag Helvetica Chimica Acta, 2002.
Heinrich et al., *Angew. Chem. Int. Ed.* 42:482, 2003.
Henry-Riyad et al., *Org. Lett.* 8: 4363, 2006.
Hirano et al., *Methods Enzymol.* 399:227-240, 2005.
Hoye and Wang, *J. Am. Chem. Soc.* 127:6950, 2005.
Johannsen et al., *J. Org. Chem.*, 70:8332, 2005.
Kigoshi et al., *Org. Lett.* 5:957, 2003.
Krafft and Holton, *J. Org. Chem.*, 49:3669-3670, 1984.
Kridel et al., *Cancer,* 64:2070-5, 2004.
Lall et al., *J. Org. Chem.*, 67:1536, 2002.
Levenfors et al., *Soil Biol. Biochem.* 36:677, 2004.
Lecka et al., *Chem. Rev.*, 103:2985-3012, 2003.
Lowe and Vederas, *Org. Prep. Proceed. Int.*, 27:305, 1995.
Ma et al., *Org. Lett.* 9:2143, 2007.
Maruoka et al., *J. Am. Chem. Soc.*, 110:3588-3599, 1988.
Mellgren, *J. Biol. Chem.*, 272:29899-903, 1997.
Michel et al., *J. Chem. Soc. Perkin Trans. I*, 1935-1936, 1993.
Molecular Probes, The Handbook—A Guide to Fluorescent Probes and Labeling Technologies, 10$^{th}$ Ed., 2005.
Oh et al., *J. Org. Chem.* 70:2835-2838, 2005.
Pizer et al., *Cancer Res.*, 56:745-51, 1996.
Pommier and Pons, *Synthesis*, pp 441-459, 1993.
Protective Groups in Organic Synthesis, 3rd Ed., Greene and Wuts (Eds.), John Wiley & Sons, NY, 1999.
Ramiandrasoa et al., Vert, *M. Polym. Bull.*, 30:501-508, 1993.
Remington's Pharmaceutical Sciences, 18th Ed. Mack Printing Company, 1990.
Rieth et al., *J. Am. Chem. Soc.*, 124:15239, 2002.
Rovis, *J. Am. Chem. Soc.*, 124:10298-10299, 2002.
Rovis, *Synlett.*, 1934-1936, 2003.
Shoair and Mohamed, *Synth. Comm.*, 36:59-64, 2006.
Smith and March, March's Advanced Organic Chemistry, Reactions, Mechanisms, and Structure, 5$^{th}$ ed., Wiley Interscience, New York, 2001.
Strobel et al., *Microbiology* 145:3557, 1999.
Takada et al., *Tetrahedron Lett.* 40:6309, 1999.
Thaning et al., *Soil Biol. Biochem.* 33:1817, 2001.
Ueda and Yumin, *Tetrahedron Lett.* 40:6305, 1999.
Ugai et al., *J. Biochem. (Tokyo)*, 113:754-768, 1993.
Umemura et al., *J. Org. Chem.*, 54:2374-2383, 1989.
Wang et al., *Heterocycles*, 64:605, 2004.
Wilson and Fu, *Angew. Chem. Int.* 116:6518, 2004.
Wilson et al., *Chem. Int. Ed.*, 43:6358, 2004.
Wynberg and Staring, *J. Am. Chem. Soc.*, 104:166-168, 1982.
Wynberg and Staring, *J. Org. Chem.*, 50:1977-1979, 1985.
Wynberg, *Stereochem.*, 16:87-130, 1986.
Yang and Romo, *Tetrahedron*, 55:6403, 1999.
Zhu et al., *J. Am. Chem. Soc.*, 126:5352, 2004.

What is claimed is:

1. A method of synthesizing a lactam-fused beta-lactone, comprising reacting a carbonyl/carboxylic acid difunctionalized amide with an activating agent, a base and a nucleophilic promoter, wherein the carbonyl/carboxylic acid difunctionalized amide is further defined as a compound of formula (I) of (a) or a compound listed in (b), wherein (a) is as follows:

(a)

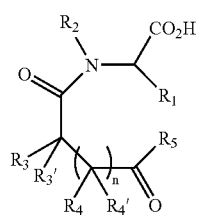

(I)

wherein:

$R_1$ is selected from the group consisting of H, alkyl, alkenylalkyl, aryl, -alkyl-protected hydroxy, halo, amino, protected amine, aminocarbonyl, alkylamino and sulfonyl;

$R_2$ is selected from the group consisting of H, alkyl, aryl, —OH and amine protecting group;

$R_3$, $R_3'$, $R_4$, $R_4'$, and $R_5$ are each independently selected from the group consisting of H, alkyl, aryl and aralkyl;

or $R_3$ and $R_3'$ together form a cycloalkyl; and n=1;

and optical isomers thereof; and wherein (b) is as follows:

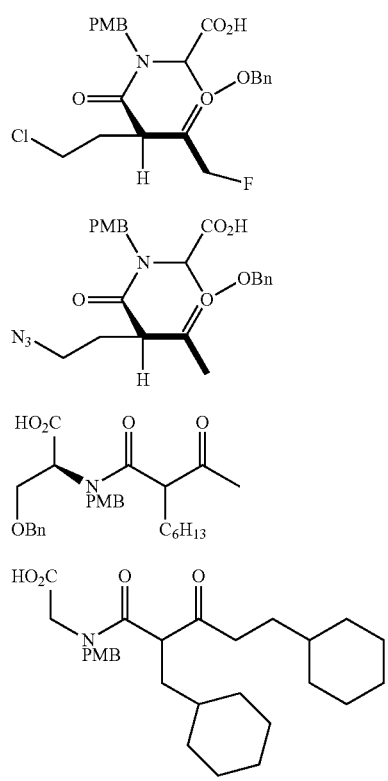

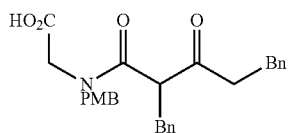

(E)

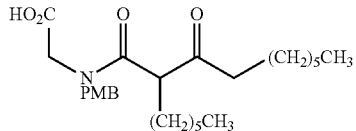

(F)

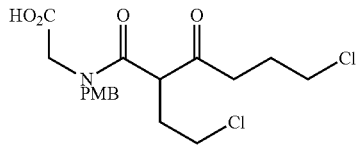

(G)

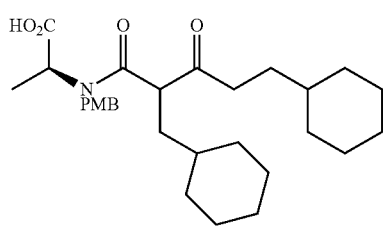

(H)

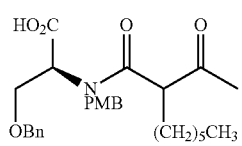

(I)

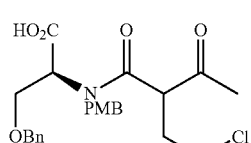

(J)

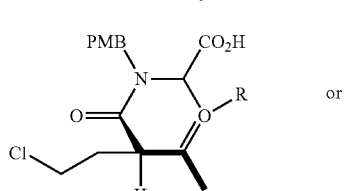

(K) or

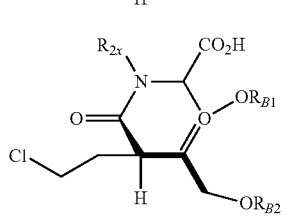

(L)

wherein:

R is H, alkyl, alkoxy, acyl, or protected hydroxy, $R_{2x}$ is an amine protecting group, $R_{B1}$ is a hydroxy protecting group, and $R_{B2}$ is a hydroxy protecting group, and optical isomers thereof;

to provide a lactam-fused beta-lactone.

2. The method of claim 1, wherein $R_1$ is alkyl.

3. The method of claim 1, wherein $R_3$ is H or alkyl.

4. The method of claim 1, wherein $R_5$ is $CH_2OH$.

5. The method of claim 1, wherein the carbonyl/carboxylic acid difunctionalized amide is of the following formula:

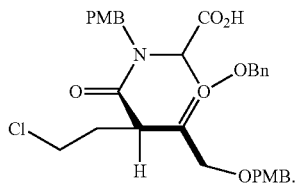

6. The method of claim 1, wherein the activating agent is selected from the group consisting of Mukaiyama's reagent and derivatives thereof, oxalyl chloride, thionyl chloride, aryl sulfonyl halides, an acid chloride, a chloroformate, dicyclohexylcarbodiimide and derivatives, $SOCl_2$ and $P(O)Cl_3$.

7. The method of claim 6, wherein the activating agent is Mukaiyama's reagent or derivatives thereof.

8. The method of claim 7, wherein the Mukaiyama's reagent or derivatives thereof is selected from the group consisting of compounds of formula (II):

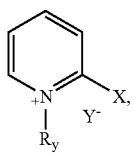

(II)

wherein $R_y$ is alkyl, X is halogen and Y is a counterion.

9. The method of claim 8, wherein $R_y$ is methyl or n-propyl, X is chloro or bromo, and the Y is triflate or iodide.

10. The method of claim 1, wherein the base is selected from the group consisting of a trialkylamine, a triarylamine, a trialkylarylamine, a substituted pyridine, an inorganic base and a proton sponge.

11. The method of claim 10 wherein the trialkylamine is selected from the group consisting of i-$Pr_2NEt$, $Et_3N$, i-$Bu_3N$ and i-$Pr_3N$.

12. The method of claim 10, wherein the substituted pyridine is selected from the group consisting of a 2,6-dialkyl pyridine, a 2,6-diaryl pyridine and a 2,6-dialkylaryl pyridine.

13. The method of claim 12, wherein the 2,6-dialkyl pyridine is selected from the group consisting of 2,6-dimethylpyridine and 2,6-di-t-butylpyridine.

14. The method of claim 1, wherein the nucleophilic promoter is selected from the group consisting of a nitrogen-containing nucleophile, a phosphine-containing nucleophile, and a carbene-containing nucleophile.

15. The method of claim 14, wherein the nitrogen-containing nucleophile is a pyridine-based nucleophile.

16. The method of claim 1, wherein the nucleophilic promoter is selected from the group consisting of dimethylaminopyridine, 4-pyrrolidinopyridine,

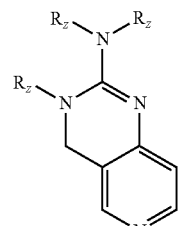

(3bb)

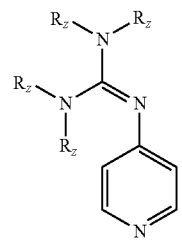

(3cc)

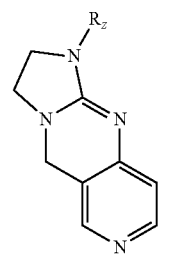

(3dd)

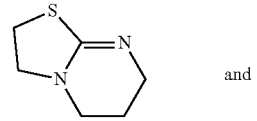

(3hh)

and

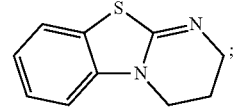

(3jj)

;

wherein:
each $R_z$ is independently selected from the group consisting of hydrogen, alkyl, and aryl, and any combination of one or more of these groups.

17. The method of claim 16, wherein each $R_z$ is independently selected from the group consisting of hydrogen, methyl, phenyl, and benzyl.

18. The method of claim 1, wherein the carbonyl/carboxylic acid difunctionalized amide is a compound listed in (b).

19. The method of claim 18, wherein a compound of formula (IV) is generated as an intermediate following biscyclization of a compound listed in (b):

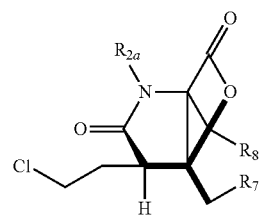

(IV)

wherein:
R$_{2a}$ is an amine protecting group;
R$_7$ is H or a protected hydroxy; and
R$_8$ is —CH$_2$-protected hydroxy.

20. The method of claim 19, wherein
R$_{2a}$ is p-methoxybenzyl (PMB);
R$_7$ is H, O-benzyl; and
R$_8$ is —CH$_2$—OPMB or —CH$_2$—O-dimethoxybenzyl.

21. The method of claim 1, wherein the lactam-fused beta-lactone is a compound of formula (VIII):

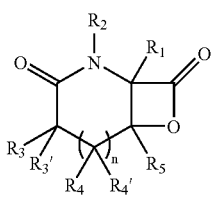
(VIII)

wherein:
R$_1$ is selected from the group consisting of H, alkyl, alkenylalkyl, aryl, -alkyl-protected hydroxy, halo, amino, protected amine, aminocarbonyl, alkylamino, and sulfonyl;
R$_2$ is selected from the group consisting of H, alkyl, aryl, —OH and an amine protecting group;
R$_3$, R$_3$', R$_4$, R$_4$', and R$_5$ are each independently selected from the group consisting of H, alkyl, aryl and aralkyl;
or R$_3$ and R$_3$' together form a cycloalkyl; and
n=1;
and optical isomers thereof.

22. The method of claim 1, wherein the carbonyl/carboxylic acid difunctionalized amide is
a compound of formula (I) of (a), wherein: R$_1$ is -alkyl-protected hydroxy or protected amine, or R$_2$ is an amine protecting group; or
a compound of (b), wherein R$_{2x}$ is an amine protecting group, R$_{B1}$ is a hydroxy protecting group, or R$_{B2}$ is a hydroxy protecting group,
wherein the method further comprises a step of removing a hydroxy protecting group or an amine protecting group.

23. The method of claim 1, further comprising subjecting the lactam-fused beta-lactone to acid- or base-hydrolysis to produce a hydroxy acid.

24. The method of claim 23, wherein the hydroxy acid is reacted with cysteine or glutathione to produce a compound comprising a thioester.

25. The method of claim 1, wherein the lactam-fused beta-lactone is further transformed into a compound selected from the group consisting of:

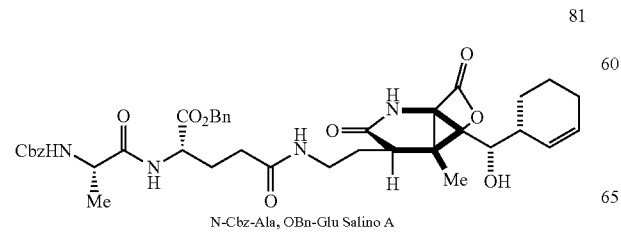
N-Cbz-Ala, OBn-Glu Salino A

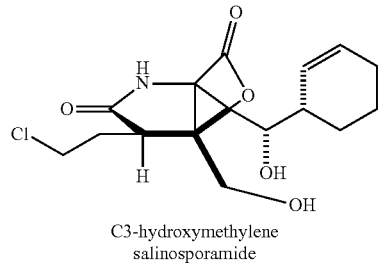
C3-hydroxymethylene salinosporamide

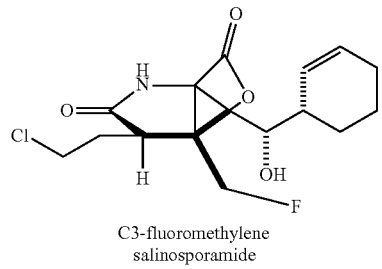
C3-fluoromethylene salinosporamide

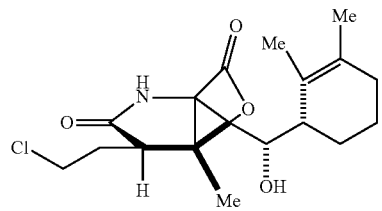

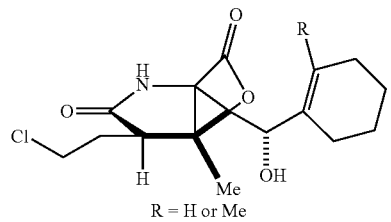
R = H or Me

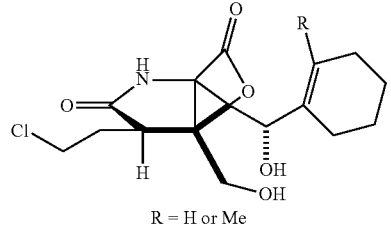
R = H or Me

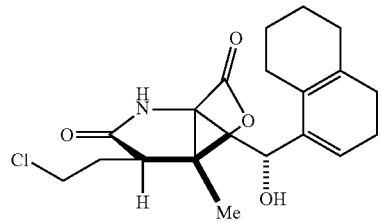

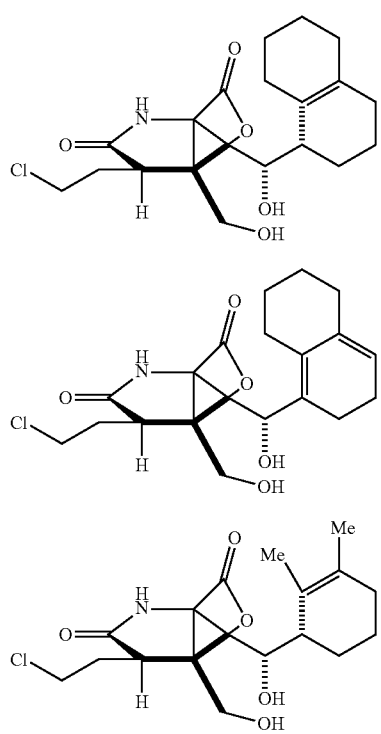
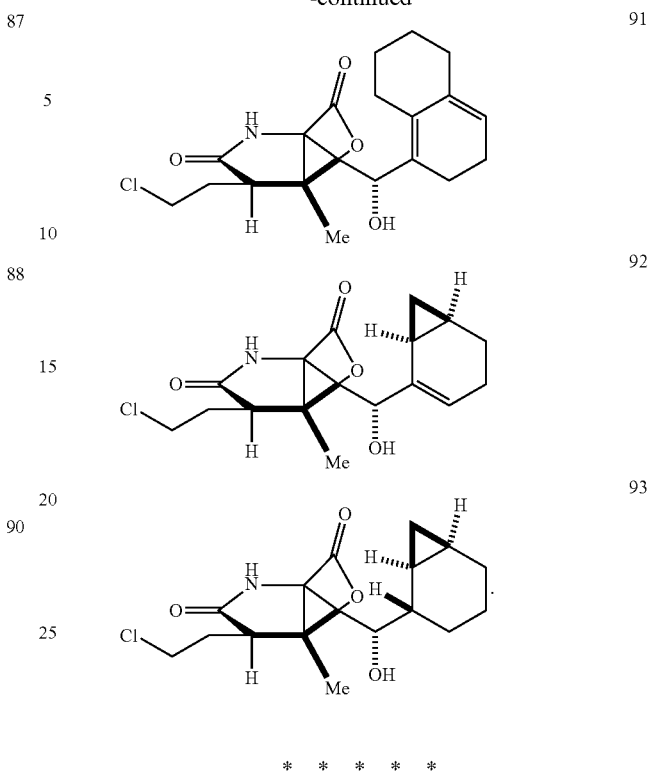
* * * * *

UNITED STATES PATENT AND TRADEMARK OFFICE
CERTIFICATE OF CORRECTION

| | | Page 1 of 1 |
|---|---|---|
| PATENT NO. | : 8,088,923 B2 | |
| APPLICATION NO. | : 11/775216 | |
| DATED | : January 3, 2012 | |
| INVENTOR(S) | : D. Romo et al. | |

It is certified that error appears in the above-identified patent and that said Letters Patent is hereby corrected as shown below:

In the Claims

| COLUMN | LINE | |
|---|---|---|
| 91 | 35 | After "and optical isomers thereof; and wherein (b) is as follows:" |
| (Claim 1, | line 21) | insert a new paragraph and --(b)-- |

Signed and Sealed this
Twenty-seventh Day of May, 2014

Michelle K. Lee
*Deputy Director of the United States Patent and Trademark Office*

SEQUENCE LISTING

```
<160> NUMBER OF SEQ ID NOS: 2

<210> SEQ ID NO 1
<211> LENGTH: 33
<212> TYPE: DNA
<213> ORGANISM: Artificial
<220> FEATURE:
<223> OTHER INFORMATION: Synthetic primer

<400> SEQUENCE: 1
atgacgccca aggaggatgg tctggcccag cag                              33

<210> SEQ ID NO 2
<211> LENGTH: 26
<212> TYPE: DNA
<213> ORGANISM: Artificial
<220> FEATURE:
<223> OTHER INFORMATION: Synthetic primer

<400> SEQUENCE: 2
gccctcccgc acgctcacgc gtggct                                      26
```